United States Patent
Yu et al.

(10) Patent No.: US 9,782,141 B2
(45) Date of Patent: Oct. 10, 2017

(54) MOTION TRACKING SYSTEM FOR REAL TIME ADAPTIVE MOTION COMPENSATION IN BIOMEDICAL IMAGING

(71) Applicants: KINETICOR, INC., Honolulu, HI (US); THE UNIVERSITY OF HAWAII, Honolulu, HI (US); THE QUEEN'S MEDICAL CENTER, Honolulu, HI (US)

(72) Inventors: Jeffrey N. Yu, Honolulu, HI (US); Thomas Michael Ernst, Honolulu, HI (US)

(73) Assignees: KINETICOR, INC., Honolulu, HI (US); THE UNIVERSITY OF HAWAII, Honolulu, HI (US); THE QUEEN'S MEDICAL CENTER, Honolulu, HI (US)

( * ) Notice: Subject to any disclaimer, the term of this patent is extended or adjusted under 35 U.S.C. 154(b) by 54 days.

(21) Appl. No.: 14/762,583

(22) PCT Filed: Jan. 29, 2014

(86) PCT No.: PCT/US2014/013546
§ 371 (c)(1),
(2) Date: Jul. 22, 2015

(87) PCT Pub. No.: WO2014/120734
PCT Pub. Date: Aug. 7, 2014

(65) Prior Publication Data
US 2015/0366527 A1    Dec. 24, 2015

Related U.S. Application Data
(60) Provisional application No. 61/759,883, filed on Feb. 1, 2013.

(51) Int. Cl.
*A61B 5/055* (2006.01)
*A61B 6/03* (2006.01)
(Continued)

(52) U.S. Cl.
CPC ............. *A61B 6/527* (2013.01); *A61B 5/055* (2013.01); *A61B 5/721* (2013.01); *A61B 6/032* (2013.01);
(Continued)

(58) Field of Classification Search
CPC ......... A61B 6/527; A61B 5/055; A61B 5/721; A61B 6/032; A61B 6/037; A61B 6/0492;
(Continued)

(56) References Cited

U.S. PATENT DOCUMENTS

| 3,811,213 A | 5/1974 | Eaves |
| 4,689,999 A | 9/1987 | Shkedi |

(Continued)

FOREIGN PATENT DOCUMENTS

| CH | EP 0904733 A1 * | 3/1999 | ........... A61B 5/1114 |
| CN | 105392423 | 3/2016 | |

(Continued)

OTHER PUBLICATIONS

US 7,906,604, 03/2011, Lejeune et al. (withdrawn)

(Continued)

*Primary Examiner* — Jon Chang
(74) *Attorney, Agent, or Firm* — Knobbe Martens Olson & Bear LLP

(57) ABSTRACT

The disclosure herein provides methods, systems, and devices for tracking motion of a patient or object of interest during biomedical imaging and for compensating for that motion in the biomedical imaging scanner and/or the resulting images to reduce or eliminate motion artifacts. In an embodiment, a motion tracking system is configured to (Continued)

overlay tracking data over biomedical imaging data in order to display the tracking data along with its associated image data. In an embodiment, a motion tracking system is configured to overlay tracking data over biomedical imaging data in order to display the tracking data along with its associated image data. In an embodiment, one or more detectors are configured to detect images of a patient, and a detector processing interface is configured to analyze the images to estimate motion or movement of the patient and to generate tracking data describing the patient's motion. The detector processing interface is configured to send the tracking data to a scanner controller to enable adjustment of scanning parameters in real-time in response to the patient's motion.

16 Claims, 34 Drawing Sheets

(51) Int. Cl.
*G06T 7/20* (2017.01)
*A61B 6/00* (2006.01)
*A61B 6/04* (2006.01)
*A61B 5/00* (2006.01)
*G06T 7/00* (2017.01)
*G06T 7/73* (2017.01)
*G06T 7/207* (2017.01)

(52) U.S. Cl.
CPC ............ *A61B 6/037* (2013.01); *A61B 6/0492* (2013.01); *G06T 7/0012* (2013.01); *G06T 7/207* (2017.01); *G06T 7/73* (2017.01); *G06T 2200/04* (2013.01); *G06T 2207/10072* (2013.01); *G06T 2207/30004* (2013.01); *G06T 2211/428* (2013.01)

(58) Field of Classification Search
CPC ......... G06T 7/207; G06T 7/73; G06T 7/0012; G06T 2200/04; G06T 2207/10072; G06T 2207/30004; G06T 2211/428
See application file for complete search history.

(56) References Cited

U.S. PATENT DOCUMENTS

| | | |
|---|---|---|
| 4,724,386 A | 2/1988 | Haacke et al. |
| 4,894,129 A | 1/1990 | Leiponen et al. |
| 4,923,295 A | 5/1990 | Sireul et al. |
| 4,953,554 A | 9/1990 | Zerhouni et al. |
| 4,988,886 A | 1/1991 | Palum et al. |
| 5,075,562 A | 12/1991 | Greivenkamp et al. |
| 5,318,026 A | 6/1994 | Pelc |
| 5,515,711 A | 5/1996 | Hinkle |
| 5,545,993 A | 8/1996 | Taguchi et al. |
| 5,615,677 A | 4/1997 | Pelc et al. |
| 5,687,725 A | 11/1997 | Wendt |
| 5,728,935 A | 3/1998 | Czompo |
| 5,802,202 A | 9/1998 | Yamada et al. |
| 5,835,223 A | 11/1998 | Zwemer et al. |
| 5,886,257 A | 3/1999 | Gustafson et al. |
| 5,889,505 A | 3/1999 | Toyama |
| 5,936,722 A | 8/1999 | Armstrong et al. |
| 5,936,723 A | 8/1999 | Schmidt et al. |
| 5,947,900 A | 9/1999 | Derbyshire et al. |
| 5,987,349 A | 11/1999 | Schulz |
| 6,031,888 A | 2/2000 | Ivan et al. |
| 6,044,308 A | 3/2000 | Huissoon |
| 6,057,680 A | 5/2000 | Foo et al. |
| 6,061,644 A | 5/2000 | Leis |
| 6,088,482 A | 7/2000 | He |
| 6,144,875 A | 11/2000 | Schweikard et al. |
| 6,236,737 B1 | 5/2001 | Gregson et al. |
| 6,246,900 B1 | 6/2001 | Cosman et al. |
| 6,279,579 B1 | 8/2001 | Riaziat et al. |
| 6,285,902 B1 | 9/2001 | Kienzle, III et al. |
| 6,289,235 B1 | 9/2001 | Webber |
| 6,292,683 B1 | 9/2001 | Gupta et al. |
| 6,298,262 B1 | 10/2001 | Franck et al. |
| 6,381,485 B1 | 4/2002 | Hunter et al. |
| 6,384,908 B1 | 5/2002 | Schmidt et al. |
| 6,390,982 B1 | 5/2002 | Bova et al. |
| 6,402,762 B2 | 6/2002 | Hunter et al. |
| 6,405,072 B1 | 6/2002 | Cosman |
| 6,421,551 B1 | 7/2002 | Kuth et al. |
| 6,467,905 B1 | 10/2002 | Stahl et al. |
| 6,474,159 B1 | 11/2002 | Foxlin et al. |
| 6,484,131 B1 | 11/2002 | Amorai-Moriya et al. |
| 6,490,475 B1 | 12/2002 | Seeley et al. |
| 6,501,981 B1 | 12/2002 | Schweikard et al. |
| 6,587,707 B2 | 7/2003 | Nehrke et al. |
| 6,621,889 B1 | 9/2003 | Mostafavi |
| 6,650,920 B2 | 11/2003 | Schaldach et al. |
| 6,662,036 B2 | 12/2003 | Cosman |
| 6,687,528 B2 | 2/2004 | Gupta et al. |
| 6,690,965 B1 | 2/2004 | Riaziat et al. |
| 6,711,431 B2 | 3/2004 | Pratt et al. |
| 6,731,970 B2 | 5/2004 | Schlossbauer et al. |
| 6,758,218 B2 | 7/2004 | Anthony |
| 6,771,997 B2 | 8/2004 | Schaffer |
| 6,794,869 B2 | 9/2004 | Brittain |
| 6,856,827 B2 | 2/2005 | Seeley et al. |
| 6,856,828 B2 | 2/2005 | Cossette et al. |
| 6,876,198 B2 | 4/2005 | Watanabe et al. |
| 6,888,924 B2 | 5/2005 | Claus et al. |
| 6,891,374 B2 | 5/2005 | Brittain |
| 6,892,089 B1 | 5/2005 | Prince et al. |
| 6,897,655 B2 | 5/2005 | Brittain et al. |
| 6,913,603 B2 | 7/2005 | Knopp et al. |
| 6,937,696 B1 | 8/2005 | Mostafavi |
| 6,959,266 B1 | 10/2005 | Mostafavi |
| 6,973,202 B2 | 12/2005 | Mostafavi |
| 6,980,679 B2 | 12/2005 | Jeung et al. |
| 7,007,699 B2 | 3/2006 | Martinelli et al. |
| 7,107,091 B2 | 9/2006 | Jutras et al. |
| 7,110,805 B2 | 9/2006 | Machida |
| 7,123,758 B2 | 10/2006 | Jeung et al. |
| 7,171,257 B2 | 1/2007 | Thomson |
| 7,176,440 B2 | 2/2007 | Cofer et al. |
| 7,191,100 B2 | 3/2007 | Mostafavi |
| 7,204,254 B2 | 4/2007 | Riaziat et al. |
| 7,209,777 B2 | 4/2007 | Saranathan et al. |
| 7,209,977 B2 | 4/2007 | Acharya et al. |
| 7,260,253 B2 | 8/2007 | Rahn et al. |
| 7,260,426 B2 | 8/2007 | Schweikard et al. |
| 7,295,007 B2 | 11/2007 | Dold |
| 7,313,430 B2 | 12/2007 | Urquhart et al. |
| 7,327,865 B2 | 2/2008 | Fu et al. |
| 7,348,776 B1 | 3/2008 | Aksoy et al. |
| 7,403,638 B2 | 7/2008 | Jeung et al. |
| 7,494,277 B2 | 2/2009 | Setala |
| 7,498,811 B2 | 3/2009 | Macfarlane et al. |
| 7,505,805 B2 | 3/2009 | Kuroda |
| 7,535,411 B2 | 5/2009 | Falco |
| 7,551,089 B2 | 6/2009 | Sawyer |
| 7,561,909 B1 | 7/2009 | Pai et al. |
| 7,567,697 B2 | 7/2009 | Mostafavi |
| 7,573,269 B2 | 8/2009 | Yao |
| 7,602,301 B1 | 10/2009 | Stirling et al. |
| 7,603,155 B2 | 10/2009 | Jensen |
| 7,623,623 B2 | 11/2009 | Raanes et al. |
| 7,657,300 B2 | 2/2010 | Hunter et al. |
| 7,657,301 B2 | 2/2010 | Mate et al. |
| 7,659,521 B2 | 2/2010 | Pedroni |
| 7,660,623 B2 | 2/2010 | Hunter et al. |
| 7,668,288 B2 | 2/2010 | Conwell et al. |
| 7,689,263 B1 | 3/2010 | Fung et al. |
| 7,702,380 B1 | 4/2010 | Dean |
| 7,715,604 B2 | 5/2010 | Sun et al. |
| 7,742,077 B2 | 6/2010 | Sablak et al. |
| 7,742,621 B2 | 6/2010 | Hammoud et al. |

(56) References Cited

U.S. PATENT DOCUMENTS

| | | |
|---|---|---|
| 7,742,804 B2 | 6/2010 | Faul et al. |
| 7,744,528 B2 | 6/2010 | Wallace et al. |
| 7,760,908 B2 | 7/2010 | Curtner et al. |
| 7,766,837 B2 | 8/2010 | Pedrizzetti et al. |
| 7,769,430 B2 | 8/2010 | Mostafavi |
| 7,772,569 B2 | 8/2010 | Bewersdorf et al. |
| 7,787,011 B2 | 8/2010 | Zhou et al. |
| 7,787,935 B2 | 8/2010 | Dumoulin et al. |
| 7,791,808 B2 | 9/2010 | French et al. |
| 7,792,249 B2 | 9/2010 | Gertner et al. |
| 7,796,154 B2 | 9/2010 | Senior et al. |
| 7,798,730 B2 | 9/2010 | Westerweck |
| 7,801,330 B2 | 9/2010 | Zhang et al. |
| 7,805,987 B1 | 10/2010 | Smith |
| 7,806,604 B2 | 10/2010 | Bazakos et al. |
| 7,817,046 B2 | 10/2010 | Coveley et al. |
| 7,817,824 B2 | 10/2010 | Liang et al. |
| 7,819,818 B2 | 10/2010 | Ghajar |
| 7,833,221 B2 | 11/2010 | Voegele |
| 7,834,846 B1 | 11/2010 | Bell |
| 7,835,783 B1 | 11/2010 | Aletras |
| 7,839,551 B2 | 11/2010 | Lee et al. |
| 7,840,253 B2 | 11/2010 | Tremblay et al. |
| 7,844,094 B2 | 11/2010 | Jeung et al. |
| 7,844,320 B2 | 11/2010 | Shahidi |
| 7,850,526 B2 | 12/2010 | Zalewski et al. |
| 7,860,301 B2 | 12/2010 | Se et al. |
| 7,866,818 B2 | 1/2011 | Schroeder et al. |
| 7,868,282 B2 | 1/2011 | Lee et al. |
| 7,878,652 B2 | 2/2011 | Chen et al. |
| 7,883,415 B2 | 2/2011 | Larsen et al. |
| 7,889,907 B2 | 2/2011 | Engelbart et al. |
| 7,894,877 B2 | 2/2011 | Lewin et al. |
| 7,902,825 B2 | 3/2011 | Bammer et al. |
| 7,907,987 B2 | 3/2011 | Dempsey |
| 7,908,060 B2 | 3/2011 | Basson et al. |
| 7,908,233 B2 | 3/2011 | Angell et al. |
| 7,911,207 B2 | 3/2011 | Macfarlane et al. |
| 7,912,532 B2 | 3/2011 | Schmidt et al. |
| 7,920,250 B2 | 4/2011 | Robert et al. |
| 7,920,911 B2 | 4/2011 | Hoshino et al. |
| 7,925,066 B2 | 4/2011 | Ruohonen et al. |
| 7,925,549 B2 | 4/2011 | Looney et al. |
| 7,931,370 B2 | 4/2011 | Bartomen |
| 7,944,354 B2 | 5/2011 | Kangas et al. |
| 7,944,454 B2 | 5/2011 | Zhou et al. |
| 7,945,304 B2 | 5/2011 | Feinberg |
| 7,946,921 B2 | 5/2011 | Ofek et al. |
| 7,962,197 B2 | 6/2011 | Rioux et al. |
| 7,971,999 B2 | 7/2011 | Zinser |
| 7,977,942 B2 | 7/2011 | White |
| 7,978,925 B1 | 7/2011 | Souchard |
| 7,988,288 B2 | 8/2011 | Donaldson |
| 7,990,365 B2 | 8/2011 | Marvit et al. |
| 8,005,571 B2 | 8/2011 | Sutherland et al. |
| 8,009,198 B2 | 8/2011 | Alhadef |
| 8,019,170 B2 | 9/2011 | Wang et al. |
| 8,021,231 B2 | 9/2011 | Walker et al. |
| 8,022,982 B2 | 9/2011 | Thorn |
| 8,024,026 B2 | 9/2011 | Groszmann |
| 8,031,909 B2 | 10/2011 | Se et al. |
| 8,031,933 B2 | 10/2011 | Se et al. |
| 8,036,425 B2 | 10/2011 | Hou |
| 8,041,077 B2 | 10/2011 | Bell |
| 8,041,412 B2 | 10/2011 | Glossop et al. |
| 8,048,002 B2 | 11/2011 | Ghajar |
| 8,049,867 B2 | 11/2011 | Bridges et al. |
| 8,055,020 B2 | 11/2011 | Meuter et al. |
| 8,055,049 B2 | 11/2011 | Stayman et al. |
| 8,060,185 B2 | 11/2011 | Hunter et al. |
| 8,063,929 B2 | 11/2011 | Kurtz et al. |
| 8,073,197 B2 | 12/2011 | Xu et al. |
| 8,077,914 B1 | 12/2011 | Kaplan |
| 8,085,302 B2 | 12/2011 | Zhang et al. |
| 8,086,026 B2 | 12/2011 | Schulz |
| 8,086,299 B2 | 12/2011 | Adler et al. |
| RE43,147 E | 1/2012 | Aviv |
| 8,094,193 B2 | 1/2012 | Peterson |
| 8,095,203 B2 | 1/2012 | Wright et al. |
| 8,095,209 B2 | 1/2012 | Flaherty |
| 8,098,889 B2 | 1/2012 | Zhu et al. |
| 8,113,991 B2 | 2/2012 | Kutliroff |
| 8,116,527 B2 | 2/2012 | Sabol |
| 8,121,356 B2 | 2/2012 | Friedman |
| 8,121,361 B2 | 2/2012 | Ernst et al. |
| 8,134,597 B2 | 3/2012 | Thorn |
| 8,135,201 B2 | 3/2012 | Smith et al. |
| 8,139,029 B2 | 3/2012 | Boillot |
| 8,139,896 B1 | 3/2012 | Ahiska |
| 8,144,118 B2 | 3/2012 | Hildreth |
| 8,144,148 B2 | 3/2012 | El Dokor |
| 8,150,063 B2 | 4/2012 | Chen |
| 8,150,498 B2 | 4/2012 | Gielen et al. |
| 8,160,304 B2 | 4/2012 | Rhoads |
| 8,165,844 B2 | 4/2012 | Luinge et al. |
| 8,167,802 B2 | 5/2012 | Baba et al. |
| 8,172,573 B2 | 5/2012 | Sonenfeld et al. |
| 8,175,332 B2 | 5/2012 | Herrington |
| 8,179,604 B1 | 5/2012 | Prada Gomez |
| 8,180,428 B2 | 5/2012 | Kaiser et al. |
| 8,180,432 B2 | 5/2012 | Sayeh |
| 8,187,097 B1 | 5/2012 | Zhang |
| 8,189,869 B2 | 5/2012 | Bell |
| 8,189,889 B2 | 5/2012 | Pearlstein et al. |
| 8,189,926 B2 | 5/2012 | Sharma |
| 8,190,233 B2 | 5/2012 | Dempsey |
| 8,191,359 B2 | 6/2012 | White et al. |
| 8,194,134 B2 | 6/2012 | Furukawa |
| 8,195,084 B2 | 6/2012 | Xiao |
| 8,199,983 B2 | 6/2012 | Qureshi |
| 8,206,219 B2 | 6/2012 | Shum |
| 8,207,967 B1 | 6/2012 | El Dokor |
| 8,208,758 B2 | 6/2012 | Wang |
| 8,213,693 B1 | 7/2012 | Li |
| 8,214,012 B2 | 7/2012 | Zuccolotto et al. |
| 8,214,016 B2 | 7/2012 | Lavallee et al. |
| 8,216,016 B2 | 7/2012 | Yamagishi et al. |
| 8,218,818 B2 | 7/2012 | Cobb |
| 8,218,819 B2 | 7/2012 | Cobb |
| 8,218,825 B2 | 7/2012 | Gordon |
| 8,221,399 B2 | 7/2012 | Amano |
| 8,223,147 B1 | 7/2012 | El Dokor |
| 8,224,423 B2 | 7/2012 | Faul |
| 8,226,574 B2 | 7/2012 | Whillock |
| 8,229,163 B2 | 7/2012 | Coleman |
| 8,229,166 B2 | 7/2012 | Teng |
| 8,229,184 B2 | 7/2012 | Benkley |
| 8,232,872 B2 | 7/2012 | Zeng |
| 8,235,529 B1 | 8/2012 | Raffle |
| 8,235,530 B2 | 8/2012 | Maad |
| 8,241,125 B2 | 8/2012 | Huges |
| 8,243,136 B2 | 8/2012 | Aota |
| 8,243,269 B2 | 8/2012 | Matousek |
| 8,243,996 B2 | 8/2012 | Steinberg |
| 8,248,372 B2 | 8/2012 | Saila |
| 8,249,691 B2 | 8/2012 | Chase |
| 8,253,770 B2 | 8/2012 | Kurtz |
| 8,253,774 B2 | 8/2012 | Huitema |
| 8,253,778 B2 | 8/2012 | Atsushi |
| 8,259,109 B2 | 9/2012 | El Dokor |
| 8,260,036 B2 | 9/2012 | Hamza et al. |
| 8,279,288 B2 | 10/2012 | Son |
| 8,284,157 B2 | 10/2012 | Markovic |
| 8,284,847 B2 | 10/2012 | Adermann |
| 8,287,373 B2 | 10/2012 | Marx |
| 8,289,390 B2 | 10/2012 | Aggarwal |
| 8,289,392 B2 | 10/2012 | Senior et al. |
| 8,290,208 B2 | 10/2012 | Kurtz |
| 8,290,229 B2 | 10/2012 | Qureshi |
| 8,295,573 B2 | 10/2012 | Bredno et al. |
| 8,301,226 B2 | 10/2012 | Csavoy et al. |
| 8,306,260 B2 | 11/2012 | Zhu |
| 8,306,267 B1 | 11/2012 | Gossweiler, III |
| 8,306,274 B2 | 11/2012 | Grycewicz |

(56) References Cited

U.S. PATENT DOCUMENTS

| | | |
|---|---|---|
| 8,306,663 B2 | 11/2012 | Wickham |
| 8,310,656 B2 | 11/2012 | Zalewski |
| 8,310,662 B2 | 11/2012 | Mehr |
| 8,311,611 B2 | 11/2012 | Csavoy et al. |
| 8,314,854 B2 | 11/2012 | Yoon |
| 8,315,691 B2 | 11/2012 | Sumanaweera et al. |
| 8,316,324 B2 | 11/2012 | Boillot |
| 8,320,621 B2 | 11/2012 | McEldowney |
| 8,320,709 B2 | 11/2012 | Aratani et al. |
| 8,323,106 B2 | 12/2012 | Zalewski |
| 8,325,228 B2 | 12/2012 | Mariadoss |
| 8,330,811 B2 | 12/2012 | Macguire, Jr. |
| 8,330,812 B2 | 12/2012 | Maguire, Jr. |
| 8,331,019 B2 | 12/2012 | Cheong |
| 8,334,900 B2 | 12/2012 | Qu et al. |
| 8,339,282 B2 | 12/2012 | Noble |
| 8,351,651 B2 | 1/2013 | Lee |
| 8,368,586 B2 | 2/2013 | Mohamadi |
| 8,369,574 B2 | 2/2013 | Hu |
| 8,374,393 B2 | 2/2013 | Cobb |
| 8,374,411 B2 | 2/2013 | Ernst et al. |
| 8,374,674 B2 | 2/2013 | Gertner |
| 8,376,226 B2 | 2/2013 | Dennard |
| 8,376,827 B2 | 2/2013 | Cammegh |
| 8,379,927 B2 | 2/2013 | Taylor |
| 8,380,284 B2 | 2/2013 | Saranathan et al. |
| 8,386,011 B2 | 2/2013 | Wieczorek |
| 8,390,291 B2 | 3/2013 | Macfarlane et al. |
| 8,390,729 B2 | 3/2013 | Long |
| 8,395,620 B2 | 3/2013 | El Dokor |
| 8,396,654 B1 | 3/2013 | Simmons et al. |
| 8,400,398 B2 | 3/2013 | Schoen |
| 8,400,490 B2 | 3/2013 | Apostolopoulos |
| 8,405,491 B2 | 3/2013 | Fong |
| 8,405,656 B2 | 3/2013 | El Dokor |
| 8,405,717 B2 | 3/2013 | Kim |
| 8,406,845 B2 | 3/2013 | Komistek et al. |
| 8,411,931 B2 | 4/2013 | Zhou |
| 8,427,538 B2 | 4/2013 | Ahiska |
| 8,428,319 B2 | 4/2013 | Tsin et al. |
| 8,571,293 B2 | 10/2013 | Ernst et al. |
| 8,615,127 B2 | 12/2013 | Fitzpatrick |
| 8,744,154 B2 | 6/2014 | Van Den Brink |
| 8,848,977 B2 | 9/2014 | Bammer et al. |
| 8,862,420 B2 | 10/2014 | Ferran et al. |
| 8,953,847 B2 | 2/2015 | Moden |
| 8,996,094 B2 | 3/2015 | Schouenborg et al. |
| 9,076,212 B2 | 7/2015 | Ernst |
| 9,082,177 B2 | 7/2015 | Sebok |
| 9,084,629 B1 | 7/2015 | Rosa |
| 9,103,897 B2 | 8/2015 | Herbst et al. |
| 9,138,175 B2 | 9/2015 | Ernst et al. |
| 9,173,715 B2 | 11/2015 | Baumgartner |
| 9,176,932 B2 | 11/2015 | Baggen et al. |
| 9,305,365 B2 | 4/2016 | Lovberg et al. |
| 9,395,386 B2 | 7/2016 | Corder et al. |
| 9,451,926 B2 | 9/2016 | Kinahan et al. |
| 9,606,209 B2 | 3/2017 | Ernst et al. |
| 9,607,377 B2 | 3/2017 | Lovberg et al. |
| 2002/0082496 A1 | 6/2002 | Kuth |
| 2002/0091422 A1 | 7/2002 | Greenberg et al. |
| 2002/0115931 A1 | 8/2002 | Strauss et al. |
| 2002/0180436 A1 | 12/2002 | Dale et al. |
| 2002/0188194 A1 | 12/2002 | Cosman |
| 2003/0063292 A1 | 4/2003 | Mostafavi |
| 2003/0088177 A1 | 5/2003 | Totterman et al. |
| 2003/0116166 A1 | 6/2003 | Anthony |
| 2003/0130574 A1 | 7/2003 | Stoyle |
| 2004/0071324 A1 | 4/2004 | Norris et al. |
| 2004/0116804 A1 | 6/2004 | Mostafavi |
| 2004/0140804 A1 | 7/2004 | Polzin et al. |
| 2004/0171927 A1 | 9/2004 | Lowen et al. |
| 2005/0027194 A1 | 2/2005 | Adler et al. |
| 2005/0054910 A1 | 3/2005 | Tremblay et al. |
| 2005/0105772 A1 | 5/2005 | Voronka et al. |
| 2005/0107685 A1 | 5/2005 | Seeber |
| 2005/0137475 A1 | 6/2005 | Dold et al. |
| 2005/0148854 A1 | 7/2005 | Ito et al. |
| 2005/0283068 A1 | 12/2005 | Zuccoloto et al. |
| 2006/0004281 A1 | 1/2006 | Saracen |
| 2006/0045310 A1 | 3/2006 | Tu et al. |
| 2006/0074292 A1 | 4/2006 | Thomson et al. |
| 2006/0241405 A1 | 10/2006 | Leitner et al. |
| 2007/0093709 A1 | 4/2007 | Abernathie |
| 2007/0206836 A1 | 9/2007 | Yoon |
| 2007/0239169 A1 | 10/2007 | Plaskos et al. |
| 2007/0280508 A1 | 12/2007 | Ernst et al. |
| 2008/0039713 A1 | 2/2008 | Thomson et al. |
| 2008/0181358 A1 | 7/2008 | Van Kampen et al. |
| 2008/0183074 A1 | 7/2008 | Carls et al. |
| 2008/0212835 A1 | 9/2008 | Tavor |
| 2008/0221442 A1 | 9/2008 | Tolkowsky et al. |
| 2008/0273754 A1 | 11/2008 | Hick et al. |
| 2008/0287728 A1 | 11/2008 | Mostafavi et al. |
| 2008/0287780 A1 | 11/2008 | Chase et al. |
| 2008/0317313 A1 | 12/2008 | Goddard et al. |
| 2009/0028411 A1 | 1/2009 | Pfeuffer |
| 2009/0052760 A1 | 2/2009 | Smith et al. |
| 2009/0185663 A1 | 7/2009 | Gaines, Jr. |
| 2009/0209846 A1 | 8/2009 | Bammer |
| 2009/0253985 A1 | 10/2009 | Shachar et al. |
| 2009/0304297 A1 | 12/2009 | Adabala et al. |
| 2009/0306499 A1 | 12/2009 | Van Vorhis et al. |
| 2010/0054579 A1 | 3/2010 | Okutomi |
| 2010/0057059 A1 | 3/2010 | Makino |
| 2010/0059679 A1 | 3/2010 | Albrecht |
| 2010/0069742 A1 | 3/2010 | Partain et al. |
| 2010/0091089 A1 | 4/2010 | Cromwell et al. |
| 2010/0099981 A1 | 4/2010 | Fishel |
| 2010/0125191 A1 | 5/2010 | Sahin |
| 2010/0137709 A1 | 6/2010 | Gardner et al. |
| 2010/0148774 A1 | 6/2010 | Kamata |
| 2010/0149099 A1 | 6/2010 | Elias |
| 2010/0149315 A1 | 6/2010 | Qu |
| 2010/0160775 A1 | 6/2010 | Pankratov |
| 2010/0164862 A1 | 7/2010 | Sullivan |
| 2010/0165293 A1 | 7/2010 | Tanassi et al. |
| 2010/0167246 A1 | 7/2010 | Ghajar |
| 2010/0172567 A1 | 7/2010 | Prokoski |
| 2010/0177929 A1 | 7/2010 | Kurtz |
| 2010/0178966 A1 | 7/2010 | Suydoux |
| 2010/0179390 A1 | 7/2010 | Davis |
| 2010/0179413 A1 | 7/2010 | Kadour et al. |
| 2010/0183196 A1 | 7/2010 | Fu et al. |
| 2010/0191631 A1 | 7/2010 | Weidmann |
| 2010/0194879 A1 | 8/2010 | Pasveer |
| 2010/0198067 A1 | 8/2010 | Mahfouz |
| 2010/0198101 A1 | 8/2010 | Song |
| 2010/0198112 A1 | 8/2010 | Maad |
| 2010/0199232 A1 | 8/2010 | Mistry |
| 2010/0210350 A9 | 8/2010 | Walker |
| 2010/0214267 A1 | 8/2010 | Radivojevic |
| 2010/0231511 A1 | 9/2010 | Henty |
| 2010/0231692 A1 | 9/2010 | Perlman |
| 2010/0245536 A1 | 9/2010 | Huitema |
| 2010/0245593 A1 | 9/2010 | Kim |
| 2010/0251924 A1 | 10/2010 | Taylor |
| 2010/0253762 A1 | 10/2010 | Cheong |
| 2010/0268072 A1 | 10/2010 | Hall et al. |
| 2010/0277571 A1 | 11/2010 | Xu |
| 2010/0282902 A1 | 11/2010 | Rajasingham |
| 2010/0283833 A1 | 11/2010 | Yeh |
| 2010/0284119 A1 | 11/2010 | Coakley |
| 2010/0289899 A1 | 11/2010 | Hendron |
| 2010/0290668 A1 | 11/2010 | Friedman |
| 2010/0292841 A1 | 11/2010 | Wickham |
| 2010/0295718 A1 | 11/2010 | Mohamadi |
| 2010/0296701 A1 | 11/2010 | Hu |
| 2010/0302142 A1 | 12/2010 | French |
| 2010/0303289 A1 | 12/2010 | Polzin |
| 2010/0311512 A1 | 12/2010 | Lock |
| 2010/0321505 A1 | 12/2010 | Kokubun |
| 2010/0328055 A1 | 12/2010 | Fong |
| 2010/0328201 A1 | 12/2010 | Marvit |

(56) References Cited

U.S. PATENT DOCUMENTS

| | | |
|---|---|---|
| 2010/0328267 A1 | 12/2010 | Chen |
| 2010/0330912 A1 | 12/2010 | Saila |
| 2011/0001699 A1 | 1/2011 | Jacobsen |
| 2011/0006991 A1 | 1/2011 | Elias |
| 2011/0007939 A1 | 1/2011 | Teng |
| 2011/0007946 A1 | 1/2011 | Liang |
| 2011/0008759 A1 | 1/2011 | Usui |
| 2011/0015521 A1 | 1/2011 | Faul |
| 2011/0019001 A1 | 1/2011 | Rhoads |
| 2011/0025853 A1 | 2/2011 | Richardson |
| 2011/0038520 A1 | 2/2011 | Yui |
| 2011/0043631 A1 | 2/2011 | Marman |
| 2011/0043759 A1 | 2/2011 | Bushinsky |
| 2011/0050562 A1 | 3/2011 | Schoen |
| 2011/0050569 A1 | 3/2011 | Marvit |
| 2011/0050947 A1 | 3/2011 | Marman |
| 2011/0052002 A1 | 3/2011 | Cobb |
| 2011/0052003 A1 | 3/2011 | Cobb |
| 2011/0052015 A1 | 3/2011 | Saund |
| 2011/0054870 A1 | 3/2011 | Dariush |
| 2011/0057816 A1 | 3/2011 | Noble |
| 2011/0058020 A1 | 3/2011 | Dieckmann |
| 2011/0064290 A1* | 3/2011 | Punithakumar ...... G06K 9/6207 382/131 |
| 2011/0069207 A1 | 3/2011 | Steinberg |
| 2011/0074675 A1 | 3/2011 | Shiming |
| 2011/0081000 A1 | 4/2011 | Gertner |
| 2011/0081043 A1 | 4/2011 | Sabol |
| 2011/0085704 A1 | 4/2011 | Han |
| 2011/0092781 A1 | 4/2011 | Gertner |
| 2011/0102549 A1 | 5/2011 | Takahashi |
| 2011/0105883 A1 | 5/2011 | Lake et al. |
| 2011/0105893 A1 | 5/2011 | Akins |
| 2011/0115793 A1 | 5/2011 | Grycewicz |
| 2011/0115892 A1 | 5/2011 | Fan |
| 2011/0116683 A1 | 5/2011 | Kramer et al. |
| 2011/0117528 A1 | 5/2011 | Marciello et al. |
| 2011/0118032 A1 | 5/2011 | Zalewski |
| 2011/0133917 A1 | 6/2011 | Zeng |
| 2011/0142411 A1 | 6/2011 | Camp |
| 2011/0150271 A1 | 6/2011 | Lee |
| 2011/0157168 A1 | 6/2011 | Bennett |
| 2011/0157358 A1 | 6/2011 | Bell |
| 2011/0157370 A1 | 6/2011 | Livesey |
| 2011/0160569 A1 | 6/2011 | Cohen et al. |
| 2011/0172060 A1 | 7/2011 | Morales |
| 2011/0172521 A1 | 7/2011 | Zdeblick et al. |
| 2011/0175801 A1 | 7/2011 | Markovic |
| 2011/0175809 A1 | 7/2011 | Markovic |
| 2011/0175810 A1 | 7/2011 | Markovic |
| 2011/0176723 A1 | 7/2011 | Ali et al. |
| 2011/0180695 A1 | 7/2011 | Li |
| 2011/0181893 A1 | 7/2011 | MacFarlane |
| 2011/0182472 A1 | 7/2011 | Hansen |
| 2011/0187640 A1 | 8/2011 | Jacobsen |
| 2011/0193939 A1 | 8/2011 | Vassigh |
| 2011/0199461 A1 | 8/2011 | Horio |
| 2011/0201916 A1 | 8/2011 | Duyn et al. |
| 2011/0201939 A1 | 8/2011 | Hubschman et al. |
| 2011/0202306 A1 | 8/2011 | Eng |
| 2011/0205358 A1 | 8/2011 | Aota |
| 2011/0207089 A1 | 8/2011 | Lagettie |
| 2011/0208437 A1 | 8/2011 | Teicher |
| 2011/0216002 A1 | 9/2011 | Weising |
| 2011/0216180 A1 | 9/2011 | Pasini |
| 2011/0221770 A1 | 9/2011 | Kruglick |
| 2011/0229862 A1 | 9/2011 | Parikh |
| 2011/0230755 A1 | 9/2011 | MacFarlane et al. |
| 2011/0234807 A1 | 9/2011 | Jones |
| 2011/0234834 A1 | 9/2011 | Sugimoto |
| 2011/0235855 A1 | 9/2011 | Smith |
| 2011/0237933 A1 | 9/2011 | Cohen |
| 2011/0242134 A1 | 10/2011 | Miller |
| 2011/0244939 A1 | 10/2011 | Cammegh |
| 2011/0250929 A1 | 10/2011 | Lin |
| 2011/0251478 A1 | 10/2011 | Wieczorek |
| 2011/0255845 A1 | 10/2011 | Kikuchi |
| 2011/0257566 A1 | 10/2011 | Burdea |
| 2011/0260965 A1 | 10/2011 | Kim |
| 2011/0262002 A1 | 10/2011 | Lee |
| 2011/0267427 A1 | 11/2011 | Goh |
| 2011/0267456 A1 | 11/2011 | Adermann |
| 2011/0275957 A1 | 11/2011 | Bhandari |
| 2011/0276396 A1 | 11/2011 | Rathod |
| 2011/0279663 A1 | 11/2011 | Fan |
| 2011/0285622 A1 | 11/2011 | Marti |
| 2011/0286010 A1 | 11/2011 | Kusik et al. |
| 2011/0291925 A1 | 12/2011 | Israel |
| 2011/0293143 A1 | 12/2011 | Narayanan et al. |
| 2011/0293146 A1 | 12/2011 | Grycewicz |
| 2011/0298708 A1 | 12/2011 | Hsu |
| 2011/0298824 A1 | 12/2011 | Lee |
| 2011/0300994 A1 | 12/2011 | Verkaaik |
| 2011/0301449 A1 | 12/2011 | Maurer, Jr. |
| 2011/0301934 A1 | 12/2011 | Tardif |
| 2011/0303214 A1 | 12/2011 | Welle |
| 2011/0304541 A1 | 12/2011 | Dalal |
| 2011/0304650 A1 | 12/2011 | Canpillo |
| 2011/0304706 A1 | 12/2011 | Border et al. |
| 2011/0306867 A1 | 12/2011 | Gopinadhan |
| 2011/0310220 A1 | 12/2011 | McEldowney |
| 2011/0310226 A1 | 12/2011 | McEldowney |
| 2011/0316994 A1 | 12/2011 | Lemchen |
| 2011/0317877 A1 | 12/2011 | Bell |
| 2012/0002112 A1 | 1/2012 | Huang |
| 2012/0004791 A1 | 1/2012 | Buelthoff |
| 2012/0007839 A1 | 1/2012 | Tsao et al. |
| 2012/0019645 A1 | 1/2012 | Maltz |
| 2012/0020524 A1 | 1/2012 | Ishikawa |
| 2012/0021806 A1 | 1/2012 | Naltz |
| 2012/0027226 A1 | 2/2012 | Desenberg |
| 2012/0029345 A1 | 2/2012 | Mahfouz et al. |
| 2012/0032882 A1 | 2/2012 | Schlachta |
| 2012/0033083 A1 | 2/2012 | Horbinger |
| 2012/0035462 A1 | 2/2012 | Maurer, Jr. et al. |
| 2012/0039505 A1 | 2/2012 | Vastide |
| 2012/0044363 A1 | 2/2012 | Lu |
| 2012/0045091 A1 | 2/2012 | Kaganovich |
| 2012/0049453 A1 | 3/2012 | Morichau-Beauchant |
| 2012/0051588 A1 | 3/2012 | McEldowney |
| 2012/0051664 A1 | 3/2012 | Gopalakrishnan et al. |
| 2012/0052949 A1 | 3/2012 | Weitzner |
| 2012/0056982 A1 | 3/2012 | Katz |
| 2012/0057640 A1 | 3/2012 | Shi |
| 2012/0065492 A1 | 3/2012 | Gertner et al. |
| 2012/0065494 A1 | 3/2012 | Gertner et al. |
| 2012/0072041 A1 | 3/2012 | Miller |
| 2012/0075166 A1 | 3/2012 | Marti |
| 2012/0075177 A1 | 3/2012 | Jacobsen |
| 2012/0076369 A1 | 3/2012 | Abramovich |
| 2012/0081504 A1 | 4/2012 | Ng |
| 2012/0083314 A1 | 4/2012 | Ng |
| 2012/0083960 A1 | 4/2012 | Zhu |
| 2012/0086778 A1 | 4/2012 | Lee |
| 2012/0086809 A1 | 4/2012 | Lee |
| 2012/0092445 A1 | 4/2012 | McDowell |
| 2012/0092502 A1 | 4/2012 | Knasel |
| 2012/0093481 A1 | 4/2012 | McDowell |
| 2012/0098938 A1 | 4/2012 | Jin |
| 2012/0101388 A1 | 4/2012 | Tripathi |
| 2012/0105573 A1 | 5/2012 | Apostolopoulos |
| 2012/0106814 A1 | 5/2012 | Gleason et al. |
| 2012/0108909 A1 | 5/2012 | Slobounov et al. |
| 2012/0113140 A1 | 5/2012 | Hilliges |
| 2012/0113223 A1 | 5/2012 | Hilliges |
| 2012/0116202 A1 | 5/2012 | Bangera |
| 2012/0119999 A1 | 5/2012 | Harris |
| 2012/0120072 A1 | 5/2012 | Se |
| 2012/0120237 A1 | 5/2012 | Trepess |
| 2012/0120243 A1 | 5/2012 | Chien |
| 2012/0120277 A1 | 5/2012 | Tsai |
| 2012/0121124 A1 | 5/2012 | Bammer |
| 2012/0124604 A1 | 5/2012 | Small |
| 2012/0127319 A1 | 5/2012 | Rao |

(56) References Cited

U.S. PATENT DOCUMENTS

| | | |
|---|---|---|
| 2012/0133616 A1 | 5/2012 | Nishihara |
| 2012/0133889 A1 | 5/2012 | Bergt |
| 2012/0143029 A1 | 6/2012 | Silverstein |
| 2012/0143212 A1 | 6/2012 | Madhani |
| 2012/0154272 A1 | 6/2012 | Hildreth |
| 2012/0154511 A1 | 6/2012 | Hsu |
| 2012/0154536 A1 | 6/2012 | Stoker |
| 2012/0154579 A1 | 6/2012 | Hanpapur |
| 2012/0156661 A1 | 6/2012 | Smith |
| 2012/0158197 A1 | 6/2012 | Hinman |
| 2012/0162378 A1 | 6/2012 | El Dokor |
| 2012/0165964 A1 | 6/2012 | Flaks |
| 2012/0167143 A1 | 6/2012 | Longet |
| 2012/0169841 A1 | 7/2012 | Chemali |
| 2012/0176314 A1 | 7/2012 | Jeon |
| 2012/0184371 A1 | 7/2012 | Shum |
| 2012/0188237 A1 | 7/2012 | Han |
| 2012/0188371 A1 | 7/2012 | Chen |
| 2012/0194422 A1 | 8/2012 | El Dokor |
| 2012/0194517 A1 | 8/2012 | Ivadi |
| 2012/0194561 A1 | 8/2012 | Grossinger |
| 2012/0195466 A1 | 8/2012 | Teng |
| 2012/0196660 A1 | 8/2012 | Eo Dokor |
| 2012/0197135 A1 | 8/2012 | Slatkine |
| 2012/0200676 A1 | 8/2012 | Huitema |
| 2012/0201428 A1 | 8/2012 | Joshi et al. |
| 2012/0206604 A1 | 8/2012 | Jones |
| 2012/0212594 A1 | 8/2012 | Barnes |
| 2012/0218407 A1 | 8/2012 | Chien |
| 2012/0218421 A1 | 8/2012 | Chien |
| 2012/0220233 A1 | 8/2012 | Teague |
| 2012/0224666 A1 | 9/2012 | Speller |
| 2012/0224743 A1 | 9/2012 | Rodriguez |
| 2012/0225718 A1 | 9/2012 | Zhang |
| 2012/0229643 A1 | 9/2012 | Chidanand |
| 2012/0229651 A1 | 9/2012 | Takizawa |
| 2012/0230561 A1 | 9/2012 | Qureshi |
| 2012/0235896 A1 | 9/2012 | Jacobsen |
| 2012/0238337 A1 | 9/2012 | French |
| 2012/0242816 A1 | 9/2012 | Cruz |
| 2012/0249741 A1 | 10/2012 | Maciocci |
| 2012/0253201 A1 | 10/2012 | Reinhold |
| 2012/0253241 A1 | 10/2012 | Ludital |
| 2012/0262540 A1 | 10/2012 | Rondinelli |
| 2012/0262558 A1 | 10/2012 | Boger |
| 2012/0262583 A1 | 10/2012 | Bernal |
| 2012/0268124 A1 | 10/2012 | Herbst et al. |
| 2012/0275649 A1 | 11/2012 | Cobb |
| 2012/0276995 A1 | 11/2012 | Lansdale |
| 2012/0277001 A1 | 11/2012 | Lansdale |
| 2012/0281093 A1 | 11/2012 | Fong |
| 2012/0281873 A1 | 11/2012 | Brown |
| 2012/0288142 A1 | 11/2012 | Gossweiler, III |
| 2012/0288143 A1 | 11/2012 | Ernst |
| 2012/0288852 A1 | 11/2012 | Willson |
| 2012/0289334 A9 | 11/2012 | Mikhailov |
| 2012/0289822 A1 | 11/2012 | Shachar et al. |
| 2012/0293412 A1 | 11/2012 | El Dokor |
| 2012/0293506 A1 | 11/2012 | Vertucci |
| 2012/0293663 A1 | 11/2012 | Liu |
| 2012/0294511 A1 | 11/2012 | Datta |
| 2012/0300961 A1 | 11/2012 | Moeller |
| 2012/0303839 A1 | 11/2012 | Jackson |
| 2012/0304126 A1 | 11/2012 | Lavigne |
| 2012/0307075 A1 | 12/2012 | Nargalit |
| 2012/0307207 A1 | 12/2012 | Abraham |
| 2012/0314066 A1 | 12/2012 | Lee |
| 2012/0315016 A1 | 12/2012 | Fung |
| 2012/0319946 A1 | 12/2012 | El Dokor |
| 2012/0319989 A1 | 12/2012 | Argiro |
| 2012/0320178 A1 | 12/2012 | Siegert et al. |
| 2012/0320219 A1 | 12/2012 | David |
| 2012/0326966 A1 | 12/2012 | Rauber |
| 2012/0326976 A1 | 12/2012 | Markovic |
| 2012/0326979 A1 | 12/2012 | Geisert |
| 2012/0327241 A1 | 12/2012 | Howe |
| 2012/0327246 A1 | 12/2012 | Senior et al. |
| 2013/0002866 A1 | 1/2013 | Hanpapur |
| 2013/0002879 A1 | 1/2013 | Weber |
| 2013/0002900 A1 | 1/2013 | Gossweiler, III |
| 2013/0009865 A1 | 1/2013 | Valik |
| 2013/0010071 A1 | 1/2013 | Valik |
| 2013/0013452 A1 | 1/2013 | Dennard |
| 2013/0016009 A1 | 1/2013 | Godfrey |
| 2013/0016876 A1 | 1/2013 | Wooley |
| 2013/0021434 A1 | 1/2013 | Ahiska |
| 2013/0021578 A1 | 1/2013 | Chen |
| 2013/0024819 A1 | 1/2013 | Rieffel |
| 2013/0030283 A1 | 1/2013 | Vortman et al. |
| 2013/0033640 A1 | 2/2013 | Lee |
| 2013/0033700 A1 | 2/2013 | Hallil |
| 2013/0035590 A1 | 2/2013 | Ma et al. |
| 2013/0035612 A1 | 2/2013 | Mason |
| 2013/0040720 A1 | 2/2013 | Cammegh |
| 2013/0041368 A1 | 2/2013 | Cunninghan |
| 2013/0049756 A1 | 2/2013 | Ernst et al. |
| 2013/0057702 A1 | 3/2013 | Chavan |
| 2013/0064426 A1 | 3/2013 | Watkins, Jr. |
| 2013/0064427 A1 | 3/2013 | Picard |
| 2013/0065517 A1 | 3/2013 | Svensson |
| 2013/0066448 A1 | 3/2013 | Alonso |
| 2013/0066526 A1 | 3/2013 | Mondragon |
| 2013/0069773 A1 | 3/2013 | Li |
| 2013/0070201 A1 | 3/2013 | Shahidi |
| 2013/0070257 A1 | 3/2013 | Wong |
| 2013/0072787 A1 | 3/2013 | Wallace et al. |
| 2013/0076863 A1 | 3/2013 | Rappel |
| 2013/0076944 A1 | 3/2013 | Kosaka |
| 2013/0077823 A1 | 3/2013 | Mestha |
| 2013/0079033 A1 | 3/2013 | Gupta |
| 2013/0084980 A1 | 4/2013 | Hammontree |
| 2013/0088584 A1 | 4/2013 | Malhas |
| 2013/0093866 A1 | 4/2013 | Ohlhues et al. |
| 2013/0096439 A1 | 4/2013 | Lee |
| 2013/0102879 A1 | 4/2013 | MacLaren et al. |
| 2013/0102893 A1* | 4/2013 | Vollmer ............... A61B 5/0062 600/424 |
| 2013/0108979 A1 | 5/2013 | Daon |
| 2013/0113791 A1 | 5/2013 | Isaacs et al. |
| 2013/0211421 A1 | 8/2013 | Abovitz et al. |
| 2013/0281818 A1 | 10/2013 | Vija et al. |
| 2014/0037174 A1 | 2/2014 | Ernst et al. |
| 2014/0073908 A1 | 3/2014 | Biber |
| 2014/0088410 A1 | 3/2014 | Wu |
| 2014/0148685 A1 | 5/2014 | Liu et al. |
| 2014/0159721 A1 | 6/2014 | Grodzki |
| 2014/0171784 A1 | 6/2014 | Ooi et al. |
| 2014/0205140 A1 | 7/2014 | Lovberg et al. |
| 2014/0378816 A1 | 12/2014 | Oh et al. |
| 2015/0085072 A1 | 3/2015 | Yan |
| 2015/0265220 A1 | 9/2015 | Ernst et al. |
| 2015/0297120 A1 | 10/2015 | Son et al. |
| 2015/0331078 A1 | 11/2015 | Speck et al. |
| 2015/0359464 A1* | 12/2015 | Olesen ............... A61B 5/721 600/476 |
| 2015/0366527 A1 | 12/2015 | Yu et al. |
| 2016/0035108 A1 | 2/2016 | Yu et al. |
| 2016/0073962 A1 | 3/2016 | Yu et al. |
| 2016/0091592 A1 | 3/2016 | Beall et al. |
| 2016/0166205 A1 | 6/2016 | Ernst et al. |
| 2016/0189372 A1 | 6/2016 | Lovberg et al. |
| 2016/0228005 A1 | 8/2016 | Bammer et al. |
| 2016/0249984 A1 | 9/2016 | Janssen |
| 2016/0256713 A1 | 9/2016 | Saunders et al. |
| 2016/0262663 A1 | 9/2016 | MacLaren et al. |
| 2016/0287080 A1 | 10/2016 | Olesen et al. |
| 2016/0310229 A1 | 10/2016 | Bammer et al. |
| 2016/0313432 A1 | 10/2016 | Feiweier et al. |
| 2017/0032538 A1 | 2/2017 | Ernst |

FOREIGN PATENT DOCUMENTS

| | | |
|---|---|---|
| DE | 29519078 | 3/1996 |
| DE | 102004024470 | 12/2005 |

(56) References Cited

FOREIGN PATENT DOCUMENTS

| | | |
|---|---|---|
| EP | 1354564 | 10/2003 |
| EP | 1524626 A2 | 4/2005 |
| EP | 2515139 | 10/2012 |
| EP | 2948056 | 12/2015 |
| EP | 2950714 | 12/2015 |
| JP | 03023838 | 5/1991 |
| WO | WO 96/17258 A2 | 6/1996 |
| WO | WO 99/38449 | 8/1999 |
| WO | WO 00/72039 A1 | 11/2000 |
| WO | WO 03/003796 A1 | 1/2003 |
| WO | WO 2004/023783 A2 | 3/2004 |
| WO | WO 2005/077293 | 8/2005 |
| WO | WO 2007/025301 | 3/2007 |
| WO | WO 2007/085241 A1 | 8/2007 |
| WO | WO 2007/136745 | 11/2007 |
| WO | WO 2009/101566 | 8/2009 |
| WO | WO 2009/129457 A1 | 10/2009 |
| WO | WO 2011/047467 A1 | 4/2011 |
| WO | WO 2011/113441 A2 | 9/2011 |
| WO | WO 2012/046202 A1 | 4/2012 |
| WO | WO 2013/032933 | 3/2013 |
| WO | WO 2014/005178 | 1/2014 |
| WO | WO 2014/116868 | 7/2014 |
| WO | WO 2014/120734 | 8/2014 |
| WO | WO 2015/042138 | 3/2015 |
| WO | WO 2015/092593 | 6/2015 |
| WO | WO 2015/148391 | 10/2015 |
| WO | WO 2016/014718 | 1/2016 |

OTHER PUBLICATIONS

Anishenko et al. "A Motion Correction System for Brain Tomography Based on Biologically Motivated Models." 7th IEEE International Conference on Cybernetic Intelligent Systems, Sep. 9, 2008, 9 pages.*
Aksoy et al., "Hybrind Prospective and Retrospective Head Motion Correction to Mitigate Cross-Calibration Errors", NIH Publication, Nov. 2012.
Aksoy et al., "Real-Time Optical Motion Correction for Diffusion Tensor Imaging, Magnetic Resonance in Medicine" (Mar. 22, 2011) 66 366-378.
Andrews et al., "Prospective Motion Correction for Magnetic Resonance Spectroscopy Using Single Camera Retro-Grate Reflector Optical Tracking, Journal of Magnetic Resonance Imaging" (Feb. 2011) 33(2): 498-504.
Angeles et al., "The Online Solution of the Hand-Eye Problem", IEEE Transactions on Robotics and Automation, 16(6): 720-731 (Dec. 2000).
Bandettini, Peter A., et al., "Processing Strategies for Time-Course Data Sets in Functional MRI of the Human Breain", Magnetic Resonance in Medicine 30: 161-173 (1993).
Barmet et al, Spatiotemporal Magnetic Field Monitoring for MR, Magnetic Resonance in Medicine (Feb. 1, 2008) 60: 187-197.
Bartels, LW, et al., "Endovascular interventional magnetic resonance imaging", Physics in Medicine and Biology 48: R37-R64 (2003).
Carranza-Herrezuelo et al, "Motion estimation of tagged cardiac magnetic resonance images using variational techniques" Elsevier, Computerized Medical Imaging and Graphics 34 (2010), pp. 514-522.
Chou, Jack C. K., et al., "Finding the Position and Orientation of a Sensor on a Robot Manipulator Using Quaternions", The International Journal of Robotics Research, 10(3): 240-254 (Jun. 1991).
Cofaru et al "Improved Newton-Raphson digital image correlation method for full-field displacement and strain calculation," Department of Materials Science and Engineering, Ghent University St-Pietersnieuwstraat, Nov. 20, 2010.
Ernst et al., "A Novel Phase and Frequency Navigator for Proton Magnetic Resonance Spectroscopy Using Water-Suppression Cycling, Magnetic Resonance in Medicine" (Jan. 2011) 65(1): 13-7.

Eviatar et al., "Real time head motion correction for functional MRI", In: Proceedings of the International Society for Magnetic Resonance in Medicine (1999) 269.
Forbes, Kristen P. N., et al., "Propeller MRI: Clinical Testing of a Novel Technique for Quantification and Compensation of Head Motion", Journal of Magnetic Resonance Imaging 14: 215-222 (2001).
Glover, Gary H., et al., "Self-Navigated Spiral fMRI: Interleaved versus Single-shot", Magnetic Resonance in Medicine 39: 361-368 (1998).
Gumus et al., "Elimination of DWI signal dropouts using blipped gradients for dynamic restoration of gradient moment", ISMRM 20th Annual Meeting & Exhibition, May 7, 2012.
Herbst et al., "Preventing Signal Dropouts in DWI Using Continous Prospective Motion Correction", Proc. Intl. Soc. Mag. Reson. Med. 19 (May 2011) 170.
Herbst et al., "Prospective Motion Correction With Continuous Gradient Updates in Diffusion Weighted Imaging, Magnetic Resonance in Medicine" (2012) 67:326-338.
Horn, Berthold K. P., "Closed-form solution of absolute orientation using unit quaternions", Journal of the Optical Society of America, vol. 4, p. 629-642 (Apr. 1987).
International Preliminary Report on Patentability for Application No. PCT/US2007/011899, dated Jun. 8, 2008, in 13 pages.
International Search Report and Written Opinion for Application No. PCT/US2007/011899, dated Nov. 14, 2007.
International Search Report and Written Opinion for Application No. PCT/US2014/012806, dated May 15, 2014, in 15 pages.
International Search Report and Written Opinion for Application No. PCT/US2014/013546, dated May 26, 2014, in 14 pages.
International Preliminary Report on Patentability for Application No. PCT/US2014/013546, dated Aug. 4, 2015, in 9 pages.
International Search Report and Written Opinion for Application No. PCT/US2015/022041, dated Jun. 29, 2015, in 9 pages.
Josefsson et al. "A flexible high-precision video system for digital recording of motor acts through lightweight reflect markers", Computer Methods and Programs in Biomedicine, vol. 49:111-129 (1996).
Kiruluta et al., "Predictive Head Movement Tracking Using a Kalman Filter", IEEE Trans. on Systems, Man, and Cybernetics—Part B: Cybernetics, 27(2):326-331 (Apr. 1997).
Maclaren et al., "Combined Prospective and Retrospective Motion Correction to Relax Navigator Requirements", Magnetic Resonance in Medicine (Feb. 11, 2011) 65:1724-1732.
MacLaren et al., "Navigator Accuracy Requirements for Prospective Motion Correction", Magnetic Resonance in Medicine (Jan. 2010) 63(1): 162-70.
MacLaren, "Prospective Motion Correction in MRI Using Optical Tracking Tape", Book of Abstracts, ESMRMB (2009).
Maclaren et al., "Measurement and correction of microscopic head motion during magnetic resonance imaging of the brain", PLOS ONE, vol. 7(11):1-9 (2012).
McVeigh et al., "Real-time, Interactive MRI for Cardiovascular Interventions", Academic Radiology, 12(9): 1121-1127 (2005).
Nehrke et al., "Prospective Correction of Affine Motion for Arbitrary MR Sequences on a Clinical Scanner", Magnetic Resonance in Medicine (Jun. 28, 2005) 54:1130-1138.
Norris et al., "Online motion correction for diffusion-weighted imaging using navigator echoes: application to RARE imaging without sensitivity loss", Magnetic Resonance in Medicine, vol. 45:729-733 (2001).
Ooi et al., "Prospective Real-Time Correction for Arbitrary Head Motion Using Active Markers", Magnetic Resonance in Medicine (Apr. 15, 2009) 62(4): 943-54.
Orchard et al., "MRI Reconstruction using real-time motion tracking: A simulation study", Signals, Systems and Computers, 42nd Annual Conference IEEE, Piscataway, NJ, USA (Oct. 26, 2008).
Park, Frank C. and Martin, Bryan J., "Robot Sensor Calibration: Solving AX-XB on the Euclidean Group", IEEE Transaction on Robotics and Automation, 10(5): 717-721 (Oct. 1994).
PCT Search Report from the International Searching Authority, dated Feb. 28, 2013, in 16 pages, regarding International Application No. PCT/US2012/052349.

(56) References Cited

OTHER PUBLICATIONS

Qin et al., "Prospective Head-Movement Correction for High-Resolution MRI Using an In-Bore Optical Tracking System", Magnetic Resonance in Medicine (Apr. 13, 2009) 62: 924-934.
Schulz et al., "First Embedded In-Bore System for Fast Optical Prospective Head Motion-Correction in MRI", Proceedings of the 28th Annual Scientific Meeting of the ESMRMB (Oct. 8, 2011) 369.
Shiu et al., "Calibration of Wrist-Mounted Robotic Sensors by Solving Homogeneous Transform Equations of the Form AX=XB", IEEE Transactions on Robotics and Automation, 5(1): 16-29 (Feb. 1989).
Tremblay et al., "Retrospective Coregistration of Functional Magnetic Resonance Imaging Data using External monitoring", Magnetic Resonance in Medicine 53:141-149 (2005).
Tsai et al., "A New Technique for Fully Autonomous and Efficient 3D Robotics Hand/Eye Calibration", IEEE Transaction on Robotics and Automation, 5(3): 345-358 (Jun. 1989).
Wang, Ching-Cheng, "Extrinsic Calibration of a Vision Sensor Mounted on a Robot", IEEE Transactions on Robotics and Automation, 8(2):161-175 (Apr. 1992).
Ward et al., "Prospective Multiaxial Motion Correction for fMRI", Magnetic Resonance in Medicine 43:459-469 (2000).
Welch at al., "Spherical Navigator Echoes for Full 3D Rigid Body Motion Measurement in MRI", Magnetic Resonance in Medicine 47:32-41 (2002).
Zaitsev, M., et al., "Prospective Real-Time Slice-by-Slice 3D Motion Correction for EPI Using an External Optical Motion Tracking System", Proc.Intl.Soc.Mag.Reson.Med.11:517(2004).
Zeitsev et al., "Magnetic resonance imaging of freely moving objects: Prospective real-time motion correction using an external optical motion tracking system", NeuroImage 31 (Jan. 29, 2006) 1038-1050.
Armstrong et al., RGR-6D: Low-cost, high-accuracy measurement of 6-DOF Pose from a Single Image. Publication date unknown.
Armstrong et al., "RGR-3D: Simple, cheap detection of 6-DOF pose for tele-operation, and robot programming and calibration", In Proc. 2002 Int. Conf. on Robotics and Automation, IEEE, Washington (May 2002).
Fulton et al., "Correction for Head Movements in Positron Emission Tomography Using an Optical Motion-Tracking System", IEEE Transactions on Nuclear Science, vol. 49(1):116-123 (Feb. 2002).
Hoff et al., "Analysis of Head Pose Accuracy in Augmented Reality", IEEE Transactions on Visualization and Computer Graphics 6, No. 4 (Oct.-Dec. 2000): 319-334.
International Preliminary Report on Patentability for Application No. PCT/US2015/022041, dated Oct. 6, 2016, in 8 pages.
International Search Report and Written Opinion for Application No. PCT/US2015/041615, dated Oct. 29, 2015, in 13 pages.
Katsuki, et al., "Design of an Artificial Mark to Determine 3D Pose by Monocular Vision", 2003 IEEE International Conference on Robotics and Automation (Cat. No. 03CH37422), Sep. 14-19, 2003, pp. 995-1000 vol. 1.
Kiebel et al., "MRI and PET coregistration—a cross validation of statistical parametric mapping and automated image registration", Neuroimage 5(4):271-279 (1997).
Lerner, "Motion correction in fmri images", Technion-lsrael Institute of Technology, Faculty of Computer Science ( Feb. 2006).
Speck, et al., "Prospective real-time slice-by-slice Motion Correction for fMRI in Freely Moving Subjects", Magnetic Resonance Materials in Physics, Biology and Medicine., 19(2), 55-61, published May 9, 2006.
Yeo, et al. Motion correction in fMRI by mapping slice-to-volume with concurrent field-inhomogeneity correction:, International Conference on Medical Image Computing and Computer-Assisted Intervention, pp. 752-760 (2004).

\* cited by examiner

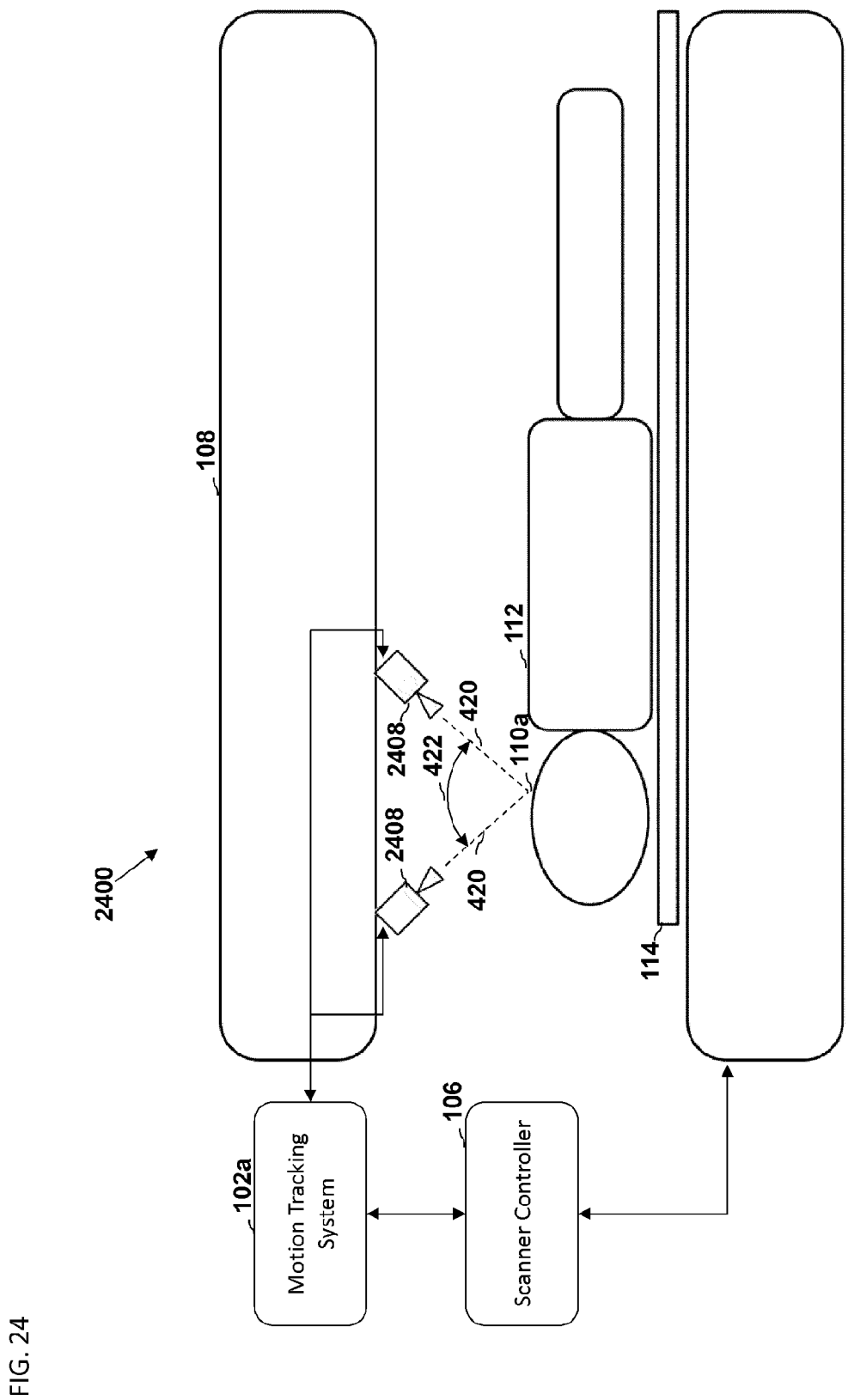

MOTION TRACKING SYSTEM FOR REAL TIME ADAPTIVE MOTION COMPENSATION IN BIOMEDICAL IMAGING

INCORPORATION BY REFERENCE TO RELATED APPLICATIONS

The present application is a PCT Application that claims the benefit of U.S. Provisional Patent Application No. 61/759,883, titled MOTION TRACKING SYSTEM FOR REAL TIME ADAPTIVE MOTION COMPENSATION IN BIOMEDICAL IMAGING, filed on Feb. 1, 2013, which is hereby incorporated herein by reference in its entirety.

STATEMENT REGARDING FEDERALLY SPONSORED R&D

This invention was made with government support under grant number R01DA021146-01A1 awarded by the National Institutes of Health. The government has certain rights in the invention.

BACKGROUND

Field

The disclosure relates generally to the field of biomedical imaging machines, and more specifically to a system for adaptive motion correction of medical imaging scans, such as magnetic resonance scans.

Description of the Related Art

"Tomographic" imaging techniques generate images of multiple slices of an object. Some commonly used tomographic imaging techniques include but are not limited to magnetic resonance imaging (MRI) and magnetic resonance spectroscopy (MRS) techniques, which are ideal for assessing the structure, physiology, chemistry and function of the living brain and other organs, in vivo and non-invasively. Because the object of interest is often imaged in many scanning steps in order to build a complete two or three dimensional view, scans are of long duration, usually lasting several minutes or more. To increase resolution (detail) of a tomographic scan, more slices and more scanning steps must be used, which further increases the duration of a scan. Scans may also be of long duration in order to obtain sufficient signal-to-noise ratio. Magnetic resonance techniques (including tomographic techniques), that are currently known or to be developed in the future (hereinafter collectively referred to as "MR" or "MRI") can also afford relatively high spatial and temporal resolution, are non-invasive and repeatable, and may be performed in children and infants. However, due to their duration, MR scans can be subject to the problem of patient or object motion.

SUMMARY OF THE INVENTION

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In an embodiment, a biomedical system for tracking motion of an object during biomedical imaging and for compensating for motion of the object comprises a biomedical imaging scanner configured to perform scanning of the object to generate biomedical images of the object; at least one detector for generating data describing at least one landmark of the object, wherein the at least one detector is configured to be positioned relative to the object to enable the at least one detector to detect movement of said landmark during the scanning; a detector processing interface configured to determine motion of the object based on analyzing said data received from the at least one detector, the detector processing interface configured to generate motion tracking data of the object; and a scanner controller for controlling at least one parameter of the biomedical imaging scanner, wherein the scanner controller is configured to adjust scanner parameters based on the motion tracking data, the scanner parameters configured for controlling the biomedical imaging scanner to account for motion of the object during the scanning of the object.

In an embodiment, the at least one detector is positioned within a bore of the biomedical imaging scanner. In an embodiment, the at least one detector only comprises components configured to not interfere with the biomedical imaging scanner. In an embodiment the at least one landmark comprises a facial feature of the subject. In an embodiment, the facial feature comprises at least one tooth of the upper jawbone. In an embodiment, the landmark comprises an organ of the subject. In an embodiment, the at least one landmark comprises an image projected onto the subject. In an embodiment, the at least one detector processing interface is configured to utilize an atlas-segmentation technique for identifying the at least one landmark of the object.

In an embodiment, the at least one detector is configured to generate data describing a first landmark and a second landmark of the object, wherein the detector processing interface is configured to utilize a first motion tracking technique to determine motion of the first landmark, and a second motion tracking technique to determine the motion of the second landmark, the detector processing interface configured to determine motion of the object based on analyzing the determined motion of the first landmark and the second landmark. In an embodiment, the detector processing interface is configured to apply a first weighting factor to the determined motion of the first landmark and apply a second weighting factor to the determined motion of the second landmark, wherein the first weighting factor is based on a historical accuracy of the first motion tracking technique and the second weighting factor is based on a historical accuracy of the second motion tracking technique.

In an embodiment, a computer implemented-method for tracking motion of an object during biomedical imaging by a scanner and for compensating for motion of the object comprises accessing, by a computer system, an image of the object; identifying, by the computer system, in the image a landmark of the object, the landmark being a feature naturally existing in the object; accessing, by the computer system, a plurality of images of the object; tracking, by the computer system, movement of the landmark in the plurality of images of the object; translating, by the computer system, the movement in a first reference plane to a second reference plane of the scanner; generating, by the computer system, data parameters based on the movement in the second reference plane, the data parameters configured to adjust the scanning parameters of the scanner to account for motion of the object; and transmitting, by the computer system, the data parameters to a scanner controller, the scanner controller configured to control the scanning parameters of the scanner.

In an embodiment, the image is from a video. In an embodiment, the accessing of the image of the object is from at least one detector that is positioned within a bore of the scanner. In an embodiment, the at least one detector only comprises components configured to not interfere with the scanner. In an embodiment, the landmark comprises a facial feature. In an embodiment, the facial feature comprises at least one tooth of the upper jawbone. In an embodiment, the landmark comprises an organ. In an embodiment, the identifying comprises utilizing an atlas-segmentation technique for identifying the landmark of the object.

In an embodiment, the computer-implemented method further comprises identifying, by the computer system, in the image a second landmark, the identifying of the landmark performed by utilizing a first motion tracking technique to determine motion of the landmark, and the identifying of the second landmark performed by utilizing a second motion tracking technique to determine the motion of the second landmark, the tracking comprises determining the movement of the landmark and the second landmark in the plurality of images of the object, wherein the movement is an average of the motion of the landmark and the motion of the second landmark. In an embodiment, the movement is determined by applying a first weighting factor to the determined motion of the landmark to generate a first weighted motion, and applying a second weighting factor to the determined motion of the second landmark to generate a second weighted motion, and averaging the first and second weighted motions, wherein the first weighting factor is based on a historical accuracy of the first motion tracking technique and the second weighting factor is based on a historical accuracy of the second motion tracking technique.

BRIEF DESCRIPTION OF THE DRAWINGS

The foregoing and other features, aspects, and advantages of the present invention are described in detail below with reference to the drawings of various embodiments, which are intended to illustrate and not to limit the invention. The drawings comprise the following figures in which:

FIG. 24 is a schematic diagram illustrating a side view of the medical imaging scanner as a part of the motion compensation system.

DETAILED DESCRIPTION OF THE EMBODIMENTS

Figure 1:
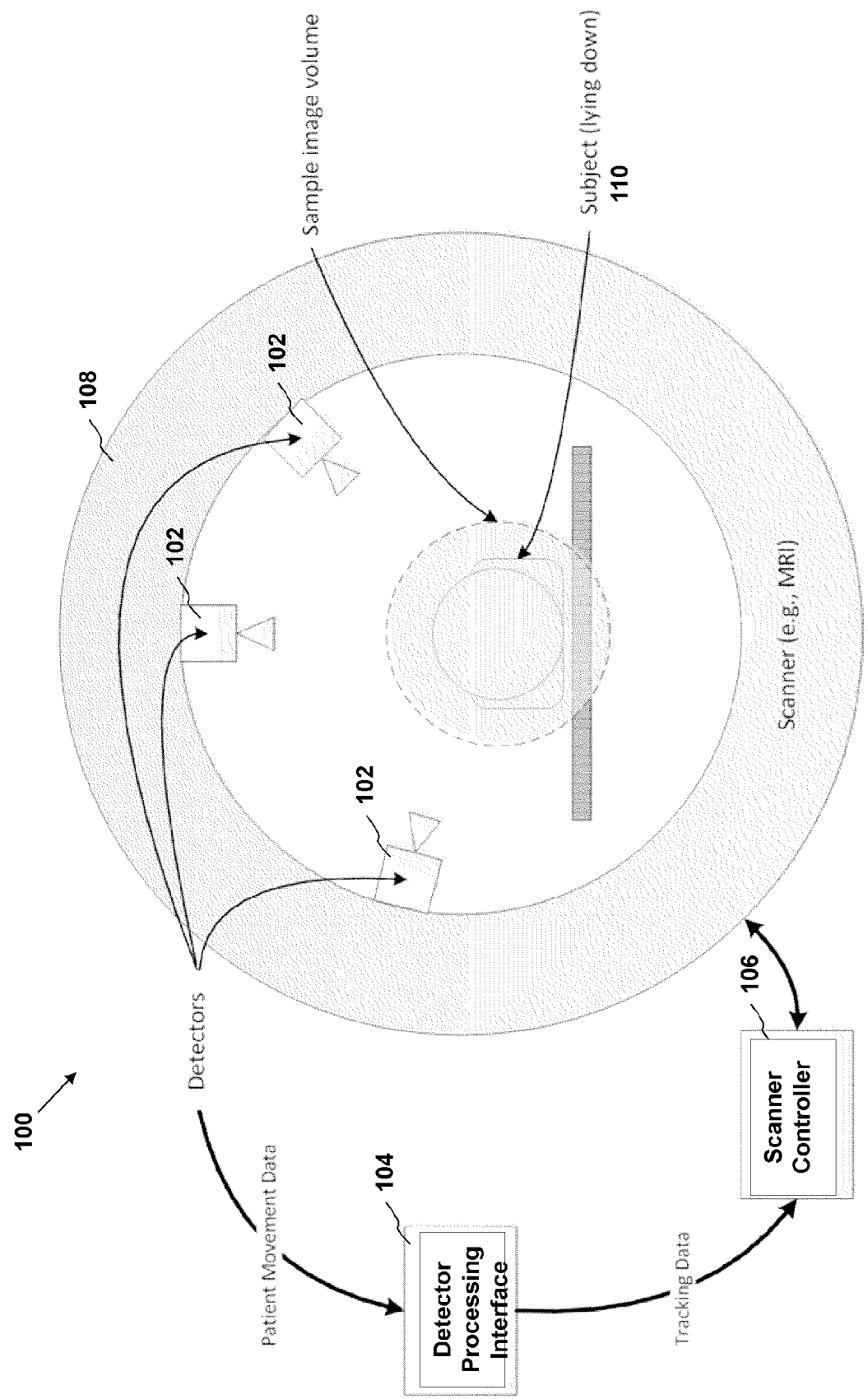
FIG. 1 is an embodiment of a schematic diagram illustrating a motion tracking system for a biomedical imaging machine.

Although several embodiments, examples, and illustrations are disclosed below, it will be understood by those of ordinary skill in the art that the invention described herein extends beyond the specifically disclosed embodiments, examples, and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

The disclosure herein provides methods, systems, and devices for tracking motion of a patient or object of interest during biomedical imaging and for compensating for the patient motion by adjusting the imaging parameters of the biomedical imaging scanner and/or the resulting images to reduce or eliminate motion artifacts. In an embodiment, one or more detectors are configured to detect images of or signals reflected from or spatial information of a patient, and a detector processing interface is configured to analyze the images or signals or spatial information to estimate motion or movement of the patient and to generate tracking data describing the patient's motion. The detector processing interface is configured to send the tracking data to a scanner controller to enable adjustment of scanning parameters in real-time in response to the patient's motion.

In order to assess the structure, physiology, chemistry and function of the human brain or other organs, physicians may employ any number of tomographic medical imaging techniques. Some of the more commonly used tomographic imaging techniques include computerized tomography (CT), magnetic resonance imaging (MRI), magnetic resonance spectroscopy (MRS), positron emission tomography (PET), and single-photon emission computed tomography (SPECT). These techniques take a series of images that correspond to individual slices of the object of interest (for example, the brain), and use computer algorithms to align and assemble the slice images into three dimensional views. Because the object of interest is often imaged in many slices and scanning steps, the resulting scan time can be relatively long, typically lasting several minutes or longer.

Biomedical imaging techniques with long scan times can tend to be sensitive to subject motion, which can lead to image artifacts and/or loss of resolution. Due to the typical duration of a tomographic imaging scan, subject motion can become a significant obstacle to acquiring accurate or clear image data. Although subjects are typically instructed to remain still during a scan, remaining motionless is a near impossible task for many patients, especially infants, children, the elderly, animals, patients with movement disorders, and other patients who might be agitated or cannot control body movements due to, for example, disability, impairment, injury, severe sickness, anxiety, nervousness, drug use, or other disorder. Often, the resulting scans of such patients are obscured by significant motion artifacts, making adequate diagnosis and analysis difficult.

One method to reduce motion artifacts is to use physical restraints to prevent subject movement. Such restraints, however, can be difficult to employ due to both the limited space within the scanning volume of the tomographic imager and the uncomfortable nature of the restraints themselves.

Another method to reduce motion artifacts involves tracking and adapting to subject movement in real time (for example, "adaptive imaging" or "adaptive motion correction"). This approach involves tracking the position and rotation (together referred to as "pose") of the object of interest in real time during a scan. The pose information is used to compensate for detected motion in subsequent data acquisitions. Although these techniques can have the benefit of being highly accurate, they can require periodic recalibration to maintain such accuracy. Additionally, some embodiments of motion tracking systems use one or more cameras to track the position of one or more markers attached to a subject or to an organ to be evaluated (such as the subject's head) to determine subject motion. However, the use of markers creates additional steps in the clinical workflow, which can be undesirable. Attachment of tracking markers may also not be accepted by certain subjects, such as young children, who may remove markers.

The systems, methods, and devices disclosed herein provide solutions to the foregoing problems as well as to other challenges related to biomedical imaging. Some embodiments disclosed herein provide systems for adaptive motion correction for biomedical imaging that do not require specialized removable markers for tracking (also referred to herein as "markerless" tracking or landmark tracking). In some embodiments, a motion tracking system includes a biomedical scanner, such as an MRI, CAT, PET, or other scanner, that uses tracking information from a markerless optical or non-optical tracking system to continuously adjust scanning parameters (such as scan planes, locations, and orientations) to result in biomedical images showing no or attenuated motion artifacts. In an embodiment, the tracking information is based on using detectors to track landmarks that are naturally existing on a subject, as opposed to attaching removable markers to a subject.

As used herein, the terms "landmark" and "feature", when used in the context of describing a quality or characteristic of a subject or object, are interchangeable terms and are broad terms, and unless otherwise indicated the terms can include within their meaning, without limitation, features of the subject (for example, facial features including but not limited to indentations, protrusions, folds, curves, outlines, moles, skin pigmentations, or the like), projected images or other projections onto a subject, distances to a point or area of a subject, surfaces of a subject (for example, three-dimensional surface modeling), openings or orifices of a subject, bones or bone structures of a subject (for example, teeth or cheek bones, or the like), and hair features of a subject (for example, hair lines, eye brows, or the like).

The term "detector" as used herein is a broad term, and unless otherwise indicated the term can include within its meaning, without limitation, a camera (either digital or analog, and either capable of capturing still images or movies) that can detect the visible spectrum or other portions of the electromagnetic spectrum, a proximity sensor, an ultrasonic sensor, a radar sensor, a laser-based sensors, or any other kind of detector. In embodiments where the detector is positioned within the bore of a medical imaging device, the term "detector" includes within its meaning a detector that is configured to not interfere or only comprises components that do not interfere with the imaging capability of the medical imaging device, for example, the detector does not generate electrical or magnetic interference that could cause artifacts in the images generated by the medical imaging device.

In an embodiment, the system can be configured to track subject motion using landmarks of a subject through a variety of ways. For example, the system can be configured for tracking different types of body organs or facial features or the like. For each type of body organ or other feature, the system can comprise an atlas or a normative database showing a typical shape of a particular body organ or feature. In an embodiment, the system can be configured to utilize the atlas in order to perform atlas-segmentation to identify an organ or feature within an image generated by a detector. Based on detection of the organ or feature, the system can be configured to track the movement of the organ or feature in subsequent images generated by the detector. In an embodiment, the system can be configured with a different detection algorithm and/or atlas for each type of body organ. For example, the system can be configured with a different detection algorithm for the head and a different detection algorithm for knee of the patient.

In another example, the system can be configured to identify one or more teeth of the upper jaw. The detection of one or more teeth of the upper jaw can be ideal for landmark-based motion tracking because the upper teeth are rigidly affixed the skull of a patient. Any movement of the skull translates into direct movement of the upper teeth. In contrast, the teeth on the lower jawbone are subject to movement not only due to movement of the skull, but also due to movement of the lower jawbone. As disclosed above, the system can be configured to utilize atlas-segmentation techniques in order to locate and identify the upper teeth in an image generated by a detector. Based on detection of the upper teeth, the system can be configured to track the movement of the upper teeth in subsequent images generated by the detector. In an embodiment, the system can be configured to utilize the motion tracking of the upper teeth to generate data instructions for transmission to the scanner in order to adjust the scanner parameters. By adjusting the scanner parameters, the system can be configured to account for patient movement during the scanning process in order to produce clearer or better images of the subject. In an embodiment, a mouth insert or a mouth guard is configured to expose the upper teeth can be inserted into a subject's mouth in order for the detector to generate images of the upper teeth during the scanning process. In an embodiment, the mouth insert or guard need not be customized for the subject's particular mouth. In an embodiment, the mouth insert or guard is a "one size fits all" mouth insert or guard that is configured to move the upper lip to an upward position in order to expose the upper teeth during the scanning process.

In an embodiment, the system can be configured to identify a characteristic of a subject. For example, the system can be configured to detect a distance to a particular point on a subject, or a surface texture of a subject, or an image that is projected onto the subject. Based on detecting the characteristic of a subject, the system can be configured to track the movement of the characteristic in subsequent images generated by the detector. In an embodiment, the system can be configured to track subject movement using a combination of any of the landmark tracking techniques disclosed above. Based on the tracked movements of the subject, the system can be configured to utilize the data in order to generate instructions for adjusting the parameters of a scanner in order to generate a better image.

In an embodiment, the detected motion that is determined by the system can be an estimated motion of the subject because the system can only detect the position of the subject at the time that the image of the subject was detected. Generally, subjects are continuously moving and therefore a subject may have moved after the time in which an image generated by the detector is being analyzed.

In an embodiment, the system can be configured to estimate the accuracy of a detected motion. For example, the system can be configured to track the movements of an eyebrow of a subject. If the system detects the location of an eyebrow in a first image and then the system cannot detect the location of an eyebrow in a second subsequent image, then the system can be configured to discount the second image because any motion tracking data generated based on the first and second image is likely to be in accurate. In an embodiment, the system can be configured to assume that the eyebrow was truncated in the second image, or that tracking of the eyebrow has been lost, and therefore the second image is not a reliable image for determining or tracking motion.

In an embodiment, a motion tracking system utilizes one or more detectors, such as cameras, to continuously record partial or full views of an object of interest. A detector processing interface continuously analyzes the patient movement data from the detectors to estimate motion of the object of interest. The detector processing interface can be configured to analyze and track motion using a variety of filters or techniques, either individually or in combination, including anatomical landmark tracking, three dimensional surface modeling, distance estimation, or other similar techniques.

In an embodiment, the detector processing interface can be configured to average the detected estimated motion that has been determined using the variety of techniques or filters. The detector processing interface can be configured to employ a weighted average in combining the detected estimated motion that has been determined using the variety of techniques of filters. In an embodiment, the detector processing interface can be configured to select the detected estimated motion values that are determined to be the most accurate. In an embodiment, accuracy can be determined by historical accuracy, or by whether a threshold change has been satisfied, or by the current size or contrast of an object, or by the like.

In an embodiment, a motion tracking system tracks object motion with respect to a motion tracking system reference or coordinate frame and then transforms the positional data into a biomedical imaging device reference or coordinate frame. The positional data in the reference frame of the biomedical imaging device is then used by the biomedical imaging device to update scanning parameters in real-time, resulting in images that show no or fewer motion artifacts and/or increased resolution.

In some embodiments, the positional data in the reference frame of the biomedical imaging device is analyzed to determine an amount or magnitude of motion present or tracked. One of ordinary skill in the art will appreciate that the foregoing can be accomplished using any other possible reference frames in lieu of the reference frame of the biomedical imaging device. If the amount or magnitude of motion exceeds a predetermined threshold, then the positional data in the reference frame of the biomedical imaging device is used by the biomedical imaging device to update scanning parameters in real-time, resulting in images that show no or fewer motion artifacts and/or increased resolution.

FIG. 1 is an embodiment of a schematic diagram illustrating a motion tracking system 100. The motion tracking system 100 comprises one or more detectors 102, a detector processing interface 104, a scanner controller 106, and a scanner 108. In an embodiment, the one or more detectors 102 are positioned generally within an interior volume of the scanner 108 (one of ordinary skill in the art will appreciate that the one or more detectors can be positioned in other locations, for example, outside the volume of the scanner) and positioned to each have a different viewpoint from which to view the subject 110 or to detect information describing at least one feature or quality of the subject 110. For example, features or qualities of the subject 110 that may be detected by various detectors 102 include but are not limited to a visual image or depiction of the subject 110 or a portion of the subject 110, a distance of the subject 110 or a portion of the subject 110 to the detector 102, a surface texture of the subject 110 or a portion of the subject 110, an indentation or protrusion of the subject, an opening or orifice of the subject, a structural outline of the subject or a portion of the subject, or other anatomical landmark or feature of the subject. Various embodiments may be configured to employ various numbers of detectors 102, and the detectors 102 can be positioned places other than within an interior volume of a scanner, as long at the detectors 102 are positioned to enable viewing the subject 110 or detecting information describing at least one quality of the subject 110 (for example, "patient movement data").

During an imaging scan, the detectors 102 are configured to acquire patient movement data and send the data to the detector processing interface 104. The detector processing interface 104 is configured to analyze the patient movement data using one or more tracking controllers or filters and to create tracking data describing movement or motion of the patient/object of interest in detector and/or scanner reference or coordinate frames. The tracking data is sent from the detector processing interface 104 to the scanner controller 106. The scanner controller 106 is configured to adjust the scanner 108 in real time based on patient/object of interest movement described in the tracking data to enable creation of scanned images with no or few motion artifacts. For example, the scanner controller 106 can be configured to adjust scan planes, locations, and/or orientations of the scanner 108 in real time.

Figure 9:
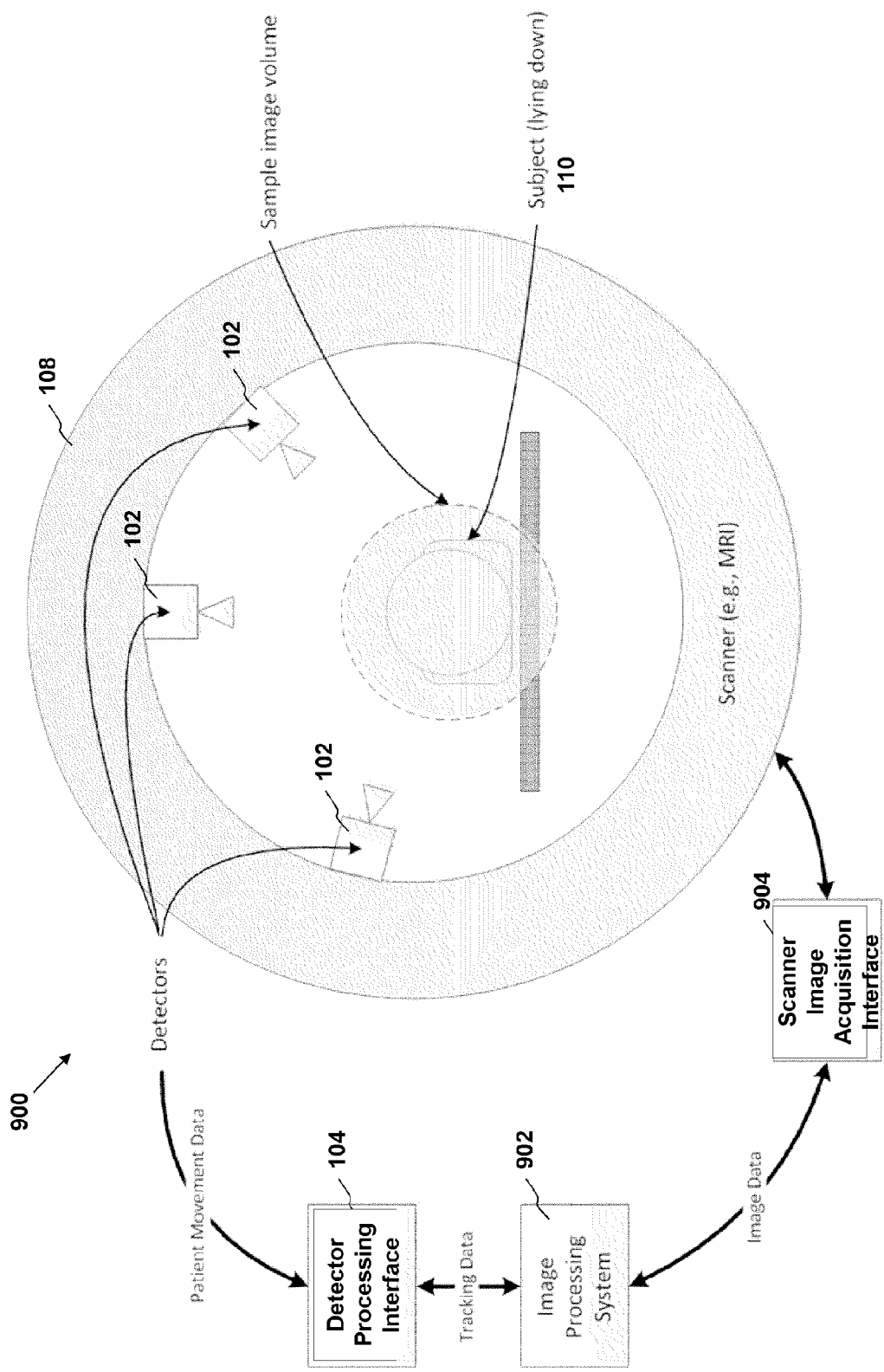
FIG. 9 is an embodiment of a schematic diagram illustrating a motion tracking system.

In some embodiments, such as the motion tracking system 900 illustrated in FIG. 9, the tracking data generated by the detector processing interface 104 is used to compensate for motion during image reconstruction or post-processing, rather than to directly adjust the scanner 108. In some embodiments, tracking data is used to both compensate for motion during image reconstruction and to directly adjust the scanner 108.

Various embodiments of motion tracking systems can be configured to use various types of detectors. In some embodiments, the detectors 102 are all cameras, with each detector 102 being configured to continuously record a partial or full view of the object of interest, such as a subject's face in the case of tracking a patient's head. Recording the partial or full views from various detector vantage points can enable increased accuracy and/or redundancy of various tracking techniques. In some embodiments, the detectors 102 may be cameras, laser-based sensors, projection-based sensors, radar sensors, ultrasonic sensors, other remote sensors, or any combination thereof.

Figure 2:
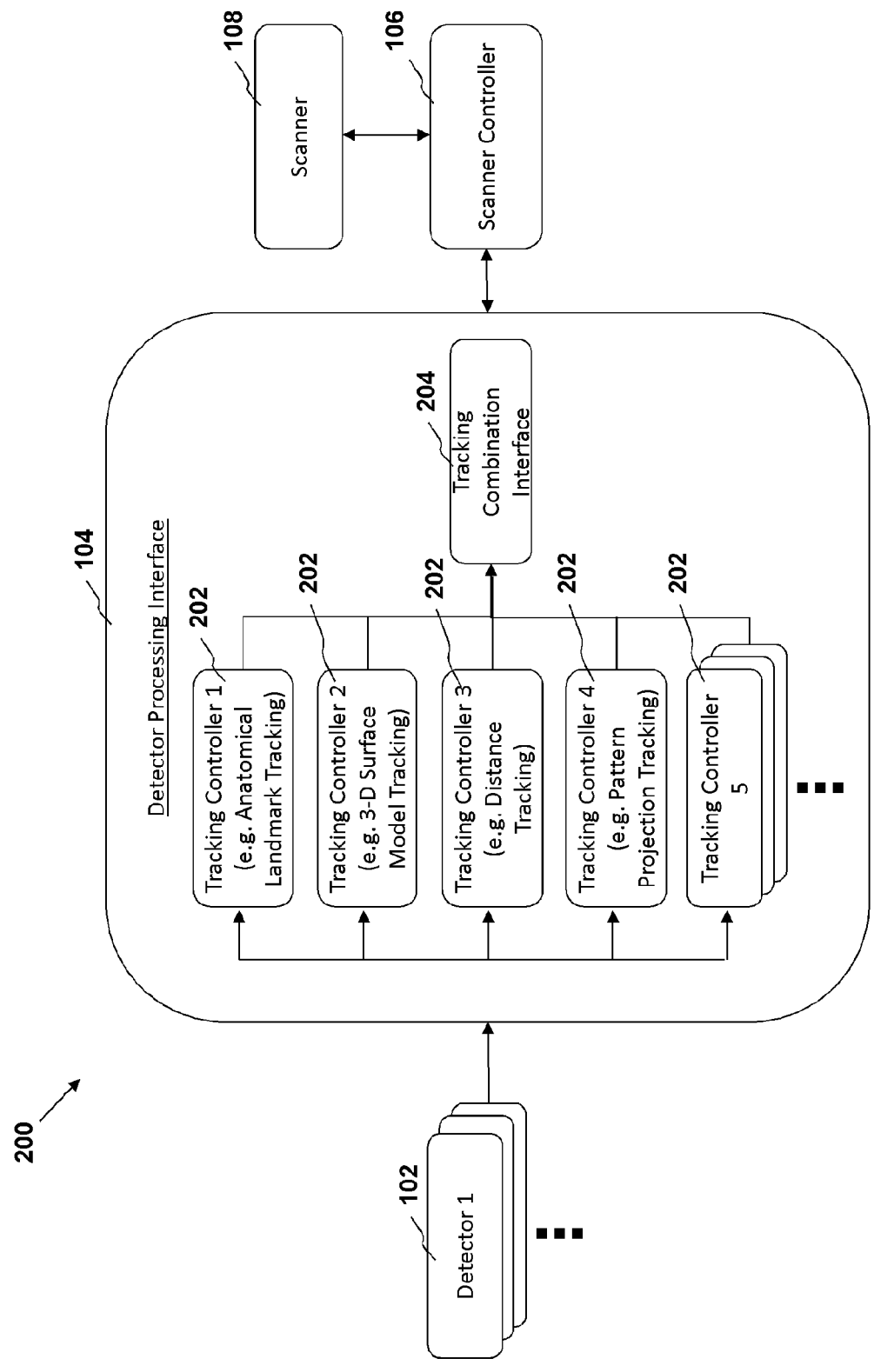
FIG. 2 is a block diagram depicting an embodiment of a motion tracking system.

Referring to FIGS. 1 and 2, patient movement data (for example, images, distance measurements, or the like) from the one or more detectors 102 is sent to the detector processing interface 104, where one or more tracking controllers or filters analyze the data to estimate movement of the object of interest. Several possible tracking controllers or filters 202, as shown in FIG. 2, either in isolation or in combination, can be configured to track the object of interest. One embodiment of a tracking controller or filter 202, for example Tracking Controller 1 shown in FIG. 2, is configured to track the position and orientation of anatomical features or "landmarks" during subject movement, and uses this information to derive the object of interest's (for example, the subject's head) movement. For example, when tracking a subject's head, if the position of the subject's two eyes and the position of the tip of the subject's nose are known in detector coordinates, then the three translations and three rotations of the subject's head can be derived by means of triangulation or other methods. In general, accuracy of such a tracking controller or filter 202 can be improved by tracking a greater number of anatomical features. For example, if the position of a subject's nostrils and/or the bridge of the nose are tracked in addition to the nose tip and the eyes, then tracking of the subject's head can be generally more accurate. Tracking accuracy can also be improved by utilizing a greater number of detectors 102 and/or positioning the detectors 102 to view the subject's head from a variety of angles. Furthermore, in some embodiments, a single tracking controller or filter can be configured to provide data for less than all six degrees of freedom, i.e. less than three translations and three rotations, in which case information from one or more other tracking controllers or filters may be used to complete the tracking of all six degrees of freedom.

Another embodiment of a tracking controller or filter 202, for example Tracking Controller 2 shown in FIG. 2, is configured to create a three-dimensional surface model of the object of interest (for example, a subject's head), and to calculate motion tracking information based on changes to the three-dimensional surface model as it is updated when the subject moves. A three-dimensional surface model tracking controller or filter can be configured to employ various types of detectors 102 and modeling methods. For example, the controller or filter is configured to create a surface model based on a surface texture of the object as detected by a detector or as detected by the scanner. In an embodiment, the controller or filter is configured to create a surface model based on changes in lighting and/or shading of the object of interest.

Some embodiments of tracking controllers or filters 202, for example Tracking Controller 3 shown in FIG. 2, are configured to use estimates of a distance of the object of interest (or a portion or portions of the object of interest) to one or more of the detectors 102. The position of the object of interest can then be estimated or derived by combining the distance estimates from multiple detectors 102 and/or by monitoring changes in the distance estimates from an individual detector 102. Some distance estimation controller embodiments are configured to utilize, for example, range imaging, stereo triangulation, interferometry, or the like.

Other embodiments of tracking controllers or filters 202, for example Tracking Controller 4 shown in FIG. 2, are configured to track changes in a known pattern, for example, a regular grid, projected onto the object of interest. A projector projects one or more patterns onto the object of interest from one or more projection locations, and one or more detectors 102 detect images of the pattern projected onto the object of interest. The tracking controller or filter 202 is configured to analyze deformations and/or changes to the projection(s) as the subject 110 moves to derive an estimate of the object of interest's positioning.

Some embodiments of tracking controllers or filters 202 are configured to track light reflected from reflective and/or absorbent particles suspended or contained in a compound applied to a subject's skin. The compound can be, for example, a paste, a cream, a glue, a temporary tattoo, an ink, and the like. The compound can be painted, smeared, drawn, brushed, or otherwise applied to the subject's skin. The reflective particles can be configured to reflect light in different directions as the subject moves or rotates the skin area having the compound applied. For example, the reflective particles can be prisms that refract light in a known fashion, glitter particles, or the like. The absorbent particles can also be configured to absorb light in different directions as the subject moves or rotates the skin area having the compound applied. For example, the absorbent particles can be dark spheres that absorb light in a known fashion, or the like. This embodiment of a tracking controller or filter 202 is configured to analyze images detected by the detectors 102 to track light reflections and/or alterations from the various reflective and/or absorbent particles in order to determine movement of the object of interest. In some embodiments, the tracking controller or filter 202 is configured to track reflections and/or absorption of ambient light. In some embodiments, the tracking controller or filter 202 is configured to track reflections and/or absorptions of an auxiliary light source directed generally toward the reflective and/or absorbent particles.

Figure 7:
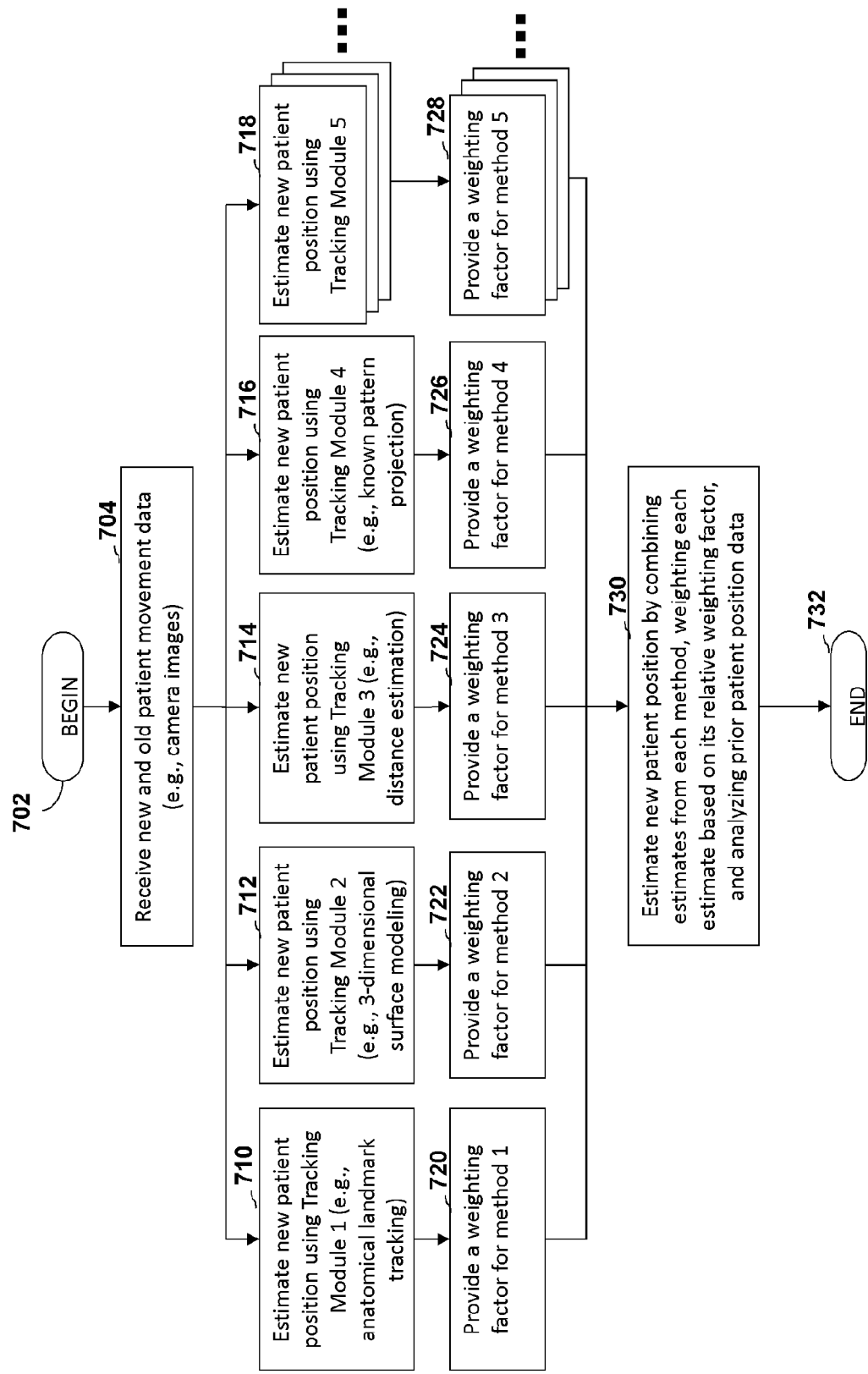
FIG. 7 depicts an embodiment of a process flow diagram illustrating an example of combining position estimates from more than one motion tracking controller or filter to produce a single or unitary position estimate.

In some embodiments, various embodiments of tracking controllers or filters 202 (including those described above and those using various other techniques) can be used either independently or in combination with other tracking controllers or filters, including markerless tracking controllers or filters, and modules utilizing markers for motion tracking. A tracking combination interface, such as the tracking combination interface 204 shown in FIG. 2, can be configured to receive position or movement estimates from a variety of tracking controllers or filters 202 and to either select one of the estimates to send to the scanner controller 106 or to combine one or more of the estimates to form a single or unitary, more accurate estimate to send to the scanner controller 106. In some embodiments, the position or movement estimates received by the tracking combination interface 204 each describe six degrees of freedom (for example, three translations and three rotations). In some embodiments, the position or movement estimates received by the tracking combination interface 204 each describe fewer than six degrees of freedom. In some embodiments, some of the position or movement estimates received by the tracking combination interface describe six degrees of freedom, while others describe fewer than six degrees of freedom. Tracking combination interface 204 can be configured to combine estimates from tracking controllers or filters 202, for example, as shown in FIG. 7 and described in greater detail below. In some embodiments, a tracking combination interface can be configured to send no motion updates to the scanner controller if the difference in motion or an amount or magnitude of tracked motion does not exceed a predetermined threshold.

FIG. 2 is a block diagram depicting an embodiment of a motion tracking system 200. The motion tracking system 200 comprises one or more detectors 102, a detector processing interface 104, a scanner controller 106, and a scanner 108. The detector processing interface further comprises several tracking controllers or filters 202 and a tracking combination interface 204. In the motion tracking system 200, the one or more detectors 102 send patient movement data (for example, camera images, distance estimates, signals, or the like) to the detector processing interface 104, and each of the several tracking controllers or filters 202 uses the patient movement data (or a portion of the patient movement data) to generate an estimate of movement of the patient/object of interest (for example, describing all six degrees of freedom or fewer than six degrees of freedom). The tracking combination interface 204 is configured to receive each tracking controller's individual estimate and to combine them (or to select one of them) to create tracking data comprising a single or unitary movement estimate to send to the scanner controller 106. The tracking combination interface 204 may also be configured to send no motion updates to the scanner controller 106, for example, to retain the most recent motion data, if the difference in motion or amount or magnitude of tracked motion does not exceed a predetermined threshold. The scanner controller 106 is configured to update one or more parameters of the scanner 108 in real time based on this tracking data received from the detector processing interface 104.

As described above, each of the tracking controllers or filters 202 of the motion tracking system 200 can be configured to track motion using a different technique (for example, anatomical landmark tracking, three-dimensional surface model tracking, distance tracking, or the like). In some embodiments, all or some of the tracking controllers or filters 202 can be configured to use the same technique, but with different configurations. For example, a detector processing interface 104 can comprise multiple tracking controllers or filters 202 utilizing anatomical landmark tracking, with each tracking controller or filter 202 being configured to track a different anatomical landmark or set of anatomical landmarks. Additionally, in some embodiments, tracking controllers or filters 202 can be configured to utilize more than one tracking technique. For example, a tracking module 202 can be configured to utilize both anatomical landmark tracking and three-dimensional surface model tracking, but to send one unitary tracking estimate based on a combination of both methods to the tracking combination interface 204 for combination with the estimates of other tracking controllers or filters 202.

The embodiment of a motion tracking system shown in FIG. 2 may be advantageous, because, in general, accuracy of a motion tracking system can be improved by tracking motion in a variety of ways (for example, utilizing a variety of tracking controllers or filters) and then combining the data derived from the various methods. Another advantage to using multiple tracking controllers or filters 202 (for example, equal to or greater than 2) is redundancy of data and measurements to improve the robustness of the tracking data. For example, when a patient is in certain positions, some tracking controllers or filters 202 may be able to produce more accurate estimates than others. Therefore, the most accurate tracking controller or controllers can be used at one time, and then a different controller or subset of controllers can be used at another time, to create the most accurate overall positioning estimates for a particular point in time or particular position of the subject at a particular point in time.

Redundancy in detectors 102 can also be advantageous. For example, some tracking controllers or filters 202 may only require one or two detectors 102, even though a tracking system, such as the tracking system shown in FIG. 1, has more than two detectors. However, in some cases, a patient's movement may block one or more detectors 102 from being able to view the object of interest. For example, if a patient turns his or her head to the left, a detector 102 on the patient's right may no longer be able to see, for example, the patient's left eye. In a system with redundant detectors 102, a tracking controller or filter 202 can be configured to, for example, use detectors 102 on the left side of a patient when the patient's head is turned to the left, but use detectors 102 on the right side when the patient's head is turned to the right.

Redundancy in detectors 102 and/or tracking controllers or filters 202 can enable, for example, the obstruction of an anatomical feature or landmark with respect to one detector 102 to not result in overall loss of tracking data, since other detectors 102 and/or tracking controllers or filters 202 can be configured to still have sufficient data to allow continued tracking.

Some embodiments of motion tracking systems utilize redundancy in tracking combination controllers or filters 204. For example, a detector processing interface 104 can comprise multiple tracking controllers or filters 202, with a first tracking combination controller or filter 204 configured to combine the position/movement data from half of the tracking controllers or filters 202, and a second tracking combination interface 204 configured to combine the position/movement data from the other half of the tracking controllers or filters 202. A third tracking combination interface 204 is configured to combine the position/movement data from the first and second tracking combination interfaces 204. This configuration may be advantageous in various situations, for example, when the second half of the tracking controllers or filters 202 are known to produce only intermittently accurate data. The third tracking combination interface 204 can then be configured to only take data from the second tracking combination interface 204 into account when the second tracking combination interface 204 indicates its position/movement data is accurate. This configuration may also be advantageous to allow grouping of tracking controllers or filters 202 with similar features together. For example, one tracking combination interface 204 can be configured to combine the estimates of all visual image-based tracking controllers or filters 202, while another tracking combination interface 204 can be configured to combine the estimates of tracking controllers or filters 204 using non-image based tracking, such as distance-based tracking.

Figure 3:
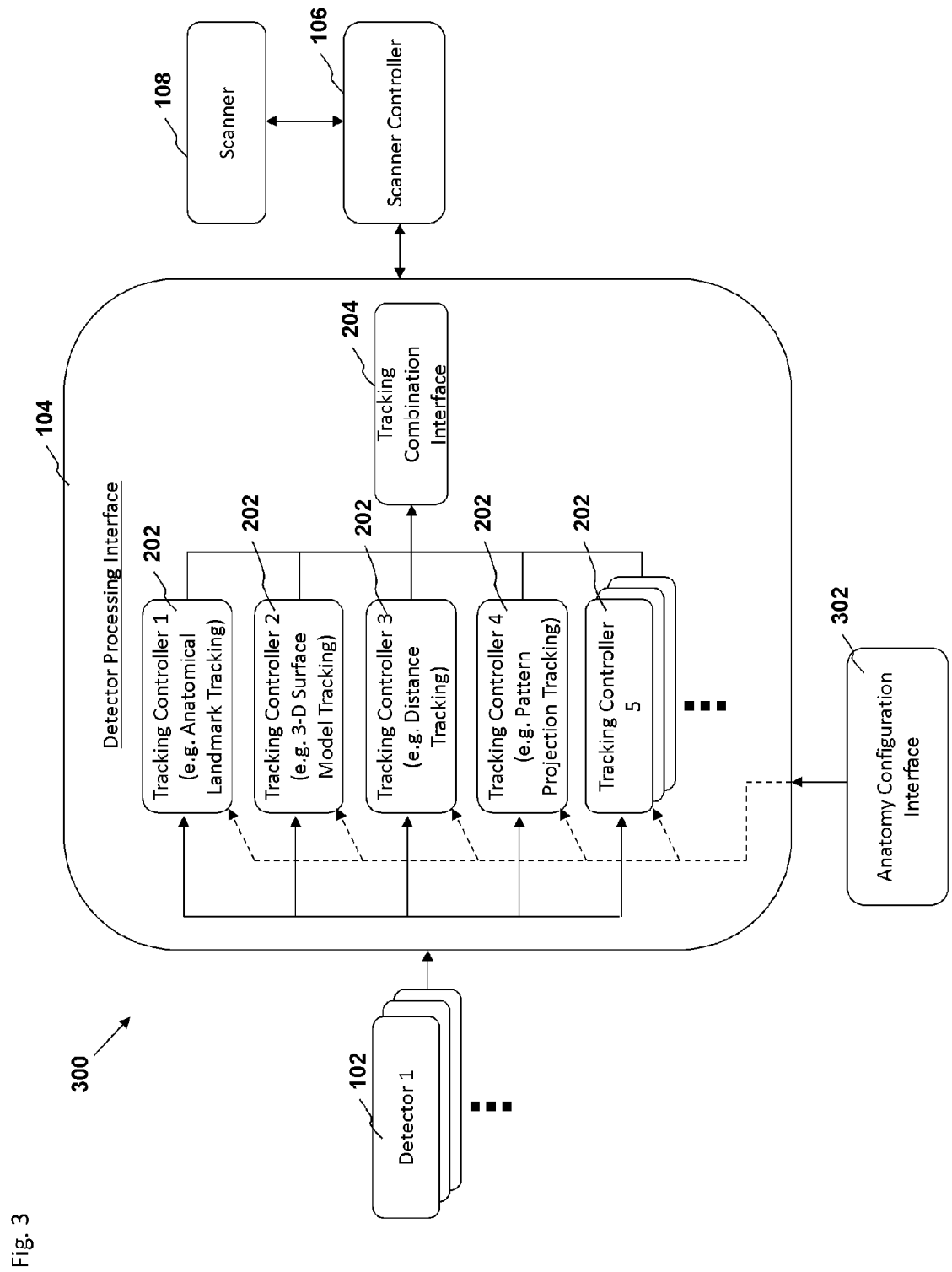
FIG. 3 is a block diagram depicting an embodiment of a motion tracking system.

FIG. 3 is a block diagram depicting an embodiment of a motion tracking system 300. The motion tracking system 300 includes, among other features, an anatomy configuration module 302 configured to allow changes to be made to configurations of the various tracking controllers or filters 202 used in the detector processing interface 104. For example, the anatomy configuration module 302 can configure the tracking controllers or filters 202 based on the specific anatomical region of the subject being tracked. If, for example, a subject's brain is being scanned, a tracking controller or filter 202 utilizing anatomical landmark tracking can be configured to track the subject's eyes, nostrils, or the like. But if a subject's knee is being scanned, a tracking controller or filter 202 utilizing anatomical landmark tracking can be configured to track, for example, regions above and below the knee and the kneecap.

The anatomy configuration module 302 can be configured to adjust the configuration of the tracking controllers or filters 202 based on various factors, such as the anatomical region or organ being scanned, a patient's age or sex, or even to compensate for situations where certain anatomical features are not available to be viewed, such as after surgery (where, for instance, an eye or another part of the face may be covered).

In some embodiments, an operator of the motion tracking system 300 provides data to the anatomy configuration module 302 to enable it to configure the various tracking controllers or filters 202. For example, the operator can use a computer interface to indicate that the scanner 108 will be scanning a subject's head, knee, or the like. In some embodiments, the anatomy configuration module 302 is configured to detect the portion of a subject that is being scanned and to automatically configure the tracking controllers or filters 202 without requiring operator input. For example, the anatomy configuration module 302 can be configured to analyze data from the detectors 102 to automatically determine whether the detectors are viewing a subject's head, knee, or the like.

Figure 4:
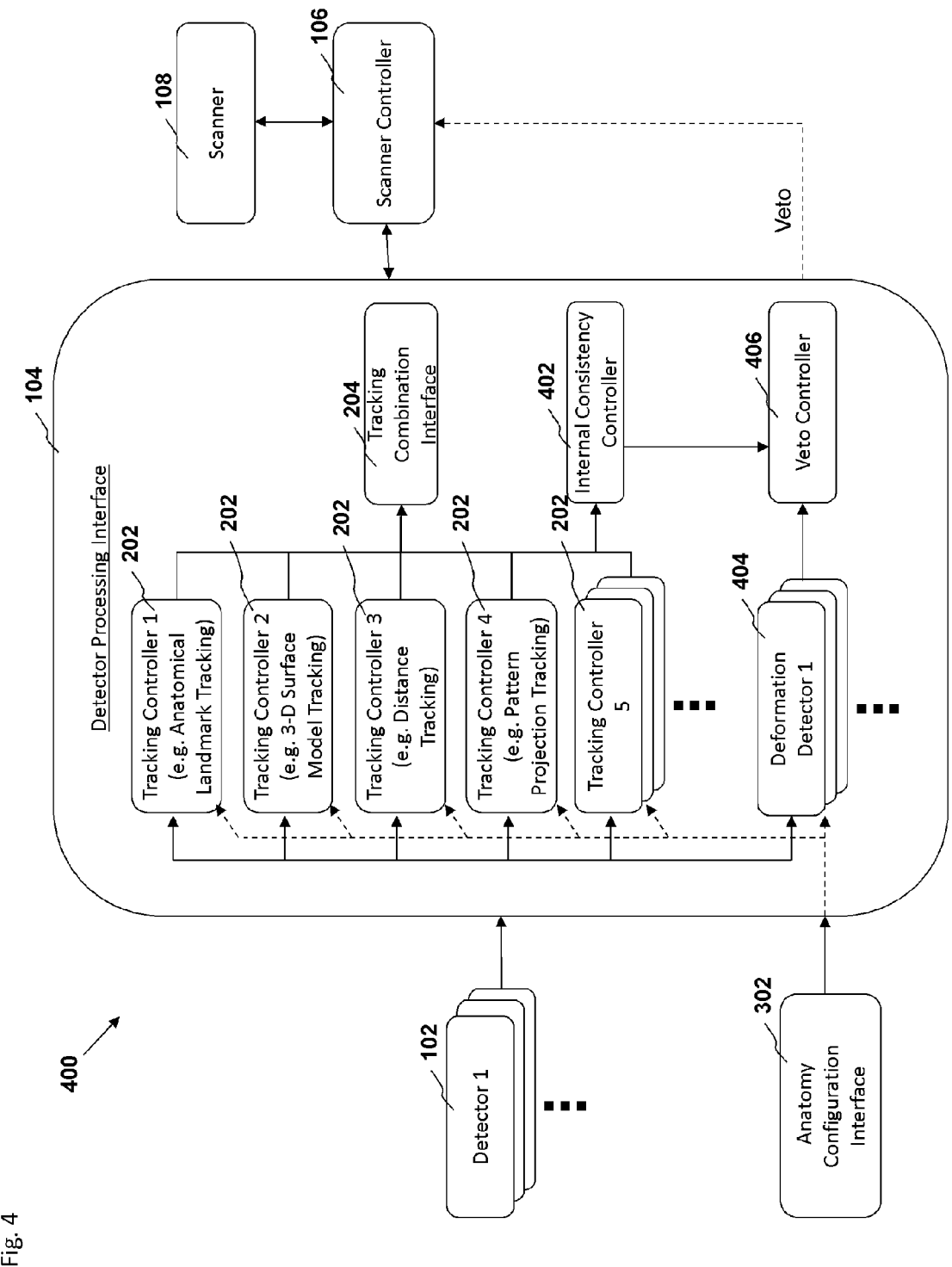
FIG. 4 is a block diagram depicting an embodiment of a motion tracking system.

FIG. 4 is a block diagram depicting an embodiment of a motion tracking system 400. The motion tracking system 400 includes, among other features, one or more deformation detectors 404, an internal consistency controller 402, and a veto controller 406. During the tracking of motion of a patient during a scan, the deformation detectors 404 and internal consistency controller 402 are configured to monitor data from the detectors 102 and/or tracking controllers or filters 202 for certain conditions that may adversely affect tracking data. When one of these conditions occurs, the deformation detector 404 or internal consistency controller 402 is configured to notify the veto controller 406 of the condition. The veto controller 406 is configured to analyze the condition(s) and send a veto signal to the scanner controller 106 if it determines the tracking data is sufficiently untrustworthy. The scanner controller 106 can be configured to pause or suppress scanner acquisitions if the veto controller 406 indicates that the tracking data are temporarily unreliable. Alternatively, the scanner controller 106 can be configured to not compensate for movement using the tracking data when the veto controller 406 indicates that the tracking data are temporarily unreliable.

In some embodiments, the veto controller 406 is configured to receive and analyze data from the deformation detectors 404 and internal consistency controller 402 substantially simultaneously. The veto controller 406 is configured to combine these data and make a determination as to whether to send a veto signal to the scanner controller 106. The combination of the data may be based on a simple "winner takes all" approach (for example, if data from one deformation detector or internal consistency controller indicates unreliable tracking, the veto controller 406 sends the veto signal), or the combination may involve weighting of different probabilities of the various discrepancies encountered, a Bayesian probability approach, or other probability or statistical-based approaches.

In the embodiment shown in FIG. 4, the deformation detectors 404 and internal consistency controller 402 both notify the veto controller 406 of potentially untrustworthy tracking data being generated by the tracking controllers or filters 202. However, the deformation detectors 404 and internal consistency controller 402 perform this function in different ways. The deformation detectors 404 monitor data from the detectors 102 for conditions likely to cause untrustworthy or degraded tracking data. For example, when tracking a head/brain, when a patient in the scanner sneezes or is squinting, the patient's skin may deform locally, resulting in loss of tracking accuracy, because, while the patient's skin moved, the patient's brain likely did not move in synchronization with the skin movement. The deformation detectors 404 can be configured to analyze the data from the detectors 102, and to flag these or other conditions detrimental to accurate tracking, such as sudden appearance of skin folds or changes in the shape of anatomical features.

The internal consistency controller 402 is configured to monitor the data output by the various tracking controllers or filters 202 to detect discrepancies between the tracking controllers or filters 202. For example, the internal consistency controller 402 can be configured to compare position estimates from each tracking controller 202 and to send a signal to the veto controller or filter 406 when the differences in position estimates from different tracking controllers or filters 202 exceed a threshold level or an estimated maximum magnitude of error. The threshold level that, if exceeded, triggers a signal to the veto controller or filter 406, can be a predetermined value or a continuously modified value based on, for example, weighting of different probabilities of the various discrepancies encountered, a Bayesian probability approach, or other methods.

Figure 5:
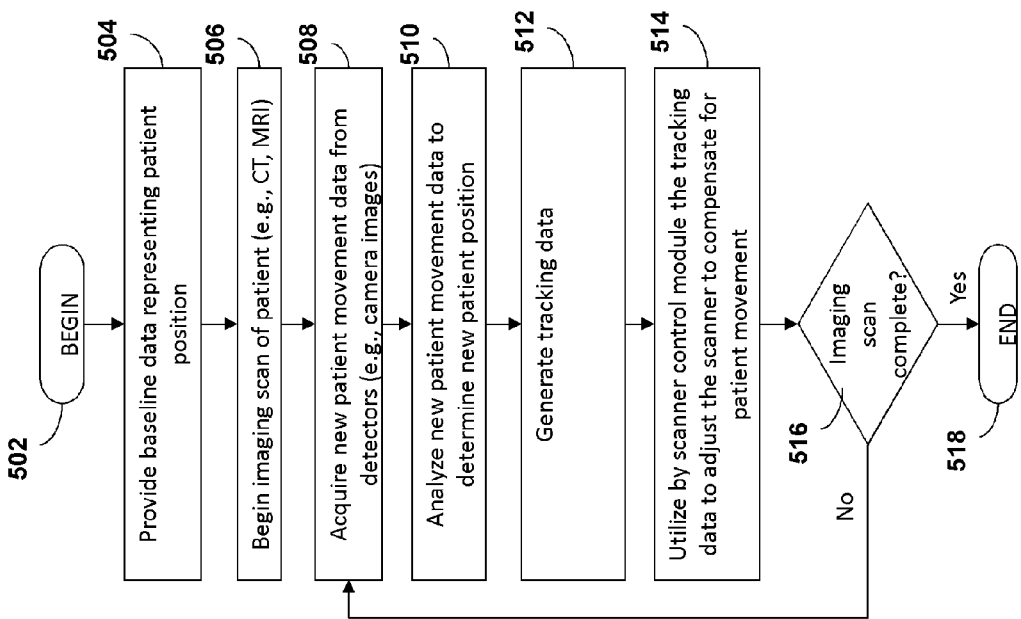
FIG. 5 depicts an embodiment of a process flow diagram illustrating an example of tracking and compensating for motion in biomedical imaging using a motion tracking system.

FIG. 5 depicts an embodiment of a process flow diagram illustrating an example of tracking and compensating for motion in biomedical imaging using a motion tracking system. At block 502 the process begins. At block 504 the system provides baseline data representing a patient position. For example, the detectors 102 as shown in the motion tracking system 100 of FIG. 1 acquire information about a subject, such as images of the subject, and send this data to the detector processing interface 104. The detector processing interface 104 is configured to analyze this data and determine a baseline positioning of the patient or the object of interest. At block 506 a scanner, such as the scanner 108 of the motion tracking system 100, begins an imaging scan of the patient. For example, an MRI scanner begins a magnetic resonance imaging scan of the patient.

At block 508 the detectors acquire new patient movement data. For example, the detectors acquire new images, camera frames, distance estimates, or the like of the patient or the object of interest. At block 510 the system analyzes the new patient movement data to estimate a new patient positioning. For example, the data from the detectors 102 is analyzed by each of the tracking controllers or filters 202 as described above, and each tracking controller 202 generates an estimate of the new patient position. The estimates from the various tracking controllers or filters 202 are then fed into the tracking combination interface 204. The tracking combination interface 204 combines the various estimates from the tracking controllers or filters 202 and generates a single estimate to send to the scanner controller 106. At block 512 the tracking combination interface generates tracking data containing the single estimate derived from the various estimates from the tracking controllers or filters 202. At block 514 the scanner controller utilizes the tracking data from the tracking combination interface to adjust the scanner to compensate for patient movement. For example, the scanner controller 106 adjusts in real time scan planes, locations, or orientations of the scanner.

At block 516 the process varies depending on whether imaging scan is complete. If the imaging scan is not complete, the process returns to block 508 and acquires new patient movement data from the detectors. This process continues throughout the imaging scan to continuously adjust the scanner based on patient motion. When the imaging scan is complete, the process moves from block 516 to the end of the process at block 518.

Figure 6:
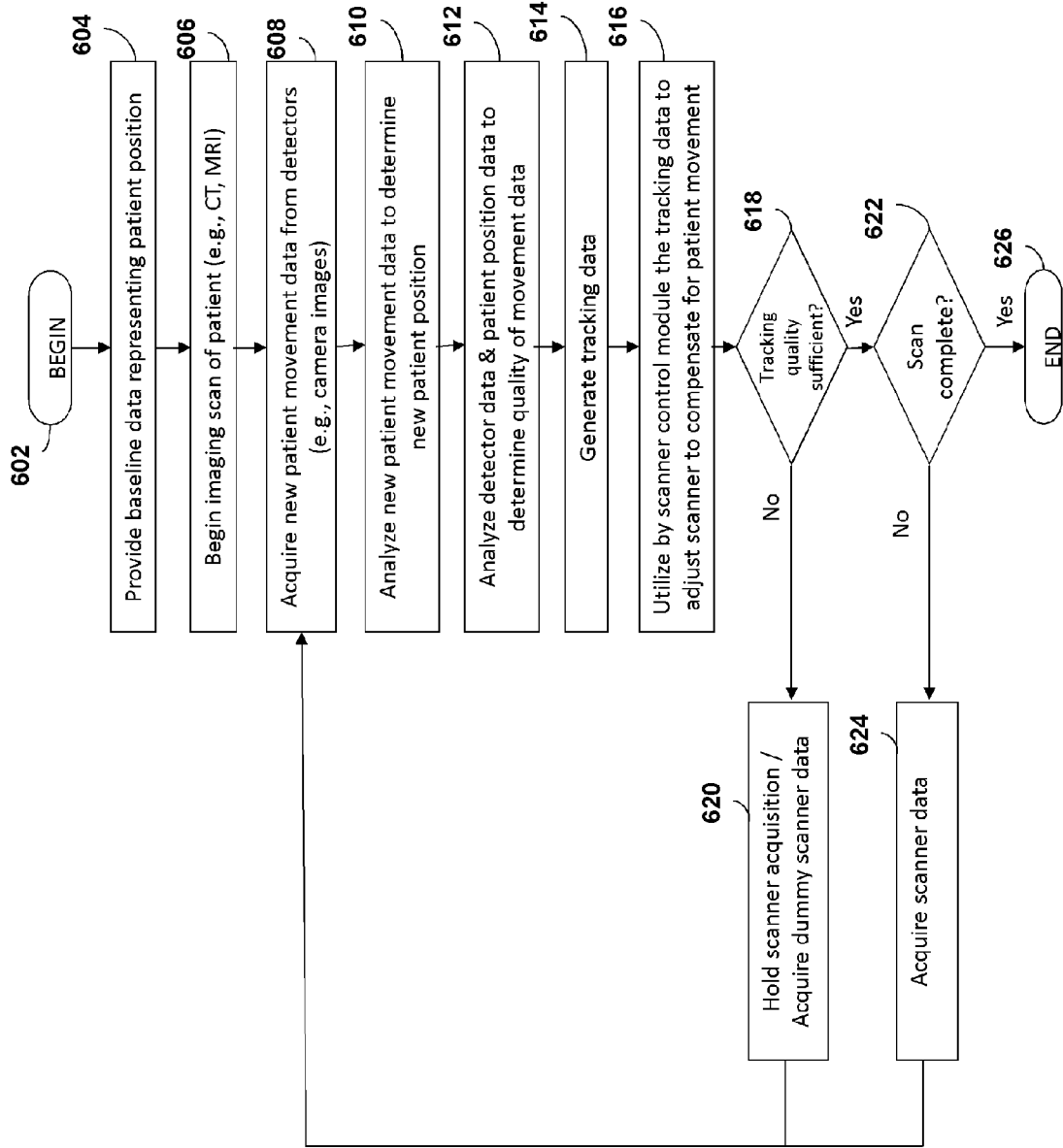
FIG. 6 depicts an embodiment of a process flow diagram illustrating an example of tracking and compensating for motion in biomedical imaging using a motion tracking system.

FIG. 6 depicts an embodiment of a process flow diagram illustrating an example of tracking and compensating for motion in biomedical imaging using a motion tracking system. In this embodiment, the process includes blocks that analyze the quality of the tracking information and potentially notify the scanner controller of inconsistencies in the tracking information. The process begins at block 602. At block 604 baseline data representing the patient position is provided. For example, detectors, such as the detectors 102 shown in the motion tracking system 100, detect patient data and send that data to a detector processing interface, such as the detector processing interface 104 shown in the motion tracking system 100. The detector processing interface analyzes the data from the detectors and determines a baseline positioning of the patient or object of interest as previously described.

At block 606 the scanner begins an imaging scan of the patient. At block 608 new patient movement data is acquired from the detectors. For example, the detectors acquire new images, distance estimates, or the like of the current patient position or orientation. At block 610 the new patient movement data is analyzed to estimate a new patient position. For example, the detector processing interface 104 shown in the motion tracking system 100 utilizes its tracking controllers or filters 202 and tracking combination interface 204 to generate an estimate of the new patient position, as described above. At block 612 the system analyzes the detector data and/or the new patient position data to determine a quality of the movement data. For example, multiple deformation detectors, such as the deformation detectors 404 shown in the motion tracking system 400, analyze the new patient data from the detectors 102 to determine if the object being tracked is experiencing, for example, skin deformations that may reduce the quality of the tracking data. Additionally, an internal consistency controller, such as the internal consistency controller 402 of the motion tracking system 400, analyzes the output of each tracking controller or filter to determine if, for example, outputs of the various tracking controllers or filters differ by more than a predetermined threshold amount.

At block 614 the system generates tracking data describing the estimated positioning of the patient or object of interest. The tracking data can be generated, for example, by using the tracking combination interface 204 shown in the motion tracking system 400. At block 616 the scanner controller uses the generated tracking data to adjust the scanner to compensate for patient movement. For example, the scanner controller instructs the scanner to adjust scan planes, locations, or orientations.

At block 618, the process, for example by using a veto controller 406, determines whether the tracking quality is sufficient. If the veto controller 406 determines that an output from the internal consistency controller 402 or one of the deformation detectors 404 indicates unreliable tracking data, the veto controller can send a veto signal indicating that the tracking quality is insufficient. At block 620, if the tracking quality is insufficient, the scanner 108 can be instructed to pause acquisition of scanner data and/or to acquire dummy scanner data, for example, by sending a veto signal from the veto controller 402 to the scanner controller 106. The process then moves back to block 608 and acquires new patient movement data, continuing the process as before. This process can continue until the tracking quality is determined to be sufficient. If the tracking quality is determined to be sufficient at block 618, the process moves to block 622. At block 622, the process varies depending on whether the imaging scan is complete. If the imaging scan is not complete, the process moves to block 624 and acquires new scanner data with the imaging scanner. The process then moves back to block 608 and acquires new patient movement data and continues the process as previously described. If at block 622 the scan is complete, the process moves to block 626 and ends. In an embodiment, the system can be configured to move to block 626 if the system fails to complete a scan, times out, or exceeds a certain number of pauses or dummy scans at block 618 or block 622.

In some embodiment, blocks 616 and 618 are reversed. In these embodiments, the process determines whether the tracking quality is sufficient before the process adjusts the scanner to compensate for patient movement.

FIG. 7 depicts an embodiment of a process flow diagram illustrating an example of combining position estimates from more than one motion tracking controller or filter to produce a single or unitary position estimate. This embodiment illustrates an example of how a motion tracking system can use multiple tracking controllers or filters, such as the tracking controllers or filters 202 shown in FIG. 2, to individually calculate an estimate of a patient position, and then combine the various estimates to develop a single or unitary estimate using a tracking combination interface, such as the tracking combination interface 204 shown in FIG. 2. At block 702 the process begins. At block 704, the system receives both new and old patient movement data, such as images, distance estimates, or the like from the detectors 102. The new and old patient movement data is received by the detector processing interface 104 and sent to the various tracking controllers or filters 202.

At blocks 710, 712, 714, 716, and 718 various tracking controllers or filters 202 estimate a new patient position using the new and old patient movement data received at block 704. For example, one tracking controller or filter 202 estimates a new patient position using anatomical landmark tracking, one tracking controller estimates a patient position using three dimensional surface modeling, another tracking controller estimates the new patient position using distance estimation, or the like, as described above. At blocks 720, 722, 724, 726, and 728 the various tracking controllers or filters provide a weighting factor for their respective position estimates. For example, a weighting factor may include an error estimate, a probability, a confidence level, or another measure related to accuracy. Each weighting factor can be used to indicate at least partially a weight that should be applied to the patient positioning estimate output by each tracking controller. For example, if a one tracking controller 202 develops an estimate that it determines to be relatively accurate, that tracking controller's weighting factor may be 95 (on a scale of 1-100). If another tracking controller 202 develops an estimate that it determines to be relatively inaccurate or having a relatively large margin of error, that tracking controller's weighting factor may be 20 (on the same scale of 1-100).

At block 730 the system estimates a single or unitary new patient position, for example, by using the tracking combination interface 204, to combine the estimates from each tracking controller 202. This process of combining estimates from the various tracking controllers or filters can take various forms. For example, the estimates can be combined using a simple average or a weighted average based on the weighting factors provided by each tracking controller 202. Another option is a winner takes all approach. In a winner takes all approach, the tracking combination interface merely picks the estimate from the tracking controller having the highest weighting factor. The tracking combination interface may also use other more complex approaches, such as Bayesian probability or other statistical approaches. In some embodiments, at block 730 the tracking combination interface 204 also considers prior patient position estimates in estimating the new patient position. For example, the tracking combination interface can use Kalman filtering or other prediction approaches. The process ends at block 732. In a complete motion tracking system, such as the motion tracking system 200 shown in FIG. 2, the process illustrated in FIG. 7 can be performed continuously throughout an imaging scan to continuously develop position estimates and adjust the scanner in real time.

Figure 8:
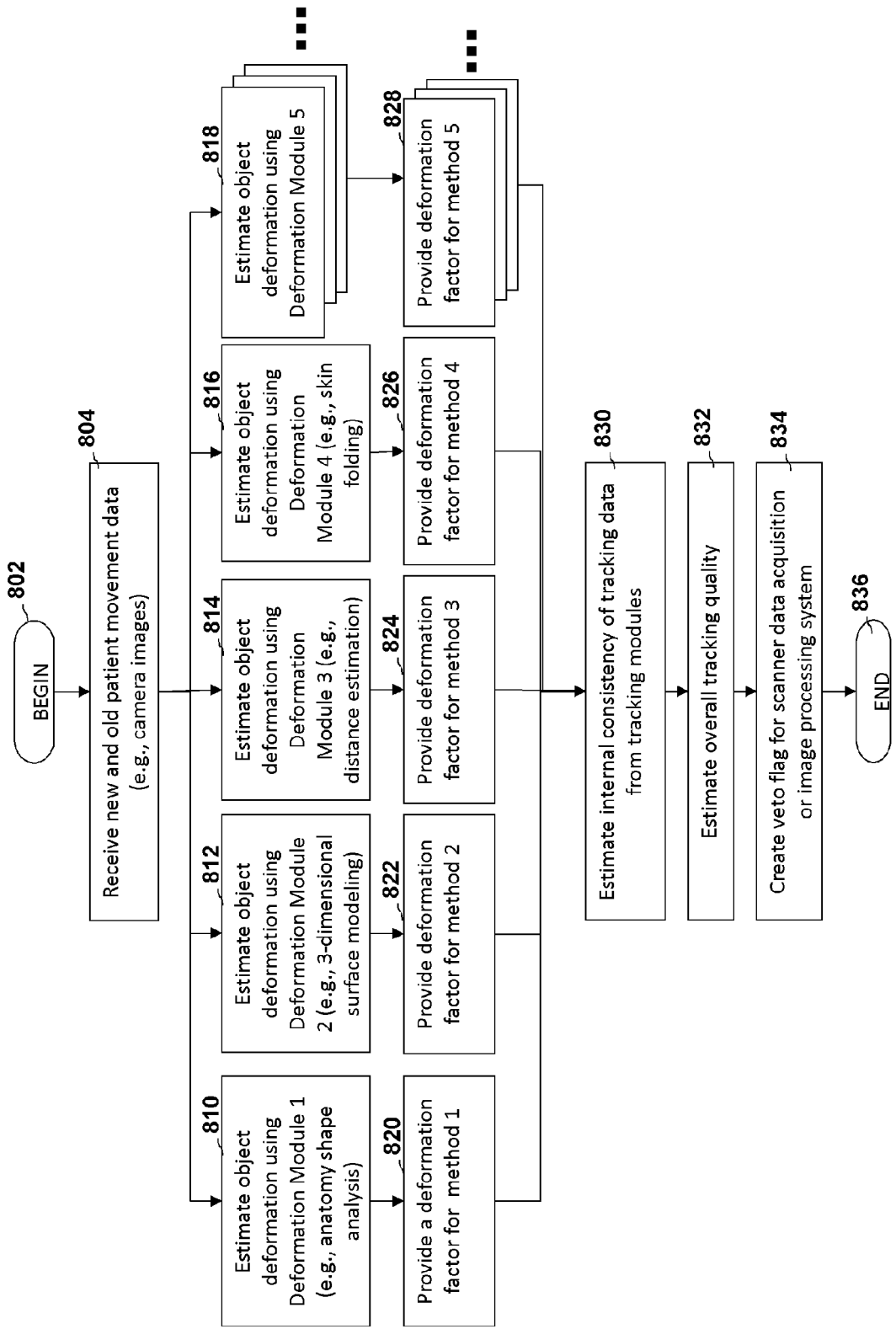
FIG. 8 depicts an embodiment of a process flow diagram illustrating an example of estimating the tracking of a feature during an imaging scan.

FIG. 8 depicts an embodiment of a process flow diagram illustrating an example of estimating tracking quality during an imaging scan. The process shown in FIG. 8 illustrates estimating deformation of an object of interest and estimating the internal consistency of tracking data, and then combining each of those estimates to estimate an overall tracking quality. The overall tracking quality is used to create a veto flag or signal as needed when tracking quality is insufficient, as described above. The process begins at block 802. At block 804 new and old patient movement data is received, for example, from detectors, such as the detectors 102 shown in the motion tracking system 400 of FIG. 4. The patient movement data may comprise, for example, images, distance estimates, or the like.

At blocks 810, 812, 814, 816, and 818 deformation of the subject or object of interest is estimated using various deformation filters, such as the deformation detectors 404 shown in FIG. 4. The various deformation filters can use different detection methods, such as anatomy shape analysis, three dimensional surface modeling, distance estimation, and/or skin folding analysis, as described above. At blocks 820, 822, 824, 826, and 828, each deformation detector provides a deformation factor representing at least partially the estimated accuracy of the estimate produced by each deformation detector. The deformation factors may include an absolute measure of deformation, a measure of nonlinear warping, an error estimate, a probability, a confidence level, or another measure related to the accuracy of the estimate of deformation of the object of interest.

At block 830 the internal consistency of the tracking data from the tracking controllers or filters is estimated. This function may be performed by, for example, an internal consistency controller, such as the internal consistency controller 402 shown in FIG. 4. The internal consistency controller 402, as described above, analyzes the positional data from the various tracking controllers or filters and determines if there are inconsistencies between the various controllers or filters that exceed a certain level.

At block 832 a controller, such as the veto controller 406 shown in FIG. 4, estimates the overall tracking quality of the motion tracking data. For example, the veto controller 406, as described above, combines the deformation detector data with the internal consistency controller data and determines whether the tracking data is of sufficient quality. At block 834, if the veto controller determines the overall tracking quality is of insufficient quality, the veto controller creates a veto flag or signal for a scanner controller or an image processing system, such as the scanner controller 106 shown in FIG. 4 or the image processing system 902 shown in FIG. 10. At block 836 the process is complete. In a complete motion tracking system, such as the motion tracking system 400 shown in FIG. 4, the process illustrated in FIG. 8 can be performed continuously throughout an imaging scan to continuously develop tracking quality estimates and inform the scanner controller or image processing system when tracking quality is insufficient.

FIG. 9 is an embodiment of a schematic diagram illustrating a motion tracking system 900. The motion tracking system 900 comprises detectors 102, a detector processing interface 104, an image processing system 902, a scanner image acquisition interface 904, and a scanner 108. In the motion tracking system 900, the detector processing interface analyzes patient movement data from the detectors 102 to estimate patient/object of interest movement during a scan. The detector processing interface 104 generates tracking data defining the estimates of the patient/object of interest's movement and sends the tracking data to an image processing system 902. In this embodiment, the motion tracking system 900 corrects for patient motion during image reconstruction or post-processing rather than adjusting a scanner in real time to compensate for patient movement. One advantage of the embodiment shown in FIG. 9 is that the motion tracking system 900 does not require a scanner with the ability to adjust imaging parameters, such as scan planes, locations, or orientations, in real time. In some embodiments, a motion tracking system includes features of both the motion tracking system 100 shown in FIG. 1 and the motion tracking system 900 shown in FIG. 9. For example, a motion tracking system can be configured to adjust some scanner parameters in real time while other parameters are compensated for during image reconstruction or post-processing.

Figure 10:
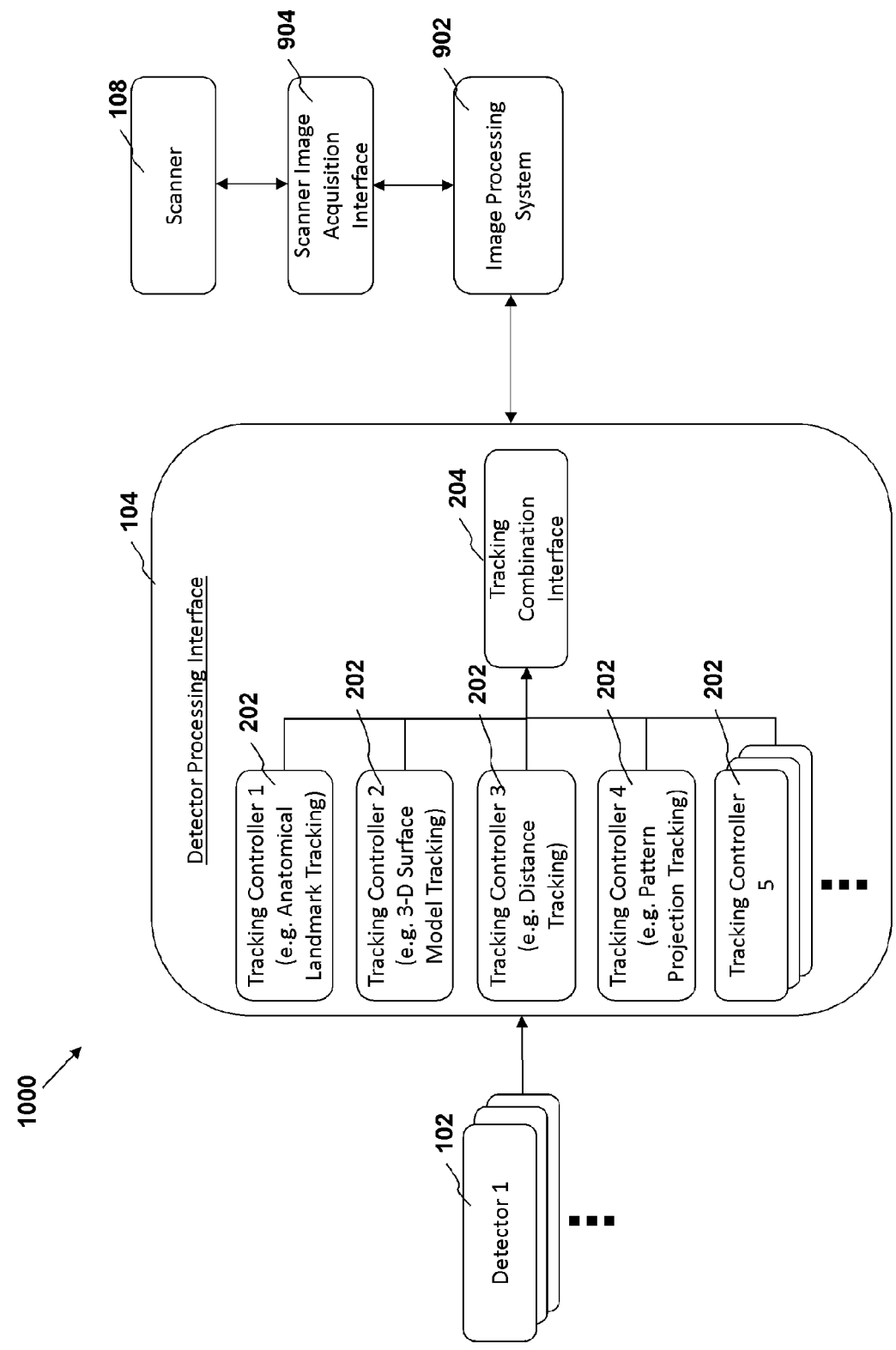
FIG. 10 is a block diagram depicting an embodiment of a motion tracking system.

FIG. 10 is a block diagram depicting an embodiment of a motion tracking system 1000. The motion tracking system 1000 comprises one or more detectors 102, a detector processing interface 104, an image processing system 902, a scanner image acquisition interface 904, and a scanner 108. The motion tracking system 1000 operates similarly to the motion tracking system 200 shown in FIG. 2. However, the motion tracking system 1000 sends tracking data from the detector processing interface 104 to an image processing system 902 instead of a scanner controller 106. The scanner acquisition interface 904 receives images from the scanner 108 and sends the images to the image processing system 902. The image processing system 902 is configured to receive image data from the scanner image acquisition interface 904 and tracking data from the detector processing interface 104. The image processing system 902 is configured to adjust the image data based on the tracking data received from the detector processing interface 104 to compensate for patient movement.

Figure 11:
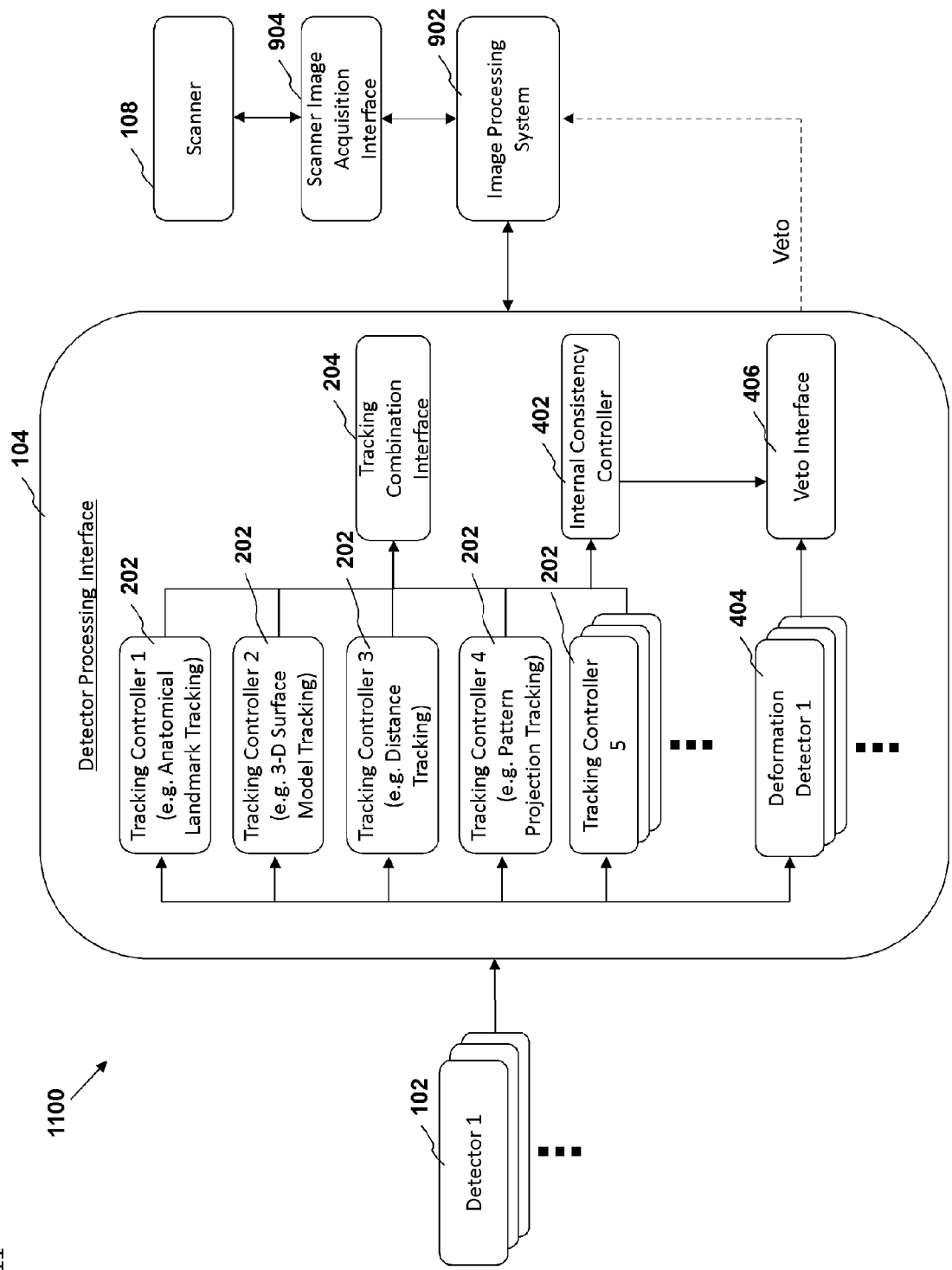
FIG. 11 is a block diagram depicting an embodiment of a motion tracking system.

FIG. 11 is a block diagram depicting an embodiment of a motion tracking system 1100. The motion tracking system 1100 is similar to the motion tracking system 400 shown in FIG. 4; however, the motion tracking system 1100 is configured to correct for patient movement during image reconstruction or post-processing rather than adjusting a scanner in real time due to patient movement. In the motion tracking system 1100, tracking data and/or a veto signal from the detector processing interface 104 are sent to an image processing system 902, instead of to a scanner controller 106. The image processing system 902 uses tracking data from the detector processing interface 104 to correct images received from the scanner image acquisition interface 904 for patient motion during image reconstruction or post-processing. The image processing system 902 can be configured to not adjust certain images for motion during image reconstruction when the image processing system 902 receives a veto signal from the detector processing interface 104. The veto controller 406 operates to generate the veto signal as describe above in reference to various other embodiments.

Figure 12:
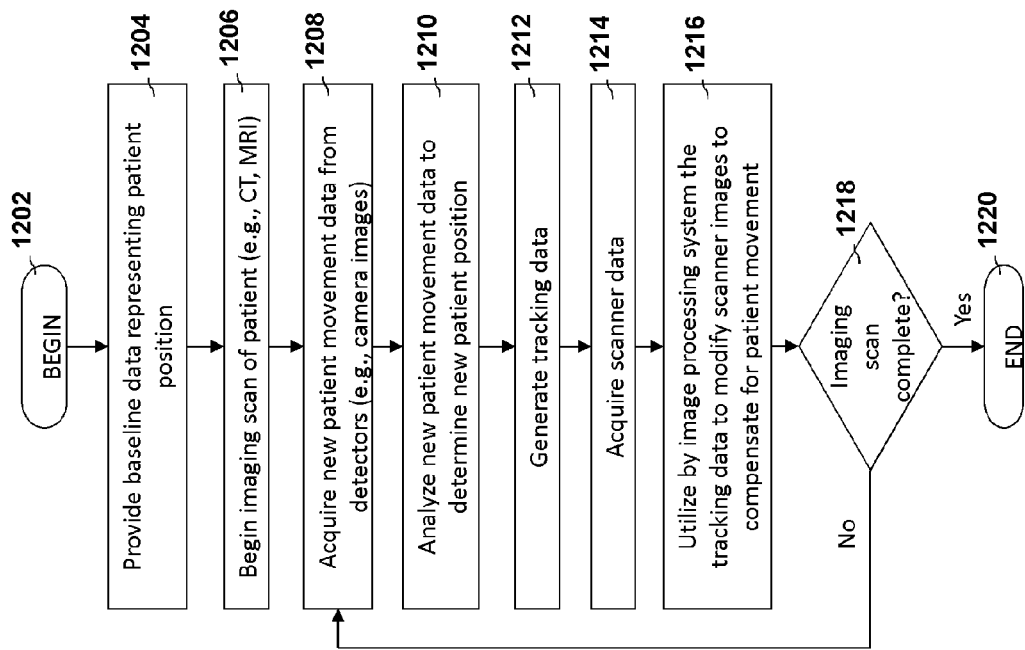
FIG. 12 depicts an embodiment of a process flow diagram illustrating an example of tracking and compensating for motion in biomedical imaging using a motion tracking system.

FIG. 12 depicts an embodiment of a process flow diagram illustrating an example of tracking and compensating for motion in biomedical imaging using a motion tracking system. The process shown in FIG. 12 can be implemented by, for example, the motion tracking system 900 shown in FIG. 9. At block 1202 the process begins. The system provides baseline data representing a patient's pre-scan position at block 1204. For example, detectors 102 detect information, such as images of a patient or object of interest, and send this information to a detector processing interface 104. The detector processing interface 104 uses various tracking controllers or filters 202 and a tracking combination interface 204, as described above, to then determine a baseline positioning of the patient or object of interest. At block 1206 the imaging scan of the patient or object of interest is begun.

At block 1208 new patient movement data, for example images, distance estimates, or the like, is acquired using the detectors 102. At block 1210 the new patient movement data is analyzed and compared to the baseline patient data to determine a new patient positioning estimate as described above. Block 1210 is performed by, for example, the detector processing interface 104 shown in FIG. 10. At block 1212 the system generates motion tracking data. The motion tracking data can be generated by, for example, the tracking combination interface 204 shown in FIG. 10, and describes the motion estimate generated by the tracking combination interface 204. At block 1214 scanner data is acquired. For example, the scanner 108 shown in FIG. 10 acquires scanner image data and sends the data to the scanner image acquisition module 904.

At block 1216 the image processing system, such as the image processing system 902 shown in FIG. 10, utilizes the acquired scanner data and generated tracking data to modify scanner images to compensate for patient movement. At block 1218 the process varies depending on whether the imaging scan is complete. If the imaging scan is not complete the process proceeds back to block 1208 and acquires new patient movement data from the detectors 102. The process then continues as described above. This process continues throughout the imaging scan to continuously modify the scanner images based on patient motion. If the imaging scan is complete at block 1218, the process proceeds to block 1220 and the process is complete.

Figure 13:
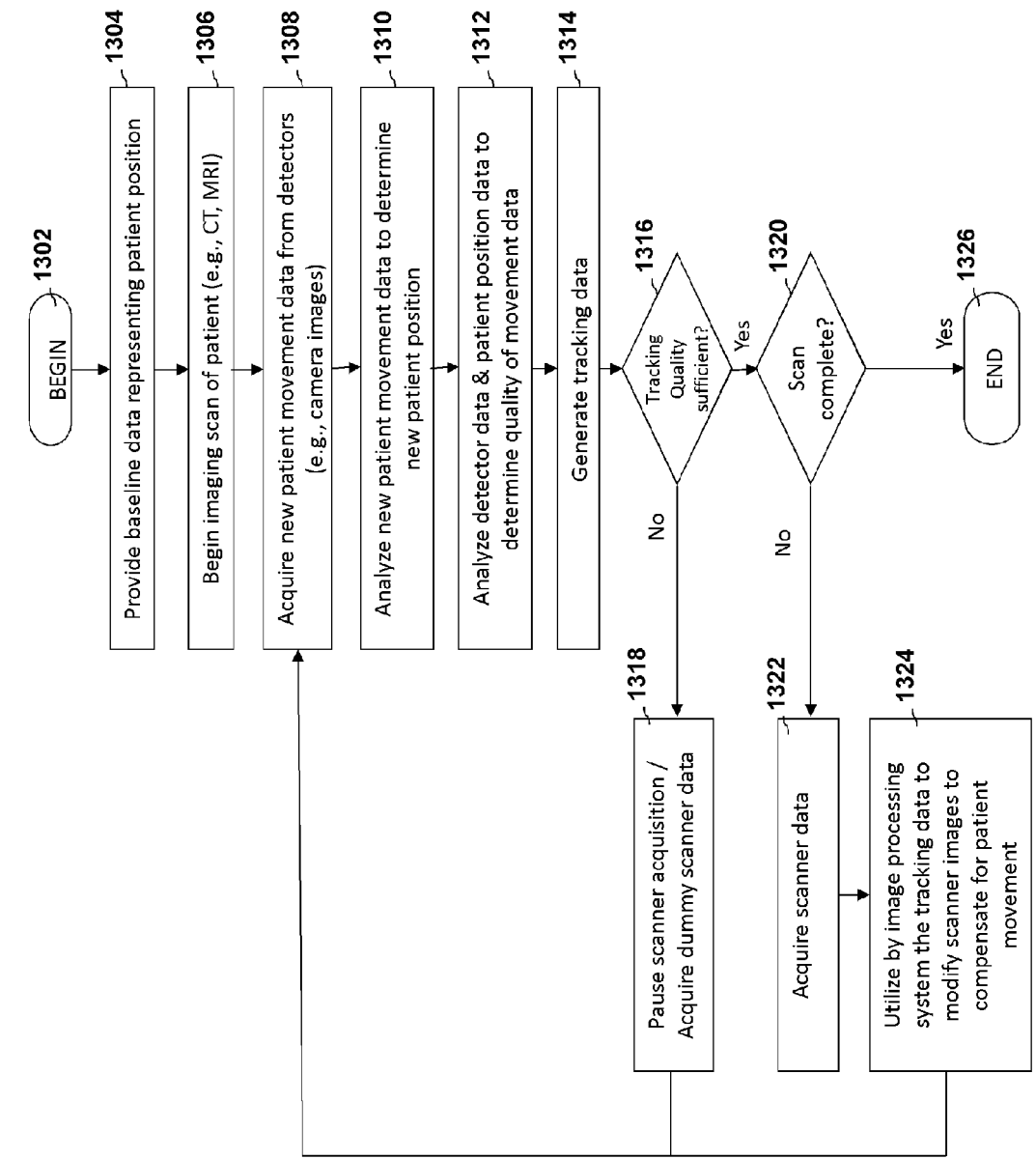
FIG. 13 depicts an embodiment of a process flow diagram illustrating an example of tracking and compensating for motion in biomedical imaging using a motion tracking system.

FIG. 13 depicts an embodiment of a process flow diagram illustrating an example of tracking and compensating for motion in biomedical imaging using a motion tracking system. The process illustrated in FIG. 13 can be performed by, for example, the motion tracking system 1100 shown in FIG. 11. The process begins at block 1302. At block 1304 baseline data representing a baseline patient position is provided. For example, the detectors 102 can detect images of the patient and send that data to the detector processing interface 104 for determination of a baseline patient position. At block 1306 an imaging scan of the patient is begun by the scanner 108.

At block 1308 new patient movement data (for example, images, distance estimates, or the like) is acquired from the detectors. At block 1310 the new patient movement data from the detectors is analyzed to estimate a new patient position. For example, the various tracking controllers or filters 202 analyze the data from the detectors 102 to develop estimates of the new patient positioning, as described above. The tracking combination interface 204 then combines the estimates from the various tracking controllers or filters to generate one unitary patient positioning estimate, as described above.

At block 1312 the system analyzes the detector data and/or the patient position data from the tracking controllers or filters to estimate a quality of the movement data. For example, as described above, the deformation detectors 404 and internal consistency interface 402 can analyze data from the detectors 102 and/or tracking controllers or filters 202 to estimate a level of quality. At block 1314 tracking data is generated. For example, the tracking combination interface 204 generates tracking data based on a combination of the various estimates from the tracking controllers or filters 202.

At block 1316 the process determines whether the tracking quality is sufficient. For example, the veto controller 406 analyzes the data from the internal consistency controller 402 and deformation detectors 404, as described above, to determine whether a certain level of quality has been met and therefore whether a veto signal should be generated and sent to, for example, the image processing system 902. If the tracking quality is not sufficient, at block 1318 the process pauses or holds scanner acquisition and/or instructs the scanner 108 to acquire dummy scanner data. The process then proceeds back to block 1308 and acquires new patient movement data from detectors. If the tracking quality is determined to be sufficient at block 1316, then the process proceeds to block 1320. At block 1320 the process varies depending on whether the scan is complete. If the scan is not complete, the process moves to block 1322 and scanner data is acquired by the scanner 108. At block 1324 the image processing system 902 utilizes the scanner data from the scanner 108 and scanner image acquisition interface 904 to adjust the image data to compensate for patient movement based on the tracking data received from the detector processing interface 104. The process then proceeds back to block 1308 and acquires new patient movement data from the detectors. If the scan is determined to be complete at block 1320, then the process proceeds to block 1326 and the process is complete.

Figure 14:
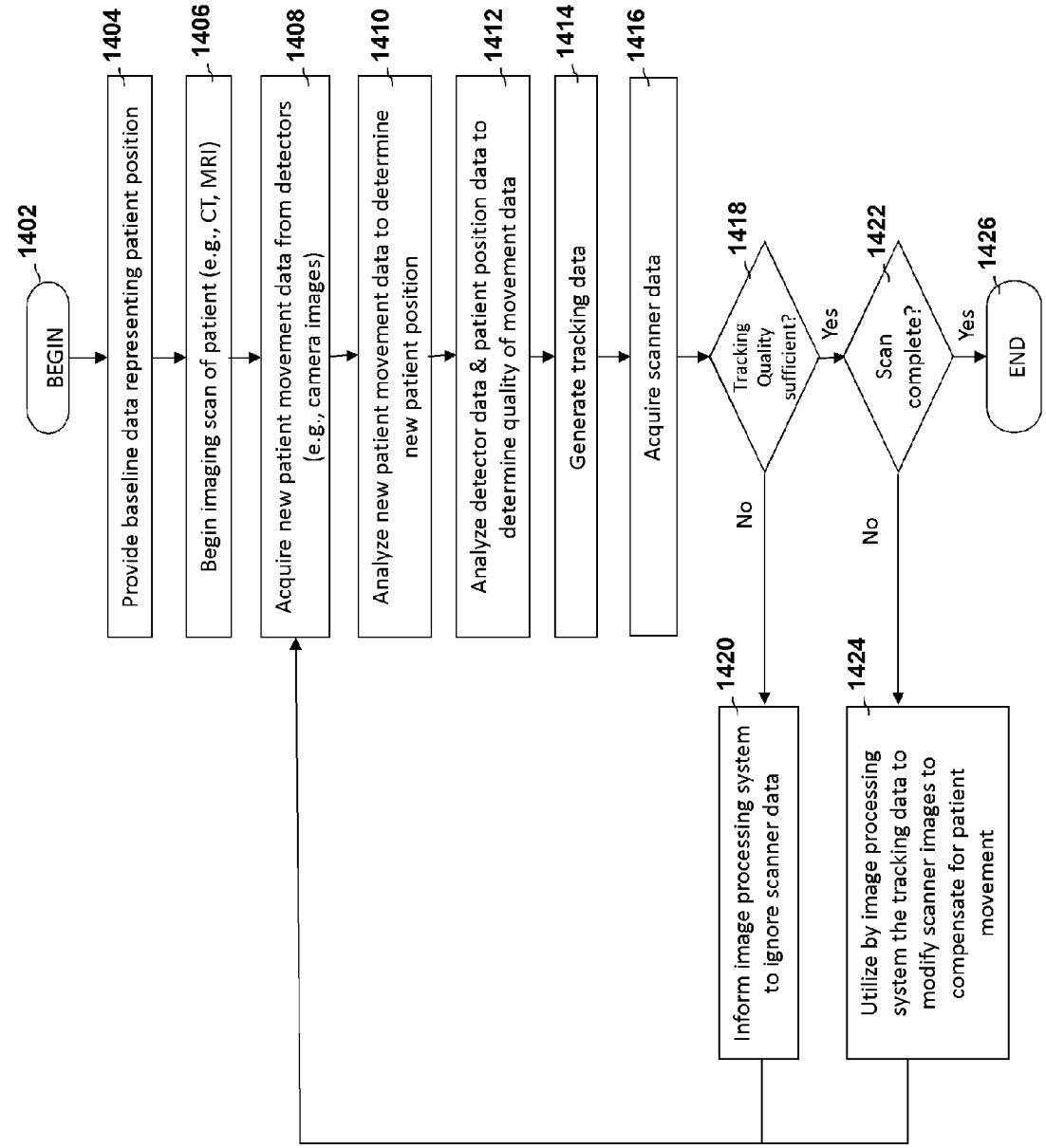
FIG. 14 depicts an embodiment of a process flow diagram illustrating an example of tracking and compensating for motion in biomedical imaging using a motion tracking system.

FIG. 14 depicts an embodiment of a process flow diagram illustrating an example of tracking and compensating for motion in biomedical imaging using a motion tracking system. The process embodied in FIG. 14 illustrates another example of tracking patient movement and analyzing the quality of the movement tracking data. If the movement tracking data is not of sufficient quality, then the process is configured to ignore scanner data. The process begins at block 1402. At block 1404 baseline data representing the patient's baseline position is provided. For example, the detectors 102 of the motion tracking system 1100 detect patient movement data and send that data to the detector processing interface 104. The detector processing interface 104 uses its tracking controllers or filters 202 and tracking combination interface 204 to determine the baseline patient positioning estimate.

At block 1406 the imaging scan of the patient is begun. At block 1408 new patient movement data from the detectors 102 is acquired. At block 1410, the detector processing interface 104 analyzes the new patient movement data to determine a new patient position estimate. The detector processing interface 104 determines the new patient positioning estimate using its tracking controllers or filters 202 and tracking combination interface 204 as described above. At block 1412 the detector processing interface 104 analyzes the detector data and/or the new patient position estimate data to determine a quality of the overall patient movement estimate data. For example, the detector processing interface 104 utilizes the internal consistency controller 402 and deformation detectors 404 to analyze a quality of the data from the detectors 102 and tracking controller 202, as described above.

At block 1414 tracking data is generated. The tracking data is generated by the tracking combination interface 204 to be sent to the image processing system 902, as described above. At block 1416 the scanner 108 acquires scanner data. At block 1418 the process varies depending on whether the tracking quality is sufficient. For example, the veto controller 406 determines whether the quality as estimated by the deformation detectors 404 and internal consistency controller 402 exceeds a certain quality level. If the tracking quality is not sufficient, the process moves to block 1420, wherein the image processing system 902 is instructed to ignore the relevant scanner data. The process then moves back to block 1408 and acquires new patient movement data from the detectors. The process repeats in this fashion until the tracking quality is found to be sufficient. When the tracking quality is found to be sufficient at block 1418, the process moves to block 1422. At block 1422 the process varies depending on whether the scan is complete. If the scan is not complete the process moves to block 1424. At block 1424 the image processing system 902 utilizes the tracking data from the detector processing interface 104 to compensate for patient movement in the acquired images. The process then moves back to block 1408 and acquires new patient movement data from detectors. The process continues in this fashion until the imaging scan is complete. When the scan is complete at block 1422 the process moves to block 1426 and the process is complete.

Figure 15:
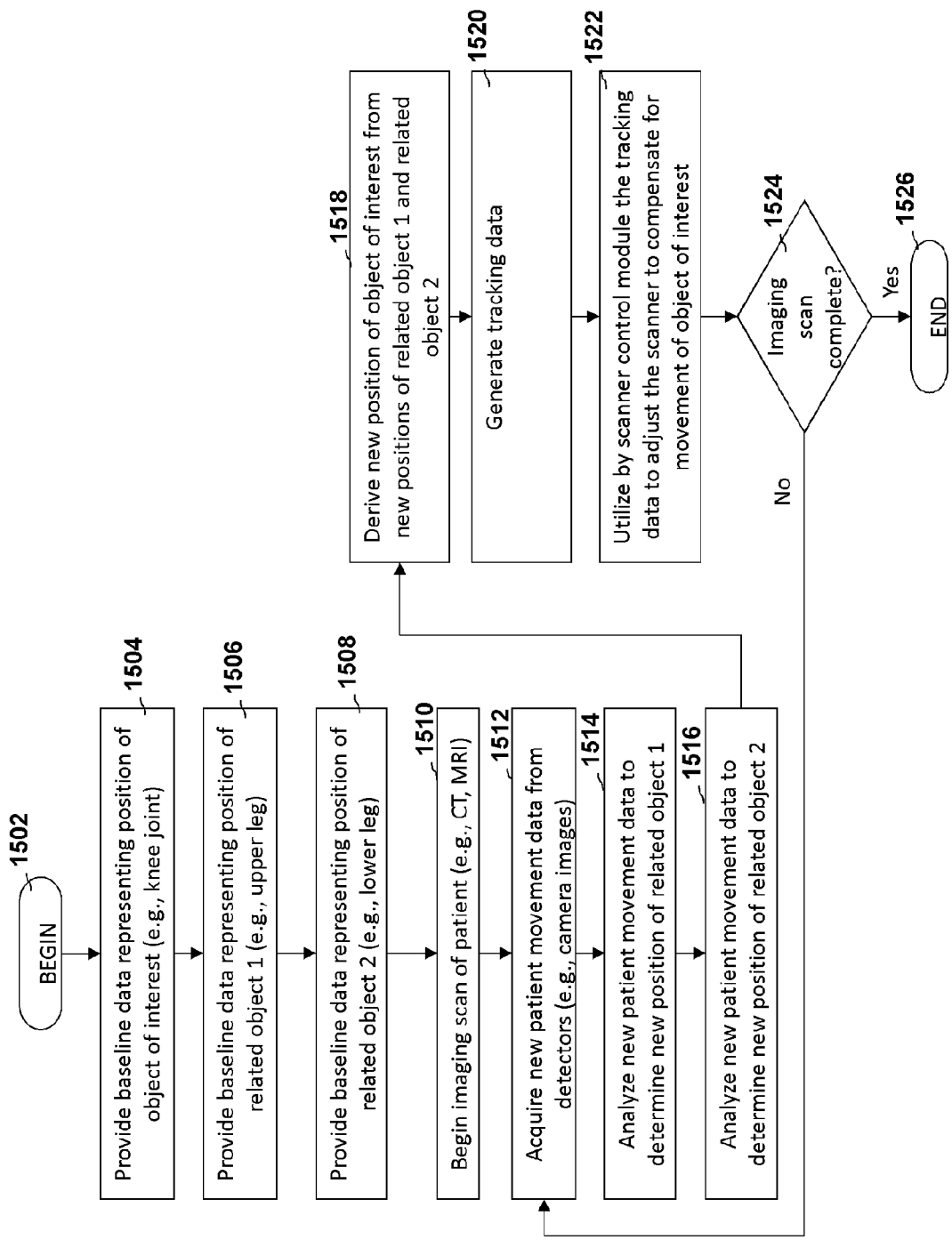
FIG. 15 depicts another embodiment of a process flow diagram illustrating an example of tracking and compensating for motion in biomedical imaging using a motion tracking system.

FIG. 15 depicts another embodiment of a process flow diagram illustrating an example of tracking and compensating for motion in biomedical imaging using a motion tracking system. The process shown in FIG. 15 illustrates an example of tracking a jointed object, such as a human knee joint. The process shown in FIG. 15 can be performed by various motion tracking systems, for example the motion tracking system 200 shown in FIG. 2. The process begins at block 1502. At block 1504 baseline data representing the position of an object of interest is provided. For example, the object of interest may be a knee joint of a human being. At blocks 1506 and 1508 baseline data is provided representing positions of a first related object and a second related object. For example, at block 1506 baseline positional data representing a position of the patient's upper leg is provided. At block 1508, baseline positional data representing the position of the patient's lower leg is provided. The baseline positional data provided in blocks 1504, 1506, and 1508 can be provided as described above using detectors 102 and a detector processing interface 104.

At block 1510 an imaging scan of the patient/object of interest is begun. At block 1512 new patient movement data is acquired from the detectors, such as the detectors 102 shown in FIG. 2. At block 1514 the new patient movement data is analyzed to determine the new position of related object 1, such as the patient's upper leg. At block 1516 the new patient movement data is analyzed to estimate the new position of related object 2, such as the patient's lower leg. The new positions of related objects 1 and 2 can be determined as described above using, for example, the detector processing interface 104 shown in FIG. 2.

At block 1518 a new position of the object of interest is derived from the new positions of related objects 1 and 2. For example, a knee joint position or orientation can be derived from an estimated positioning of the patient's upper leg and lower leg. At block 1520, tracking data is generated to enable the scanner to track movement of the object of interest, such as the patient's knee joint. The tracking data can be generated by the detector processing interface 104 as described above.

At block 1522, a scanner controller, such as the scanner controller 106 shown in FIG. 2, utilizes the tracking data to adjust the scanner in real time to compensate for movement of the object of interest. At block 1524 the process varies depending on whether the imaging scan is complete. If the imaging scan is not complete, the process goes back to block 1512 and acquires new patient movement data from the detectors. The process continues in this fashion until the imaging scan is complete. If the imaging scan is complete, the process moves to block 1526, and the process is complete.

Figure 16:
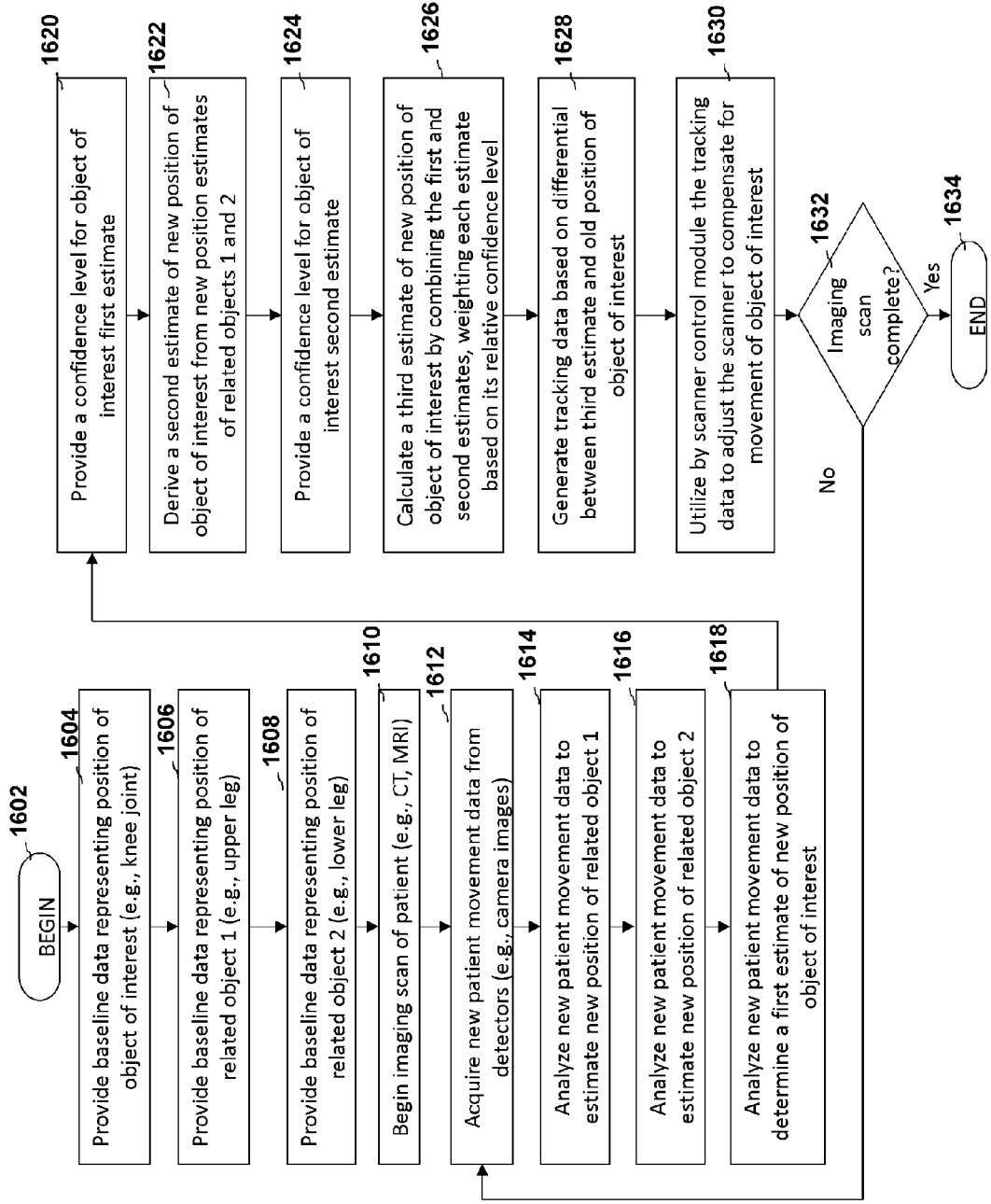
FIG. 16 depicts an embodiment of a process flow diagram illustrating an example of tracking and compensating for motion in biomedical imaging using a motion tracking system.

FIG. 16 depicts an embodiment of a process flow diagram illustrating an example of tracking and compensating for motion in biomedical imaging using a motion tracking system. The process shown in FIG. 16 can be used, for example, to increase an accuracy of tracking an object of interest by additionally tracking related objects and combining estimates based on directly tracking the object of interest and estimates derived from tracking the related objects. The process begins at block 1602. At block 1604 baseline data representing the position of the object of interest is provided. For example, when tracking a knee joint of a human being, baseline positional information of the knee joint is provided. The baseline positional information can be provided by, for example, utilizing the motion tracking system 200 shown in FIG. 2. At blocks 1606 and 1608 baseline data representing position estimates of two related objects are provided. At block 1606 an estimate of a position of a first related object, such as the patient's upper leg, is provided. At block 1608 a position estimate of a related object 2 is provided, such as the patient's lower leg.

At block 1610 the imaging scan of the patient is begun. At block 1612 new patient movement data is acquired from the detectors 102. At block 1614 the new patient movement data is analyzed to estimate a new position of related object 1. For example, the detector processing interface 104 shown in FIG. 2 is used as described above to estimate the new position of the patient's upper leg. At block 1616 the new patient movement data is analyzed to estimate the new position of related object 2. For example, the detector processing interface 104 is used to estimate a position of the patient's lower leg. At block 1618 the patient movement data is analyzed to determine a first estimate of the new position of the object of interest. For example, the detector processing interface 104 is used as described above to estimate the new position of the patient's knee joint.

At block 1620 a confidence level is provided for the first estimate of the position of the object of interest. The confidence level can be a weighting factor, a probability, or another measure related to accuracy. The confidence level can be an indication of how accurately the detector processing interface has estimated the new position of the object of interest.

At block 1622 a second estimate of the new position of the object of interest is calculated by deriving the estimate from the new position estimates of related objects 1 and 2. For example, when tracking a knee joint, an estimate of the position or orientation of the knee joint can be derived from estimates of the patient's upper leg and lower leg positioning. At block 1624 the system provides a confidence level for the second estimate of the object of interest's position. The confidence level can be an error estimate, a probability, or other measure related to accuracy.

At block 1626 a third estimate of the new positioning of the object of interest is calculated by combining the first and second estimates. In some embodiments, the first and second estimates are combined with a simple average or weighted average, weighting each estimate based on its relative confidence level. In other embodiments, the first estimate and second estimate are combined in a winner takes all approach. For example, the estimate with the highest relative confidence level may be used and the other one discarded. In other examples, the first estimate and second estimate can be combined using Bayesian probability or other statistical approaches. At block 1628 the system generates tracking data based on a differential between the third estimate of the patient's new positioning and the old or prior positioning estimate of the object of interest. This tracking data can be generated, for example, by the tracking combination controller 204 as described above.

At block 1630 the scanner controller utilizes the tracking data to adjust the scanner to compensate for movement of the patient or object of interest. At block 1632 the process varies depending on whether the imaging scan is complete. If the imaging scan is not complete, the process goes back to block 1612 and acquires new patient movement data from the detectors. The process continues in this fashion until the imaging scan is complete. When the imaging scan is complete at block 1632, the process proceeds to block 1634 and is complete.

In some embodiments of motion tracking systems, the motion tracking system is configured to associate subject motion or movement tracking data with image data acquired from a scanner and to display the tracking data along with the associated image data by, for example, overlaying the tracking data over the image data. For example, FIG. 18 illustrates an embodiment of a scanner image 1802 combined with a tracking data overlay 1804 and a pictorial tracking overlay 1806. The scanner image 1802 is, for example, a magnetic resonance image acquired using a magnetic resonance scanner, such as the scanner 108 shown in FIG. 17. While the scanner image 1802 shown in FIG. 18 depicts an entire human body, the scanner image 1802 can be an image of any object being scanned, for example, a human brain, a knee joint, or the like.

Figure 17:
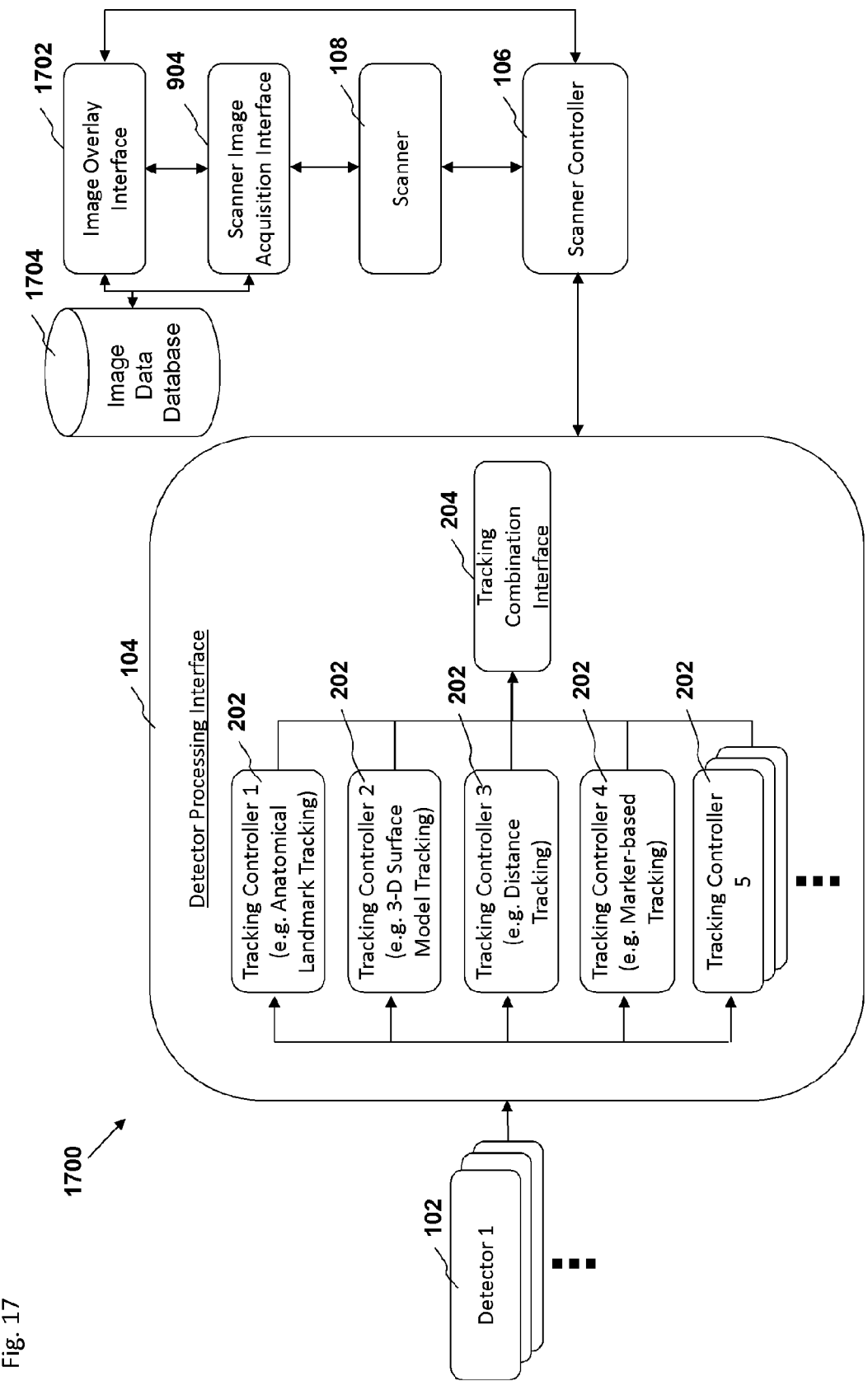
FIG. 17 is a block diagram depicting an embodiment of a motion tracking system.
Figure 18:
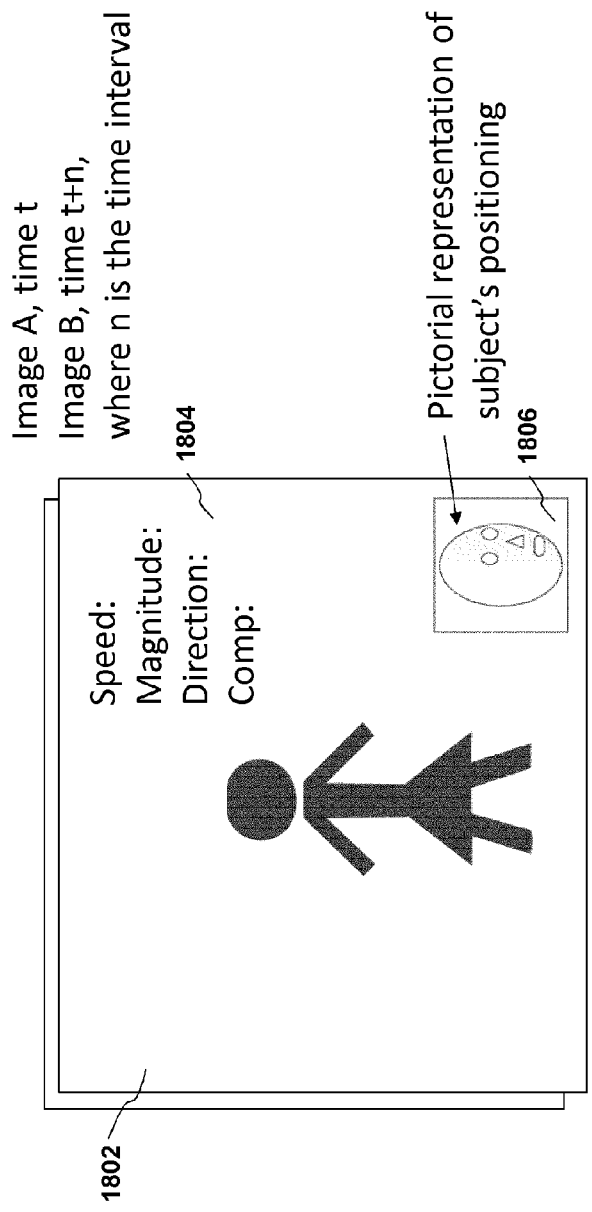
FIG. 18 illustrates an embodiment of a scanner image combined with a tracking data overlay and a pictorial tracking overlay.

The tracking data overlay 1804 shown in FIG. 18 can be configured to display information related to motion of the subject or object of interest that occurred during the scan represented by the scanner image 1802 and that was tracked by a motion tracking system, such as the motion tracking system 1700 shown in FIG. 17. For example, the tracking data overlay 1804 can be configured to display a speed or velocity of tracked movement. The speed or velocity can be displayed in numerical form (for example, 10 mm/sec), or in pictorial form, for example, by displaying a horizontal bar having a relatively long length to represent a relatively fast speed or a relatively short length to represent a relatively slow speed, or by displaying a graph representing the temporal evolution of motion during the scan. The tracking data overlay 1804 can also be configured to display a magnitude of tracked movement. The magnitude can be displayed in numerical form (for example, 10 mm), or in pictorial form, for example, by displaying a horizontal bar having a relatively long length to represent a relatively large movement or a relatively short length to represent a relatively small movement.

The tracking data overlay 1804 can additionally be configured to display a direction of tracked movement. The direction can be displayed in numerical or pictorial form. For example, the direction can be depicted as numerical values representing the three translations and three rotations in the detector and/or scanner coordinate systems. In some embodiments, the direction can be depicted using a pictorial representation or representations of a rotated or translated coordinate system or of a motion path of the tracked subject (for example, using the motion indicators 2104 shown in FIGS. 21, 22A-22D, and 23A-23C).

In some embodiments, a pictorial representation can be configured to show a speed, magnitude, or direction of tracked motion, or any combination thereof. For example, an arrow, such as the motion indicator 2104 shown in FIG. 21, can be configured to display directions by the direction or directions the arrow or segments of the arrow are pointing, magnitude by lengths of the arrow segments, and/or velocity by a color or thickness of the arrow segments.

In some embodiments, the tracking data overlay 1804 can be configured to display absolute values, average values, median values, minimum values, maximum values, variance values, range values, and the like, or any combination thereof.

The tracking data overlay 1804 can also be configured to indicate whether or not motion compensation was applied to the scanner image 1802. For example, the tracking data overlay 1804 can be configured to display text, such as "Comp: ON" or "Comp: OFF" to indicate that motion compensation was or was not applied, respectively. The motion tracking system can alternatively be configured to display whether motion compensation was applied to the scanner image 1802 is various other ways. For example, a portion of the scanner image 1802, such as a border, a graphic, a bar, text, or the like, can be configured to be a different color depending on whether or not motion tracking was applied.

In some embodiments, a scanner image 1802 can be combined with multiple tracking data overlays 1804. For example, in a motion tracking system configured to adjust or update scanner parameters based on tracked motion more than one time during the creation of each scanner image 1802, the scanner image 1802 can be configured to display a separate tracking data overlay 1804 for each adjustment or update to the scanner parameters. Alternatively, the system can be configured to combine all adjustments or updates into one tracking data overlay 1804 by providing, for example, average values, median values, minimum values, maximum values, variance values, range values, or the like.

The pictorial tracking overlay 1806 shown in FIG. 18 can be configured to indicate pictorially the position of the subject or object of interest during the creation of the scanner image 1802. For example, the pictorial tracking overlay 1806 illustrates a human head turned slightly to the left. The positioning of the head shown in the pictorial tracking overlay 1806 can indicate, for example, the positioning of the subject's head at the beginning of scan illustrated by scanner image 1802, at the end of the scan, at the middle of the scan, or, for example, an average position of the subject's head during the scan.

In some embodiments, the pictorial tracking overlay 1806 can additionally or alternatively be configured to display motion that was tracked during the creation of scanner image 1802. For example, a series of semi-transparent depictions of a human head can be shown on top of one another but slightly translated or rotated with respect to each other to depict the tracked motion. In other examples, as illustrated in FIGS. 21, 22A-22D, and 23A-23C, various motion indicators 2104 can be configured to display tracked motion.

In some embodiments, a motion tracking system, such as the motion tracking system 1700 shown in FIG. 17, can be configured to display a video depiction of tracked motion. For example, the system can be configured to electronically display the scanner image 1802 with an animated pictorial tracking overlay 1806 showing the subject's tracked motion. If the system tracked a subject's head moving from right to left during creation of the scanner image 1802, then the pictorial tracking overlay 1806 can, for example, depict an animated head moving from right to left.

Although the pictorial tracking overlay 1806 illustrated in FIG. 18 shows a representation of a human head, in some embodiments the pictorial tracking overlay 1806 can alternatively include a representation of any other organ being scanned or even an arbitrary shape, cross, coordinate system axes depiction, or the like. In some embodiments, the pictorial tracking overlay 1806 can include a visual photographic image and/or video of the subject, for example, as acquired by one or more of the detectors 102.

Figure 21:
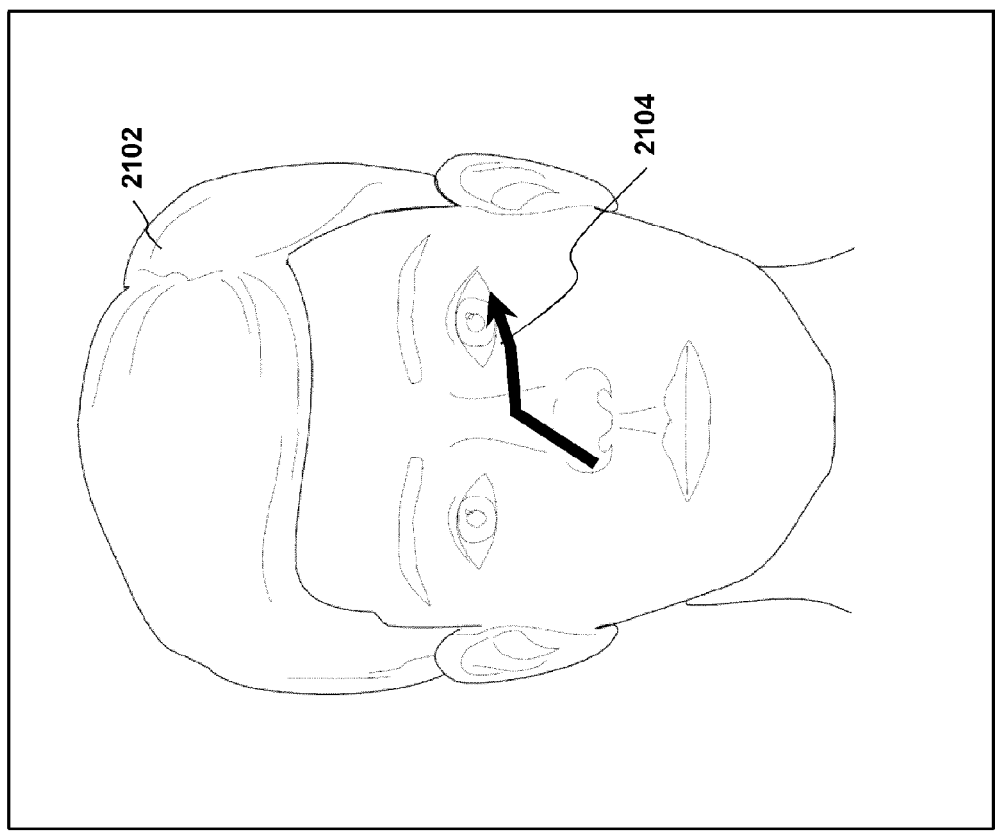
FIG. 21 illustrates an embodiment of a tracked motion display.
Figure 22D:
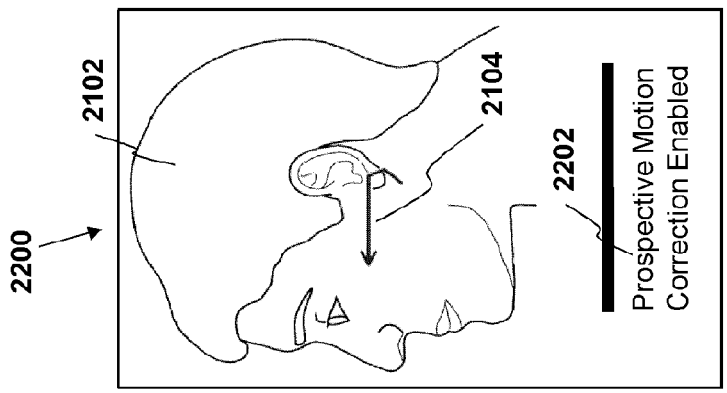
FIG. 22D illustrates an embodiment of a tracked motion display.
Figure 22C:
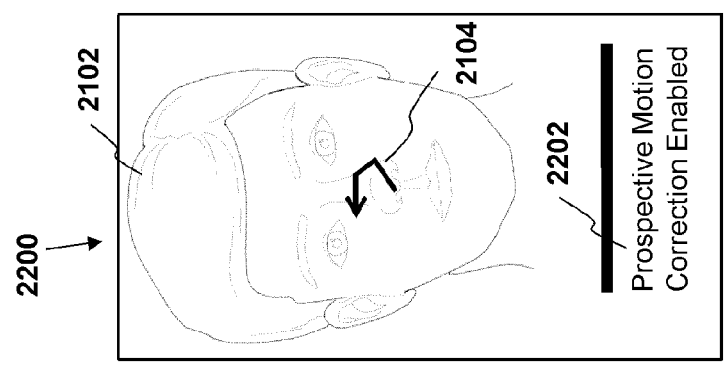
FIG. 22C illustrates an embodiment of a tracked motion display.
Figure 22B:
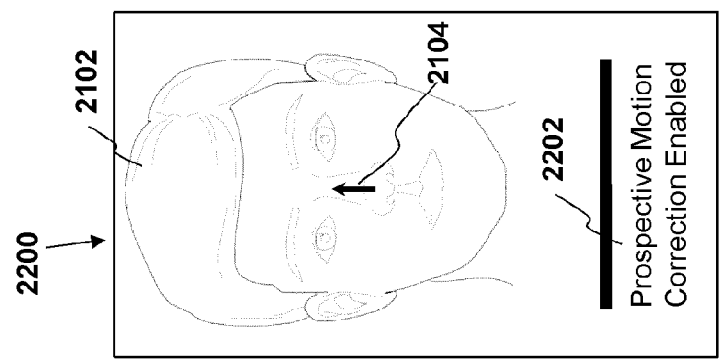
FIG. 22B illustrates an embodiment of a tracked motion display.
Figure 22A:
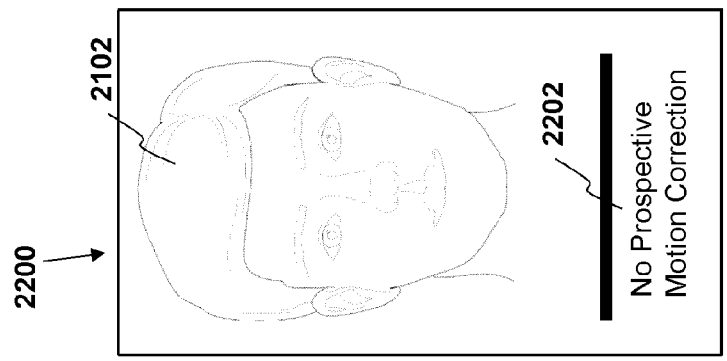
FIG. 22A illustrates an embodiment of a tracked motion display.

FIG. 21 illustrates an embodiment of a tracked motion display 2100. The tracked motion display 2100 includes a subject representation 2102 and a motion indicator 2104. The subject representation 2102 can be, for example, a representation of a human head or any other object of interest being scanned. The motion indicator 2104 comprises an arrow with multiple segments indicating motion that was tracked during a scan. For example, in this embodiment, the motion indicator 2104 is displaying that the patient rotated his or her head generally up and to the left during a scan. The tracked motion display 2100 can be used as a pictorial tracking overlay 1806 as described above. The tracked motion display 2100 can alternatively be displayed on a separate electronic display or on a separate printout.

FIGS. 22A-22D illustrate various embodiments of tracked motion displays 2200. The tracked motion displays 2200 include a subject representation 2102, a motion indicator 2104, and a compensation indicator 2202. In some embodiments, the tracked motion displays 2200 represent individual frames of an animated video showing tracked motion and whether or not motion compensation was applied. In other embodiments, the tracked motion displays 2200 are static displays associated with specific scanner images and displayed along with their associated scanner images by, for example, being used as a pictorial tracking overlay 1806 as described above or being displayed on an electronic display while a user is viewing the scanned images.

The compensation indicators 2202 are configured to display whether or not motion compensation was applied to the scanner image or images associated with each tracked motion display 2200. For example, if compensation was not applied, the compensation indicator 2202 is configured to be colored red and to say "No Prospective Motion Correction." If compensation was applied, the compensation indicator 2202 is configured to be colored green and to say "Prospective Motion Correction Enabled." In other embodiments, the compensation indicators 2202 can be configured to display whether motion compensation was applied in various other ways. For example, the compensation indicators 2202 can be a colored border or background that changes colors depending on whether motion compensation was applied.

The motion indicator 2104 is configured to indicate motion of the patient or object of interest that was tracked during the scan. In some embodiments, the motion indicator 2104 is configured to only display motion tracked during creation of the scanned image associated with that tracked motion display 2200. In other embodiments, the motion indicator 2104 is configured to be cumulative. For example, in some embodiments, the motion indicator 2104 is configured to display motion tracked during creation of the scanned image associated with that tracked motion display 2200, but also to display motion tracked during prior scanned images. In some embodiments, the subject representation 2101 is also configured to display tracked motion. For example, in FIG. 22C, the subject representation 2101 is shown tilted to the right, indicating the patient had his or her head tilted to the right during the creation of the scanned image or images associated with that tracked motion display 2200.

Figure 23C:
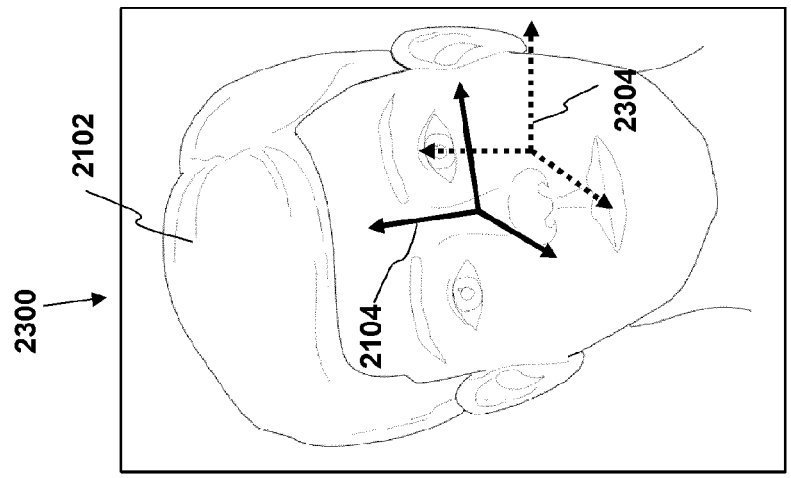
FIG. 23C illustrates an embodiment of a tracked motion display.
Figure 23B:
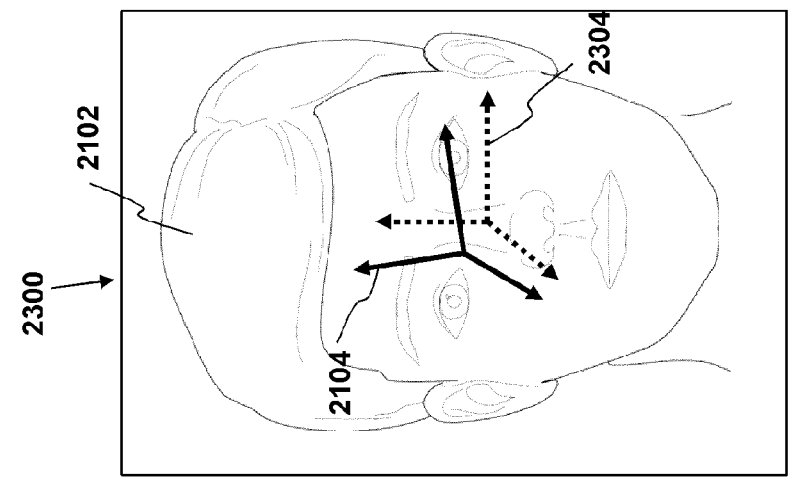
FIG. 23B illustrates an embodiment of a tracked motion display.
Figure 23A:
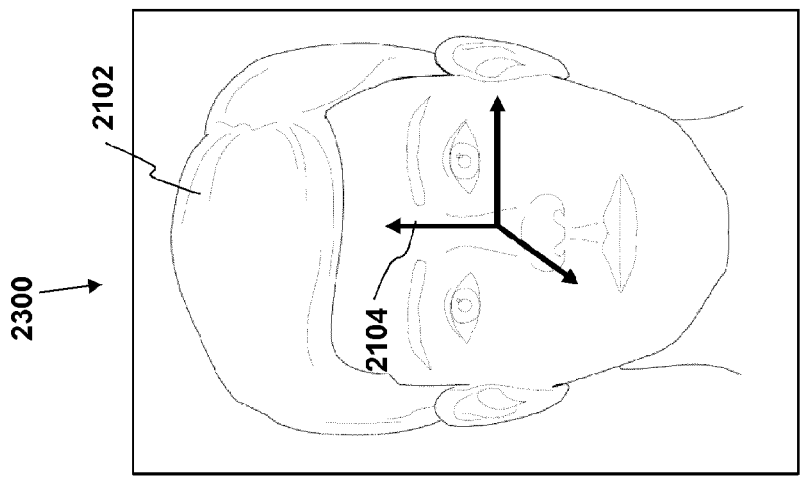
FIG. 23A illustrates an embodiment of a tracked motion display.

FIGS. 23A-23C illustrate additional embodiments of tracked motion displays 2300. The tracked motion displays 2300 include a subject representation 2102, a motion indicator 2104, and a reference indicator 2304. The motion indicators 2104 comprise a representation of coordinate system axes configured to show all three translations and all three rotations of the object of interest through rotations and/or translations of the motion indicators 2104. The reference indicator 2304 is configured to show where the patient's head or other object of interest was located at the start of a scan. In some embodiments, as shown in FIG. 23B, the subject representation 2102 remains static, along with the reference indicator 2304, and only the motion indicator 2104 moves to display tracked motion. In other embodiments, as shown in FIG. 23C, both the subject representation 2102 and motion indicator 2104 move to display tracked motion. In some embodiments, the motion indicator 2104 and/or reference indicator 2304 are displayed using different colors to allow a user to more easily differentiate between them. For example, as shown in FIGS. 23A-23C, the motion indicator 2104 is shown using a red color and the reference indicator 2304 is shown using a blue color. In some embodiments, the indicators are illustrated using different line styles to allow a user to more easily differentiate between them. For example, as shown in FIGS. 23A-23C, the motion indicator 2104 is shown using solid lines and the reference indicator 2304 is shown using dashed lines. In various embodiments, motion indicators, such as those shown in FIGS. 21, 22A-22D, and 23A-23C, can be configured to be displayed using a different color than the subject representation to allow a user to more easily differentiate between the subject representation and motion indicator. For example, the subject representations in various figures are illustrated as black, while the motion indicators are illustrated as blue or red.

FIG. 17 is a block diagram depicting an embodiment of a motion tracking system 1700. The motion tracking system 1700 comprises one or more detectors 102, a detector processing interface 104, a scanner controller 106, a scanner 108, a scanner image acquisition interface 904, an image overlay interface 1702, and an image data database 1704. The detector processing interface further comprises several tracking controllers or filters 202 and a tracking combination interface 204, as described above and illustrated in, for example, motion tracking system 200. The motion tracking system 1700 operates similarly to the motion tracking system 200 shown in FIG. 2, with the addition of the scanner image acquisition controller 904, image overlay interface 1702, and image data database 1704, as described below.

Although motion tracking system 1700 is illustrated using multiple tracking controllers or filters 202 utilizing both markerless tracking techniques (for example, anatomical landmark tracking, distance tracking, or the like) and marker-based tracking techniques, the concepts described herein relating to image overlay techniques can be applied to any motion tracking system, including, but not limited to, systems using markerless tracking controllers, tracking controllers utilizing markers, or any combination thereof. The image overlay techniques described herein can additionally be used with motion tracking systems that utilize only one method of tracking and therefore do not comprise a tracking combination interface 204.

In operation, the scanner controller 106 shown in FIG. 17 receives tracking data describing tracked motion of the object of interest from the detector processing interface 104. The scanner controller 106 optionally uses this tracking data to adjust one or more parameters of the scanner 108 to compensate for the tracked motion. The scanner controller 106 additionally sends the tracking data and an indicator of whether or not the scanner controller 106 adjusted the scanner 108 for the tracked motion to the image overlay interface 1702. The image overlay interface 1702 utilizes the tracking data and indicator from the scanner controller 106 to generate data representing, for example, the tracking data overlay 1804 and/or the pictorial tracking overlay 1806 shown in FIG. 18, as described above.

In some embodiment, the image overlay interface 1702 communicates with the scanner image acquisition interface 904 to apply one or more tracking overlays to the scanner images acquired by the scanner image acquisition interface 904. In some embodiments, the scanner image acquisition interface 904 sends acquired scanner images to the image data database 1704 for later retrieval and display. The image overlay interface 1702 can additionally be configured to send data representing, for example, the tracking data overlay 1804 and/or the pictorial tracking overlay 1806, to the image data database 1704 and to associate this overlay data with the acquired scanner image or images in the database to which it should be applied. Scanner images can be retrieved from the image data database 1704 along with the associated overlay data to be, for example, printed, displayed on an electronic display device, transmitted through a network for display at a remote terminal, or the like.

Figure 19:
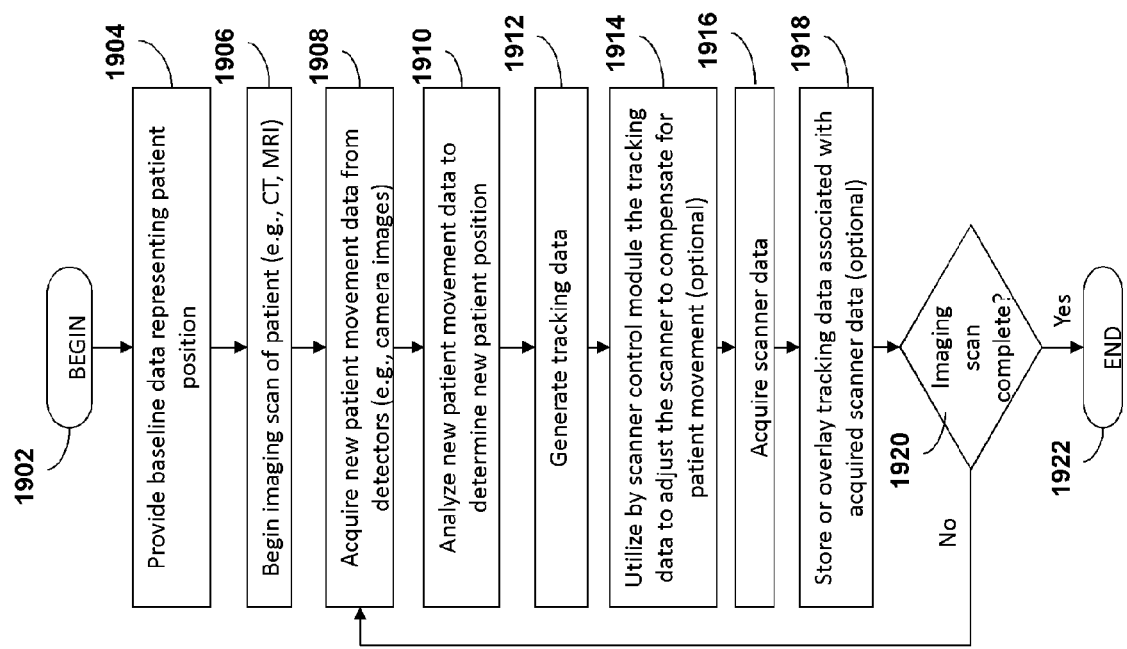
FIG. 19 depicts an embodiment of a process flow diagram illustrating an example of tracking and compensating for motion in biomedical imaging using a motion tracking system.

FIG. 19 depicts an embodiment of a process flow diagram illustrating an example of tracking and compensating for motion in biomedical imaging using a motion tracking system. This embodiment additionally illustrates an example of storing and/or overlaying tracking data for display along with acquired scanner images. At block 1902 the process begins. At block 1904 the system provides baseline data representing a patient position. For example, the detectors 102 as shown in the motion tracking system 1700 of FIG. 17 acquire information about a subject, such as images of the subject, and send this data to the detector processing interface 104. The detector processing interface 104 is configured to analyze this data and determine a baseline positioning of the patient or the object of interest. At block 1906 a scanner, such as the scanner 108 of the motion tracking system 1700, begins an imaging scan of the patient. For example, an MRI scanner begins a magnetic resonance imaging scan of the patient.

At block 1908 the detectors acquire new patient movement data. For example, the detectors acquire new images, camera frames, distance estimates, or the like of the patient or the object of interest. At block 1910 the system analyzes the new patient movement data to estimate a new patient positioning. For example, the data from the detectors 102 is analyzed by each of the tracking controllers or filters 202 as described above, and each tracking controller 202 generates an estimate of the new patient position. The estimates from the various tracking controllers or filters 202 are then fed into the tracking combination interface 204. The tracking combination interface 204 combines the various estimates from the tracking controllers or filters 202 and generates a single estimate to send to the scanner controller 106. At block 1912 the tracking combination interface generates tracking data containing the single estimate derived from the various estimates from the tracking controllers or filters 202. At block 1914 the scanner controller optionally utilizes the tracking data from the tracking combination interface to adjust the scanner to compensate for patient movement. For example, the scanner controller 106 adjusts in real time scan planes, locations, or orientations of the scanner. In some cases the scanner controller may not adjust the scanner, because, for example, a veto signal indicates the current tracking data is unreliable.

At block 1916, scanner data is acquired. For example, the scanner image acquisition interface 904 shown in FIG. 17 receives data from the scanner 108 representing an image of the subject or object of interest. At block 1918, tracking data associated with the acquired scanner data is stored in a database and associated with the scanner data and/or overlaid onto an image generated by the scanner image acquisition interface 904. For example, the image overlay interface 1702 shown in FIG. 17 associates tracking data received from the scanner controller 106 with the appropriate image data in the image data database 1704 and/or generates data describing a tracking overlay, as described above.

At block 1920 the process varies depending on whether the imaging scan is complete. If the imaging scan is not complete, the process returns to block 1908 and acquires new patient movement data from the detectors. This process continues throughout the imaging scan to continuously adjust the scanner based on patient motion and to store tracking data to be overlaid onto the resulting scanner images. When the imaging scan is complete, the process moves from block 1920 to the end of the process at block 1922.

Figure 20:
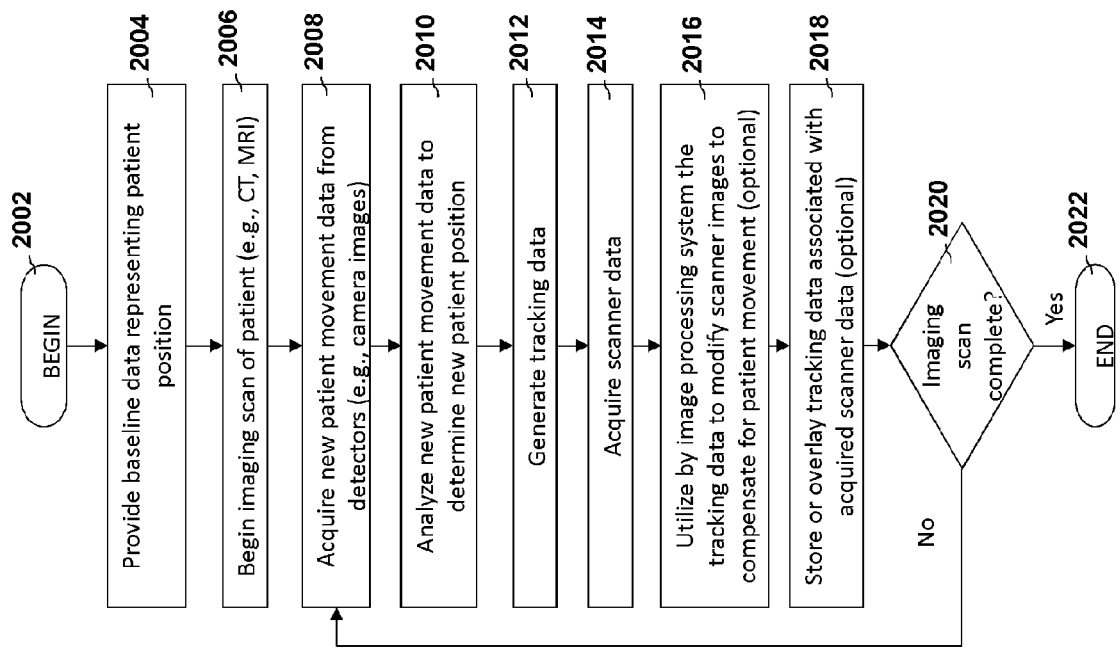
FIG. 20 depicts an embodiment of a process flow diagram illustrating an example of tracking and compensating for motion in biomedical imaging using a motion tracking system.

FIG. 20 depicts an embodiment of a process flow diagram illustrating an example of tracking and compensating for motion in biomedical imaging using a motion tracking system. This embodiment additionally illustrates an example of storing and/or overlaying tracking data for display along with acquired scanner images. The process shown in FIG. 20 can be implemented by, for example, the motion tracking system 900 shown in FIG. 9. At block 2002 the process begins. The system provides baseline data representing a patient's pre-scan position at block 2004. For example, detectors 102 detect information, such as images of a patient or object of interest, and send this information to a detector processing interface 104. The detector processing interface 104 uses various tracking controllers or filters 202 and a tracking combination interface 204, as described above, to then determine a baseline positioning of the patient or object of interest. At block 2006 the imaging scan of the patient or object of interest is begun.

At block 2008 new patient movement data, for example images, distance estimates, or the like, is acquired using the detectors 102. At block 2010 the new patient movement data is analyzed and compared to the baseline patient data to determine a new patient positioning estimate as described above. Block 2010 is performed by, for example, the detector processing interface 104 shown in FIG. 10. At block 2012 the system generates motion tracking data. The motion tracking data can be generated by, for example, the tracking combination interface 204 shown in FIG. 10, and describes the motion estimate generated by the tracking combination interface 204. At block 2014 scanner data is acquired. For example, the scanner 108 shown in FIG. 10 acquires scanner image data and sends the data to the scanner image acquisition interface 904.

At block 2016 the image processing system, such as the image processing system 902 shown in FIG. 10, optionally utilizes the acquired scanner data and generated tracking data to modify scanner images to compensate for patient movement. The image processing system 902 may not modify the scanner images in some cases, because, for example, a veto signal indicates the tracking data is unreliable.

At block 2018, tracking data associated with the scanner images from the scanner image acquisition interface 904 is stored in a database and associated with the scanner images and/or overlaid onto the scanner images. For example, the image processing system 902 may further comprise an image overlay interface 1702 and/or image data database 1704, as shown in FIG. 17, to generate and/or store data representing tracking overlays associated with scanner images, such as the tracking data overlay 1804 and/or pictorial tracking overlay 1806 shown in FIG. 18.

At block 2020 the process varies depending on whether the imaging scan is complete. If the imaging scan is not complete the process proceeds back to block 2008 and acquires new patient movement data from the detectors 102. The process then continues as described above. This process continues throughout the imaging scan to continuously modify the scanner images based on patient motion and to store tracking data to be overlaid onto the scanner images. If the imaging scan is complete at block 2020, the process proceeds to block 2022 and the process is complete.

Detector Positions

For any of the embodiments disclosed herein, one of ordinary skill in the art will appreciate that there can be a number of ways to position the detectors with respect to the medical imaging scanner. Disclosed below are several embodiments for positioning detectors with respect to the medical imaging scanner.

Figure 33:
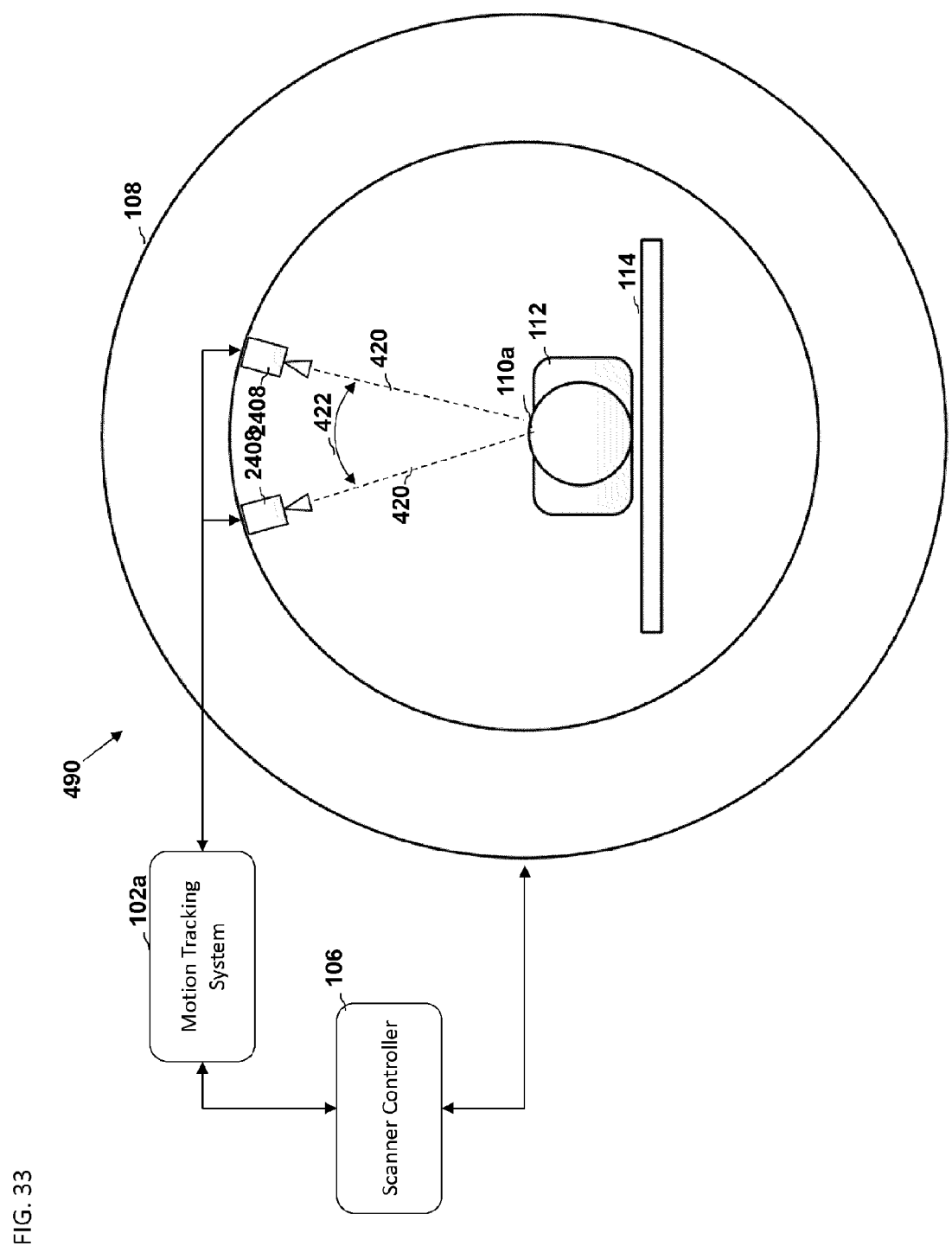
FIG. 33 is another embodiment of a schematic diagram illustrating a front view of a medical imaging scanner as part of a motion compensation system.

Any of the embodiments disclosed herein can be combined with the system illustrated in FIG. 24. FIG. 24 is a schematic diagram illustrating a side view of the medical imaging scanner 108 as part of the motion compensation system 2400. The motion compensation system 2400 is similar to the motion compensation system 100 illustrated in FIG. 1. However, the motion compensation system 100, as described above, illustrates three detectors 102. In the motion compensation system 2400, the detectors 2408 are positioned at a 90 degree angle 422 (also referred to as a scissor angle) to each other. The detectors 2408 of the motion compensation system 2400 are configured to view the landmark 110a along two different lines of sight 420. The motion compensation system 2400 illustrates that the detectors 2408 can be positioned in various ways, as long as each detector 2408 views the landmark 110a along a different line of sight. The angle 422 can vary and can be larger or smaller. In an embodiment, the angle 422 can be between 100 degrees and 70 degrees. In an embodiment, the angle 422 can be between 100 degrees and 20 degrees. In an embodiment, the angle 422 can be 30 degrees. For example, FIG. 33 illustrates a motion compensation system 490 similar to the motion compensation system 2400, except that the angle 422 is 30 degrees. In other embodiments, the angle can be various other angles, as long as the two lines of sight 420 are different.

Figure 25:
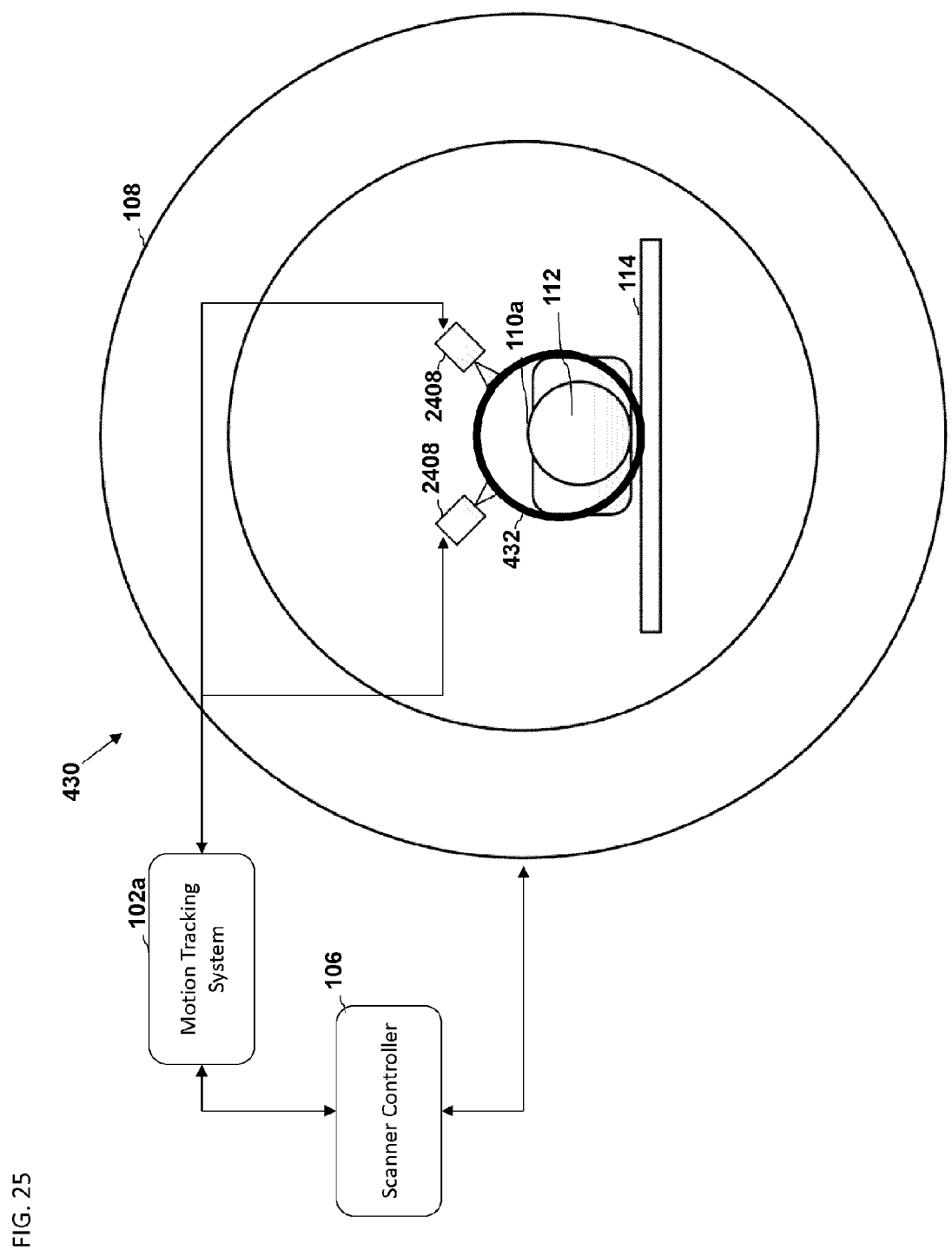
FIG. 25 is another embodiment of a schematic diagram illustrating a front view of a medical imaging scanner as part of a motion compensation system.
Figure 26:
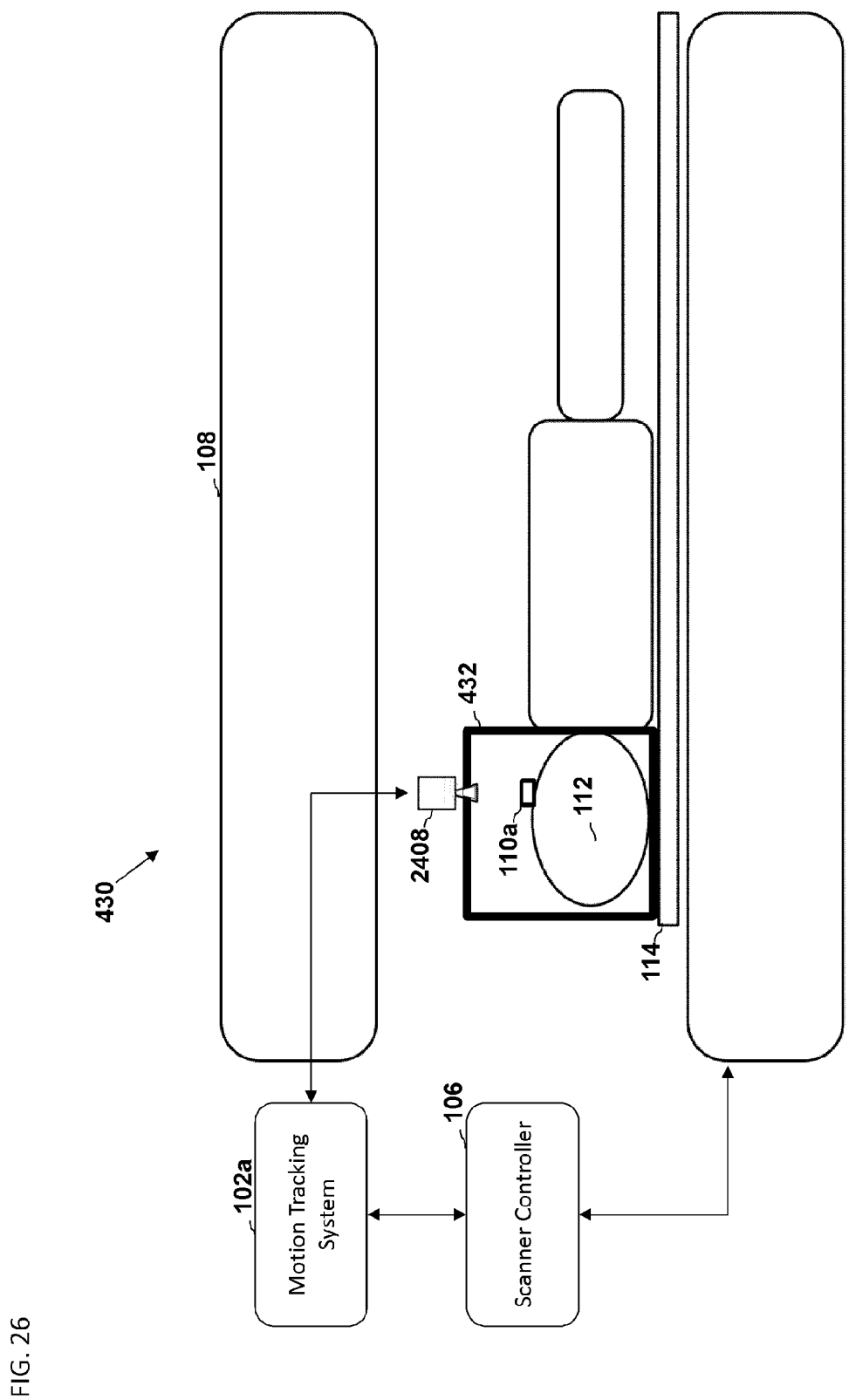
FIG. 26 is a schematic diagram illustrating a side view of the medical imaging scanner as a part of the motion compensation system of FIG. 25.

Any of the embodiments disclosed herein can be combined with the system illustrated in FIGS. 25 and 26. FIG. 25 is another embodiment of a schematic diagram illustrating a front view of a medical imaging scanner 108 as part of a motion compensation system 430. FIG. 26 is a schematic diagram illustrating a side view of the medical imaging scanner 108 as a part of the motion compensation system 430. The motion compensation system 430 is similar to the motion compensation system 100 illustrated in FIG. 1. However, the motion compensation system 430 further comprises a head cage or head coil 432 configured to be positioned around a patient's head. In certain medical imaging tasks, such as certain MRI head scans, a head cage 432 can be utilized and positioned around the patient's head. The head cage can make it more difficult for a detector 2408 to image the landmark 110a if the detectors 2408 were mounted to the bore of the scanner body 108. Accordingly, the motion compensation system 430 comprises two detectors 2408 mounted to the head cage instead of the scanner body. The detectors 2408 and motion tracking system 102 are configured to operate similarly to as described above. The term head cage as utilized herein may be used to describe a device configured to help position the head of a patient during an MRI scan. The term head cage may also refer to a head coil device configured to wrap around a patient's head to perform MRI scanning functions.

Figure 27:
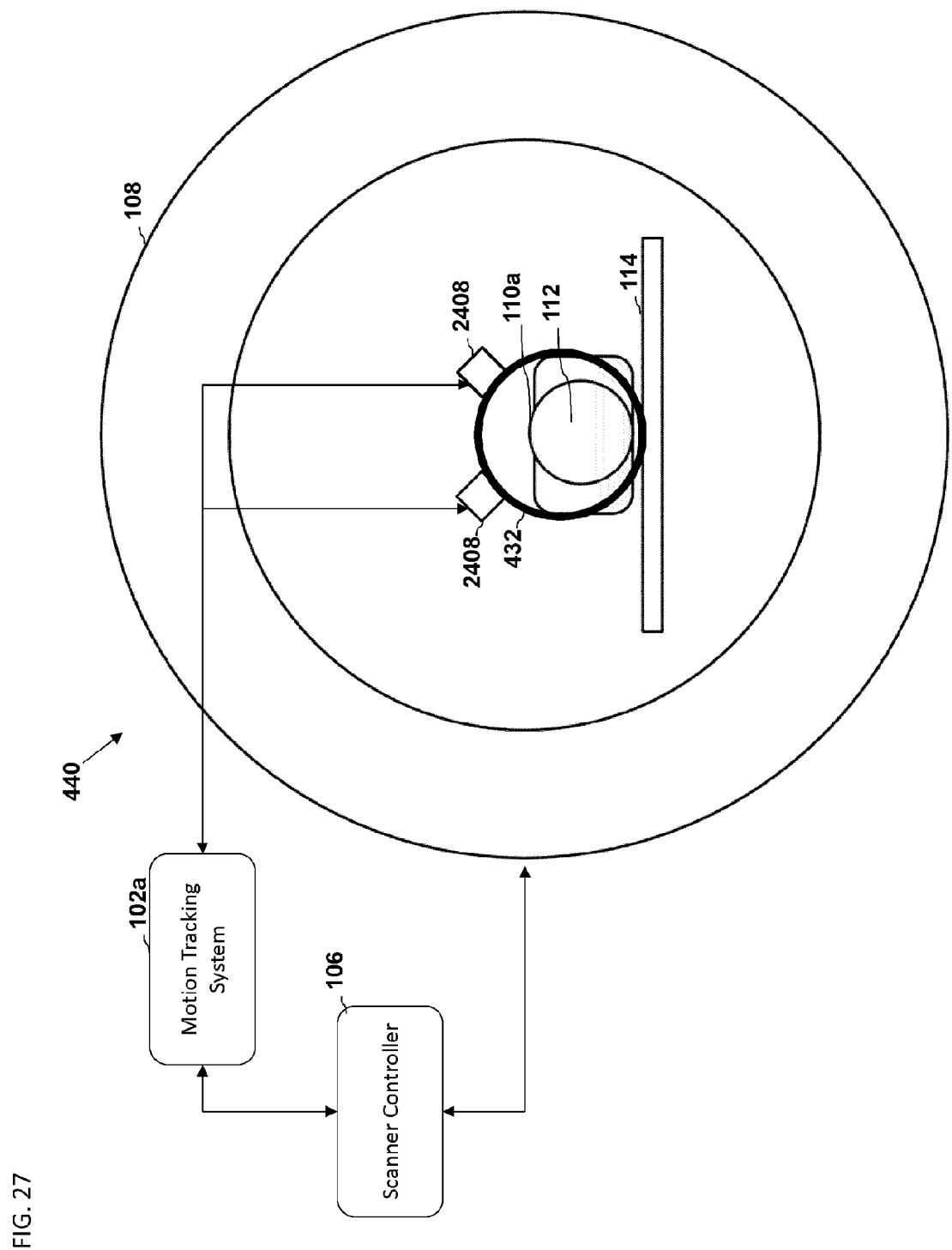
FIG. 27 is another embodiment of a schematic diagram illustrating a front view of a medical imaging scanner as part of a motion compensation system.
Figure 28:
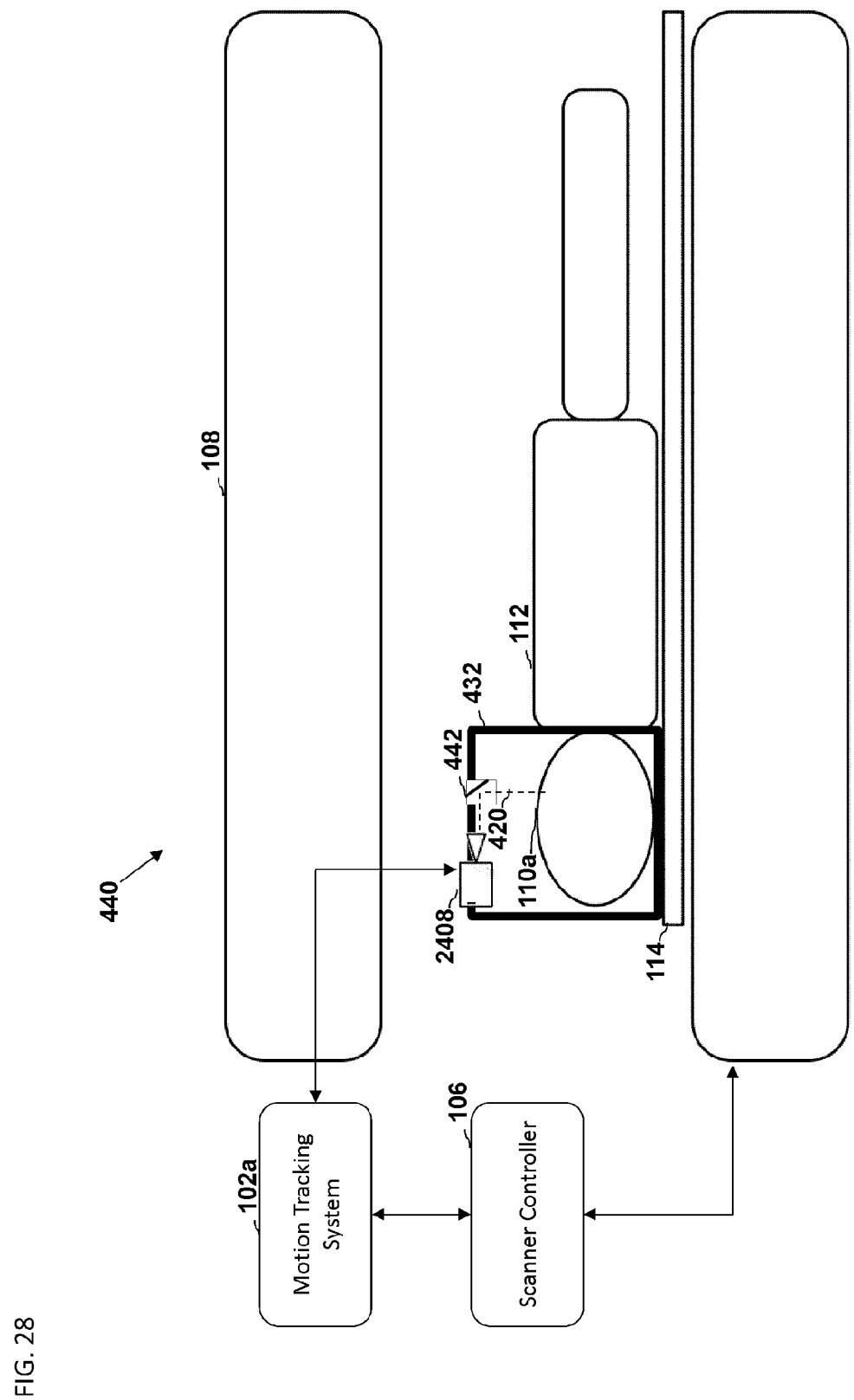
FIG. 28 is a schematic diagram illustrating a side view of the medical imaging scanner as a part of the motion compensation system of FIG. 27.

Any of the embodiments disclosed herein can be combined with the system illustrated in FIGS. 27 and 28. FIG. 27 is another embodiment of a schematic diagram illustrating a front view of a medical imaging scanner 108 as part of a motion compensation system 440. FIG. 28 is a schematic diagram illustrating a side view of the medical imaging scanner 108 as a part of the motion compensation system 440. The motion compensation system 440 is similar to the motion compensation system 430 illustrated in FIGS. 25 and 26. However, in some cases, there can be limited space within the bore of a scanner 108 and/or the cage 432. In those cases, it can be difficult to position detectors 2408 to have a direct line of sight between their lens and the landmark 110a. Accordingly, the motion compensation system 440 comprises two detectors 2408 positioned flat against the head cage 432 with a line of sight 420 being through a mirror 442 to the landmark 110a. The mirrors 442 enable an indirect line of sight to make the system more compact but to still enable viewing of the landmark 110a from along two different lines of sight 420. Although this embodiment illustrates the use of mirrors with detectors mounted to a head cage, various other embodiments may use mirrors and/or detectors attached to the scanner body, the head cage, or any other location, as long as the detectors can view the optical marker through the mirrors. In some embodiments, multiple mirrors are used to redirect the line of sight 420 multiple times. For example, a detector 2408 may be positioned outside of the scanner and have its line of sight pass through one or more mirrors positioned within the scanner to image the optical marker.

Although the motion compensation system 440 comprises mirrors to redirect the lines of sight, other methods of redirecting a line of sight may be used, alone or in combination with mirrors. For example, fiber optics or prisms may be used to redirect a line of sight and create a virtual scissor angle.

Figure 29:
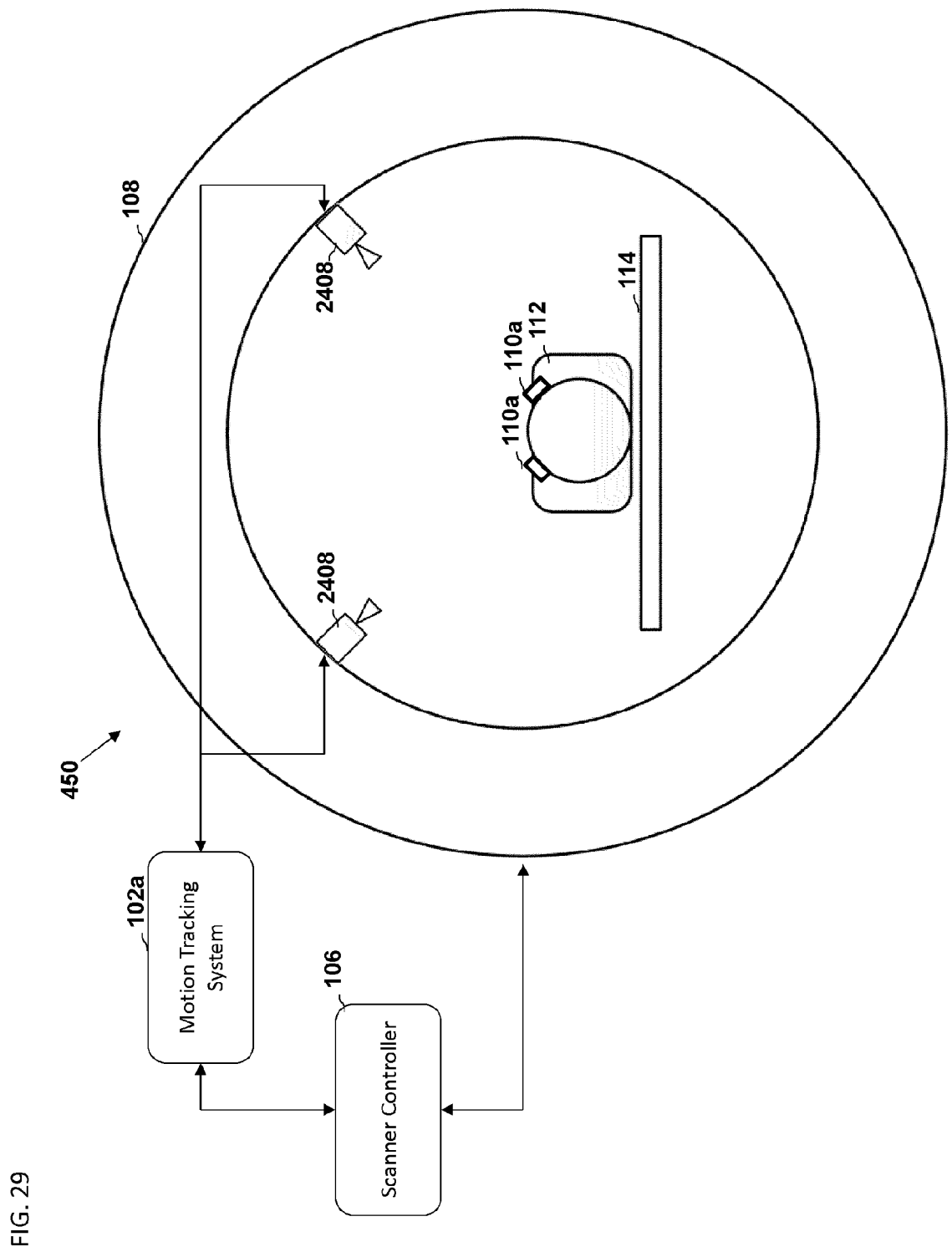
FIG. 29 is another embodiment of a schematic diagram illustrating a front view of a medical imaging scanner as part of a motion compensation system.

Any of the embodiments disclosed herein can be combined with the system illustrated in FIG. 29. FIG. 29 is another embodiment of a schematic diagram illustrating a front view of a medical imaging scanner 108 as part of a motion compensation system 450. The motion compensation system 450 is similar to the motion compensation system 100 illustrated in FIG. 1. However, the motion compensation system 450 comprises two landmarks 110a. In this embodiment, each of the two landmarks 110a are directly in the line of sight of one of the detectors 2408. However, in other embodiments, multiple landmarks 110a may be selected. For example, multiple landmarks can be selected at various rigid or substantially rigid portions of the object being imaged. For example, as further described below, one landmark 110a can be a patient's top teeth, while one or more other landmarks can be selected from a patient's forehead.

Landmarks may also be selected from locations that are not rigid or substantially rigid. For example, a landmark may be selected from a patient's skin. In an embodiment, such as when the landmark is selected from a patient's skin, due to skin movement or skin elasticity, the landmark may at times move in relation to the object being scanned, which can introduce inaccuracies into a medical imaging scan. Accordingly, in some embodiments, a motion compensation system can be configured to differentiate between movements of the object being scanned, such as a patient's head, and skin movement, which may not correlate to actual movement of the object being scanned. In some embodiments, the system can be configured to compare the positioning of two or more landmarks relative to themselves in order to differentiate between head movement and skin movement.

Utilizing multiple landmarks 110a can have various benefits. For example, multiple landmarks may be used for redundancy, in case one or more landmarks is not currently visible to one or more detectors based on the current object's pose. Another advantage is that multiple landmarks can be analyzed simultaneously by the motion tracking system 102a to obtain multiple object pose estimates. Those multiple object pose estimates can then be combined to generate a single more accurate estimate. For example, the multiple estimates can be averaged to come up with an average estimate. In another example, there may be a measure of margin of error for each estimate and the estimates may be combined using a weighted average based on the margin of error. In other embodiments, only the most accurate estimate is used and other estimates are dropped.

Figure 30:
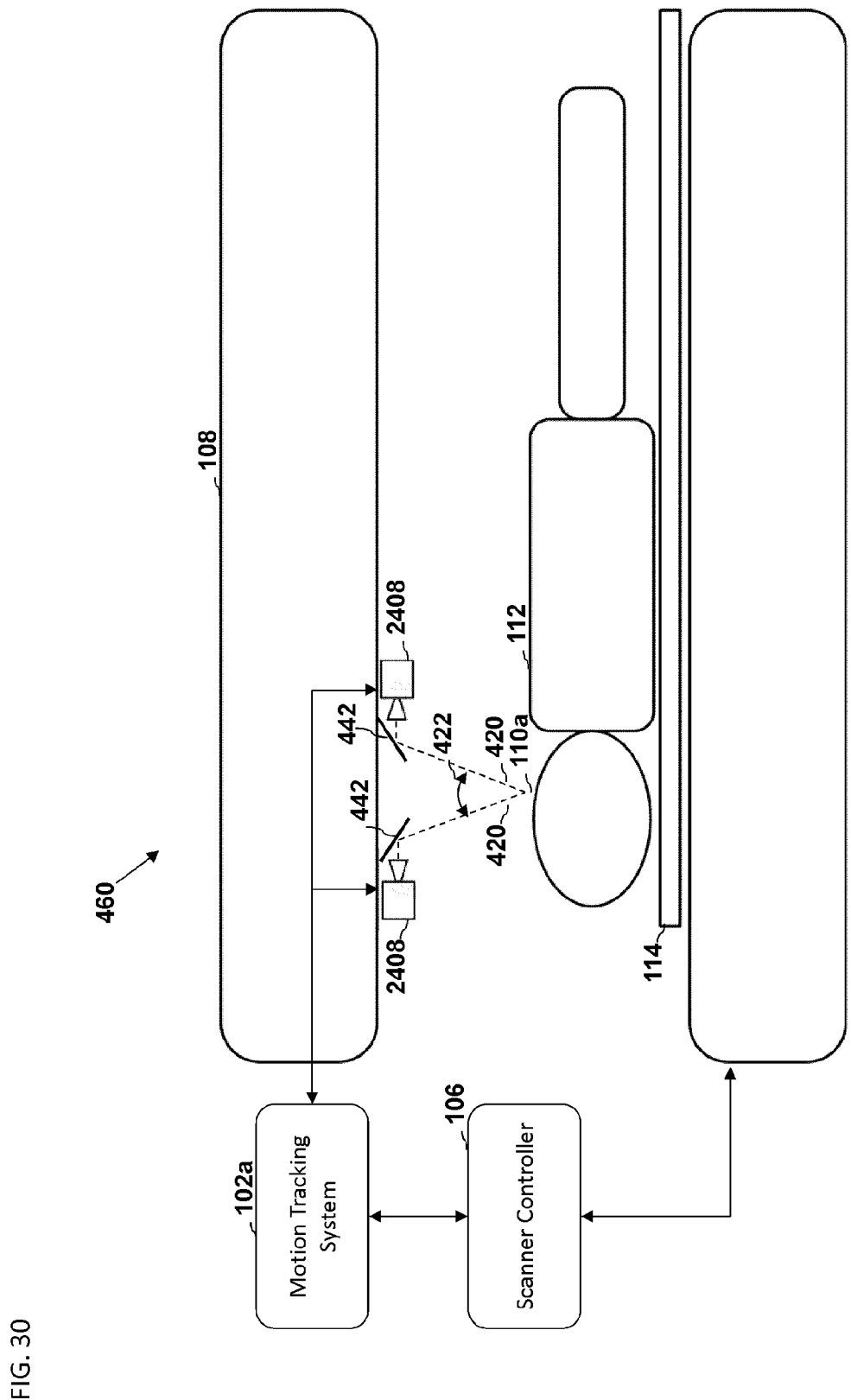
FIG. 30 is another embodiment of a schematic diagram illustrating a side view of a medical imaging scanner as part of a motion compensation system.
Figure 31:
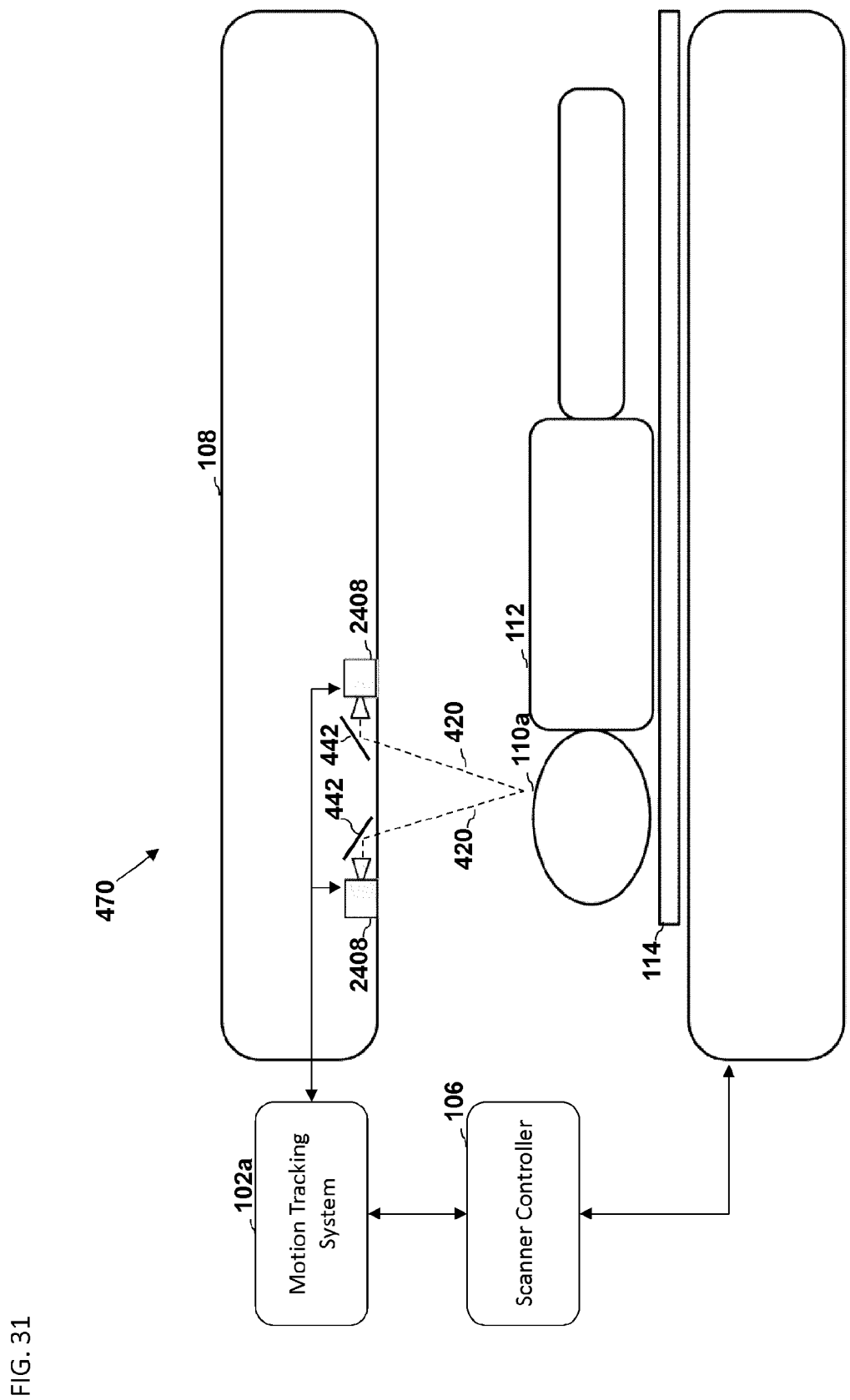
FIG. 31 is another embodiment of a schematic diagram illustrating a side view of a medical imaging scanner as part of a motion compensation system.

Any of the embodiments disclosed herein can be combined with the system illustrated in FIGS. 30-31. FIGS. 30-31 illustrate additional embodiments of motion compensation systems configured to use indirect lines of sight. Given that many medical imaging systems have limited space within the bore of the device, it can be advantageous to position detectors to be generally flat against a bore of the device or flush within the bore of the device. The embodiment of a motion tracking system 460 shown in FIG. 30 illustrates a system wherein two optical detectors 2408 are positioned flat against a bore of the medical imaging scanner 108. In this embodiment, the detectors 2408 are positioned facing each other along a longitudinal axis of the bore. Two mirrors 442 are positioned relatively close to the detectors to redirect their lines of sight 120 toward the landmark 110a. In this embodiment, the scissor angle 422 is significantly smaller than 90 degrees. However, in other embodiments, the detectors and/or mirrors may be positioned differently to increase or decrease the scissor angle 422.

The motion compensation system 470 illustrated in FIG. 31 is similar to the motion compensation system 460 illustrated in FIG. 30. However, the motion compensation system 470 comprises two detectors 2408 and two mirrors 442 mounted within the medical imaging scanner 108 such that they do not protrude into the bore of the scanner 108. The scanner 108 body can comprise openings to enable the lines of sight 420 to pass from the landmark 110a to the detectors 2408. In some embodiments, detectors may be positioned on a surface of the scanner bore, partially within the body of the scanner, fully within the body of the scanner, and/or the like. One determining factor of whether detectors can be mounted within a scanner body and/or whether any of the detector must protrude beyond the scanner body is the size of the detectors and the space available within the scanner body. More space available within the scanner body and/or smaller detectors may enable more or all of the detectors to be positioned within the scanner body.

Figure 32:
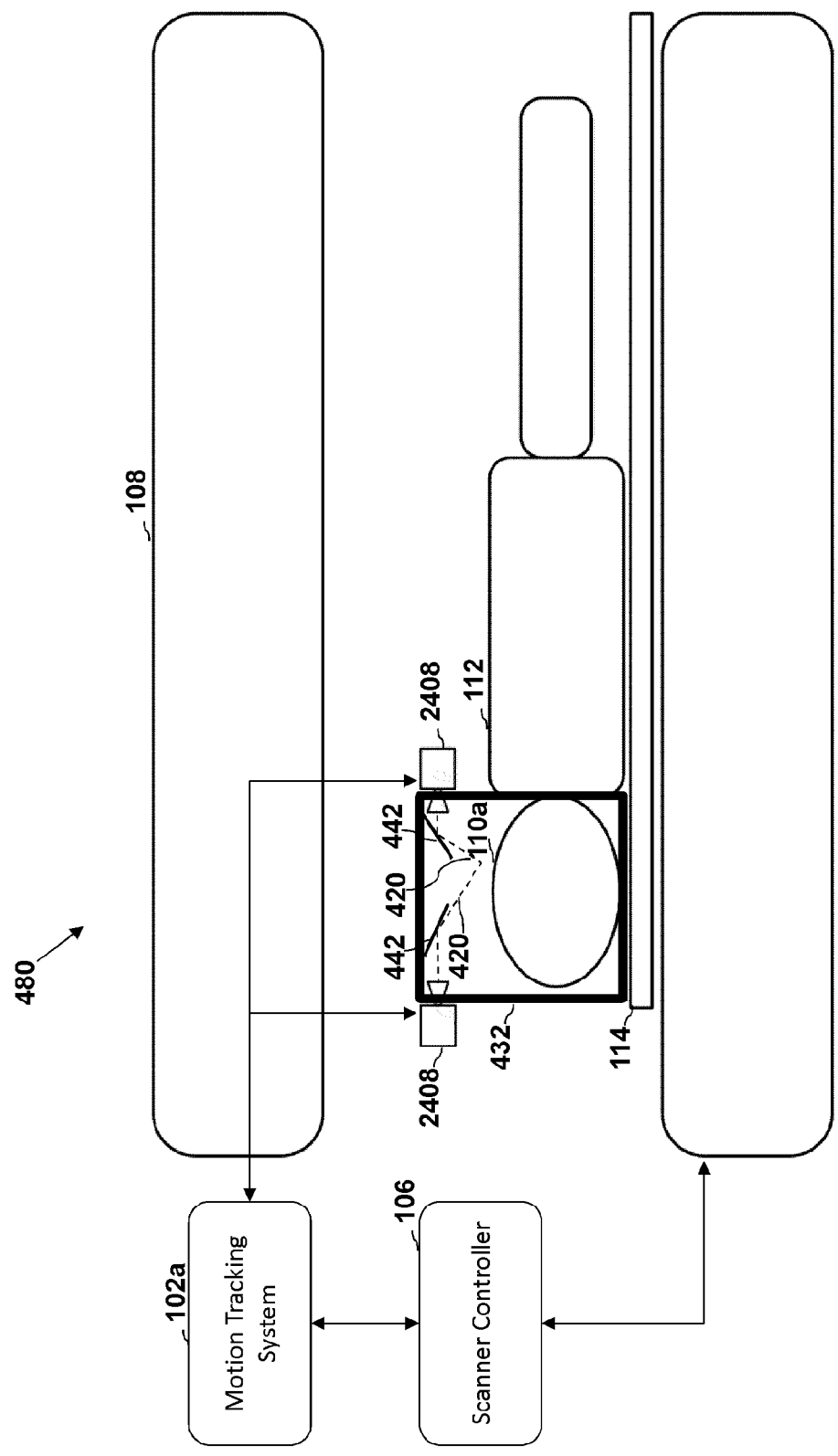
FIG. 32 is another embodiment of a schematic diagram illustrating a side view of a medical imaging scanner as part of a motion compensation system.

Any of the embodiments disclosed herein can be combined with the system illustrated in FIG. 32. FIG. 32 illustrates a motion compensation system 480. The motion compensation system 480 is similar to the motion compensation system 460 illustrated in FIG. 30. However, the motion compensation system 480 comprises a head cage 432, and the detectors 2408 and mirrors 442 are mounted opposite each other on opposite ends of the head cage 432, rather than being mounted to the bore of the scanner. In various embodiments, the detectors 2408 may be mounted in various positions, not necessarily facing each other. For example, both detectors 2408 may be positioned on the same side of the head cage 432. As can be seen in FIG. 32, each of the two detectors 2408 is configured to view the landmark 110a along a line of sight 420 viewing the landmark 110a along a different angle relative to the landmark 110a. The line of sight 420 on the left-hand side is at a shallower angle than the line of sight 420 on the right-hand side. In other embodiments, the positioning of the detectors, the optical marker, and/or the mirrors may be adjusted to adjust the angles of each of the lines of sight relative to the marker and/or to adjust the scissor angle.

Computing System

Figure 34:
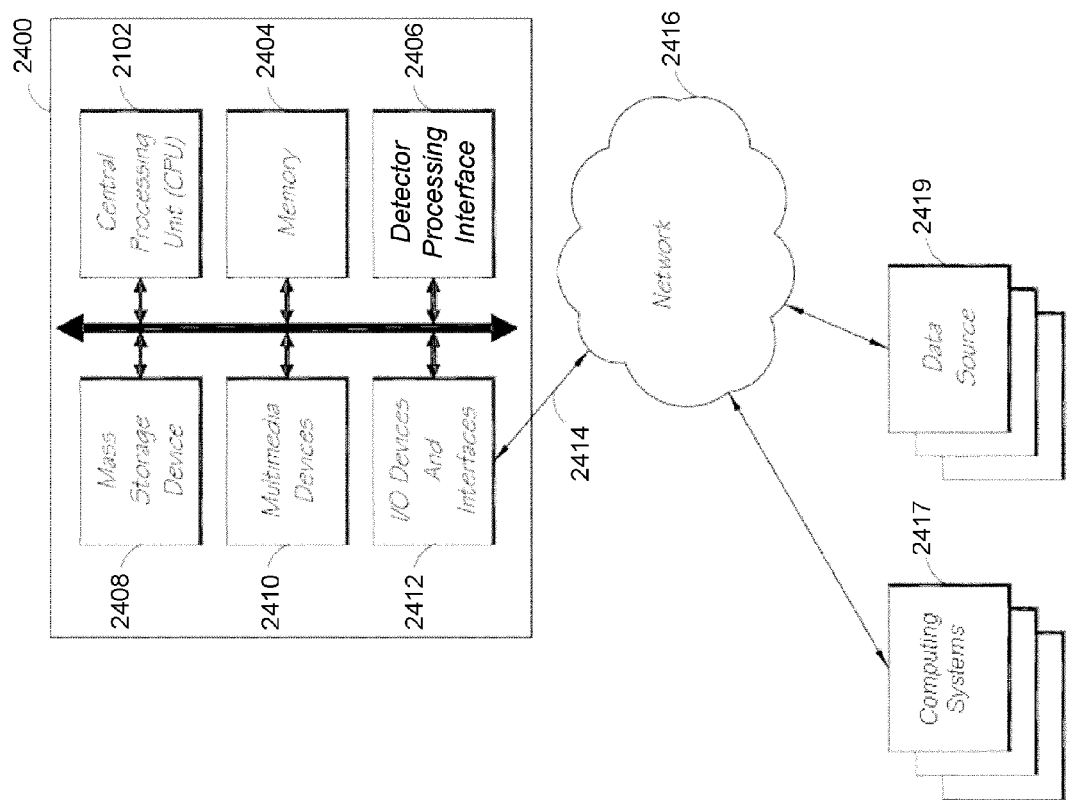
FIG. 34 is a block diagram depicting an embodiment of a computer hardware system configured to run software for implementing one or more embodiments of the motion tracking systems described herein.

FIG. 34 is a block diagram depicting an embodiment of a computer hardware system configured to run software for implementing one or more embodiments of the motion tracking systems described herein.

In some embodiments, the computer clients and/or servers described above take the form of a computing system 3400 illustrated in FIG. 34, which is a block diagram of one embodiment of a computing system that is in communication with one or more computing systems 3417 and/or one or more data sources 3419 via one or more networks 3416. The computing system 3400 may be used to implement one or more of the systems and methods described herein. In addition, in one embodiment, the computing system 3400 may be configured to manage access or administer a software application. While FIG. 34 illustrates one embodiment of a computing system 3400, it is recognized that the functionality provided for in the components and modules of computing system 3400 may be combined into fewer components and modules or further separated into additional components and modules.

Detector Processing Interface

In one embodiment, the computing system 3400 comprises a detector processing interface 3406 that carries out the functions described herein with reference to tracking motion during a scan, including any one of the motion tracking techniques described above. In some embodiments, the computing system 3400 additionally comprises a scanner controller, an anatomy configuration module, an image processing system, a scanner image acquisition module, and/or an image overlay module that carries out the functions described herein with reference to tracking motion during a scan and/or storing or overlaying tracking data with associated scanner images. The detector processing interface 3406 and/or other modules may be executed on the computing system 3400 by a central processing unit 3402 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into submodules despite their physical organization or storage.

Computing System Components

In one embodiment, the computing system 3400 also comprises a mainframe computer suitable for controlling and/or communicating with large databases, performing high volume transaction processing, and generating reports from large databases. The computing system 3400 also comprises a central processing unit ("CPU") 3402, which may comprise a conventional microprocessor. The computing system 3400 further comprises a memory 3404, such as random access memory ("RAM") for temporary storage of information and/or a read only memory ("ROM") for permanent storage of information, and a mass storage device 3408, such as a hard drive, diskette, or optical media storage device. Typically, the modules of the computing system 3400 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 3400 comprises one or more commonly available input/output (I/O) devices and interfaces 3412, such as a keyboard, mouse, touchpad, and printer. In one embodiment, the I/O devices and interfaces 3412 comprise one or more display devices, such as a monitor, that allows the visual presentation of data to a user. More particularly, a display device provides for the presentation of GUIs, application software data, and multimedia presentations, for example. In one or more embodiments, the I/O devices and interfaces 3412 comprise a microphone and/or motion sensor that allow a user to generate input to the computing system 3400 using sounds, voice, motion, gestures, or the like. In the embodiment of FIG. 34, the I/O devices and interfaces 3412 also provide a communications interface to various external devices. The computing system 3400 may also comprise one or more multimedia devices 3410, such as speakers, video cards, graphics accelerators, and microphones, for example.

Computing System Device/Operating System

The computing system 3400 may run on a variety of computing devices, such as, for example, a server, a Windows server, a Structure Query Language server, a Unix server, a personal computer, a mainframe computer, a laptop computer, a tablet computer, a cell phone, a smartphone, a personal digital assistant, a kiosk, an audio player, an e-reader device, and so forth. The computing system 3400 is generally controlled and coordinated by operating system software, such as z/OS, Windows 95, Windows 98, Windows NT, Windows 2000, Windows XP, Windows Vista, Windows 7, Windows 8, Linux, BSD, SunOS, Solaris, Android, iOS, BlackBerry OS, or other compatible operating systems. In Macintosh systems, the operating system may be any available operating system, such as MAC OS X. In other embodiments, the computing system 3400 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 34, the computing system 3400 is coupled to a network 3416, such as a LAN, WAN, or the Internet, for example, via a wired, wireless, or combination of wired and wireless, communication link 3414. The network 3416 communicates with various computing devices and/or other electronic devices via wired or wireless communication links. In the embodiment of FIG. 34, the network 3416 is communicating with one or more computing systems 3417 and/or one or more data sources 3419.

Access to the detector processing interface 3406 of the computer system 3400 by computing systems 3417 and/or by data sources 3419 may be through a web-enabled user access point such as the computing systems' 3417 or data source's 3419 personal computer, cellular phone, smartphone, laptop, tablet computer, e-reader device, audio player, or other device capable of connecting to the network 3416. Such a device may have a browser module that is implemented as a module that uses text, graphics, audio, video, and other media to present data and to allow interaction with data via the network 3416.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 3412 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 3400 may comprise a physical or logical connection established between a remote microprocessor and a mainframe host computer for the express purpose of uploading, downloading, or viewing interactive data and databases on-line in real time. The remote microprocessor may be operated by an entity operating the computer system 3400, including the client server systems or the main server system, an/or may be operated by one or more of the data sources 3419 and/or one or more of the computing systems 3417. In some embodiments, terminal emulation software may be used on the microprocessor for participating in the micro-mainframe link.

In some embodiments, computing systems 3417 who are internal to an entity operating the computer system 3400 may access the detector processing interface 3406 internally as an application or process run by the CPU 3402.

User Access Point

In an embodiment, a user access point or user interface comprises a personal computer, a laptop computer, a tablet computer, an e-reader device, a cellular phone, a smartphone, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, or the like.

Other Systems

In addition to the systems that are illustrated in FIG. 34, the network 3416 may communicate with other data sources or other computing devices. The computing system 3400 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

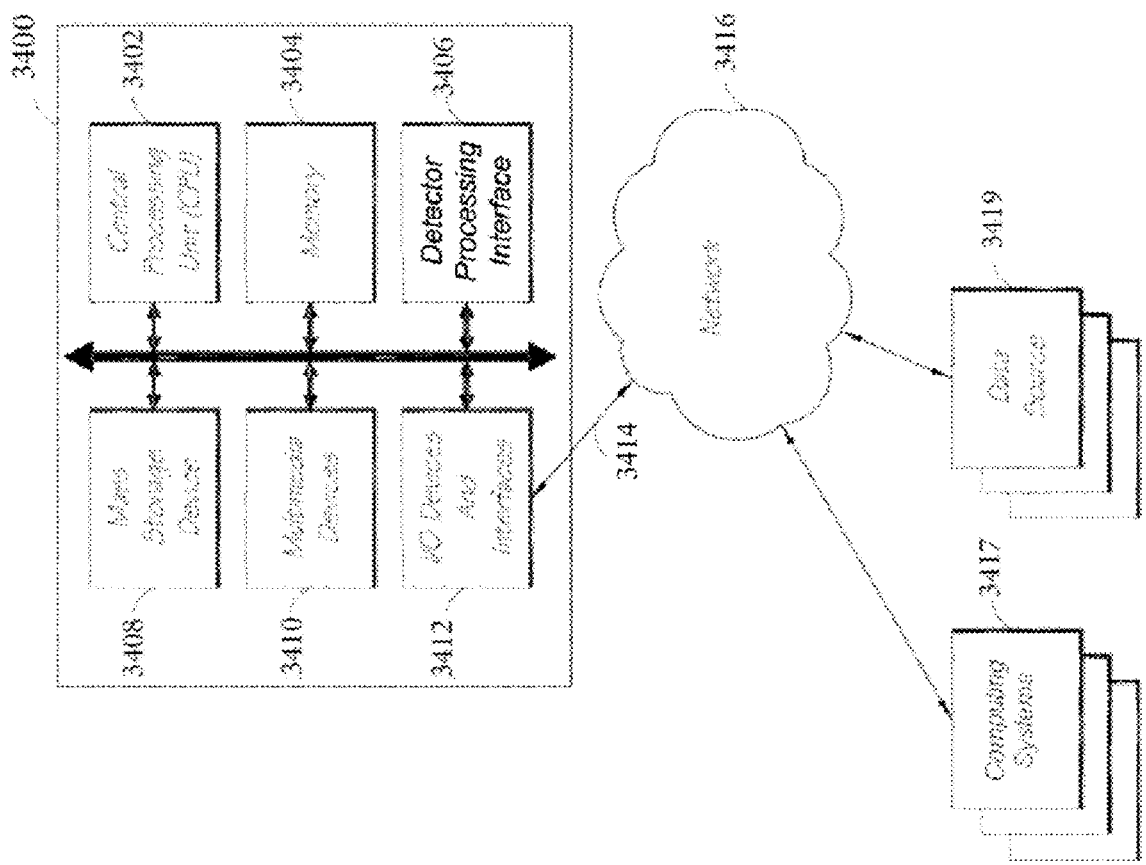

What is claimed is:

1. A biomedical system for tracking motion of an object during biomedical imaging and for compensating for motion of the object, the biomedical system comprising:
   a biomedical imaging scanner configured to perform scanning of the object to generate biomedical images of the object;
   at least one detector for generating data describing at least a first landmark and a second landmark of the object, wherein the at least one detector is configured to be positioned relative to the object to enable the at least one detector to detect movement of the first landmark and the second landmark during the scanning;
   one or more computer readable storage devices configured to store a plurality of computer executable instructions; and
   one or more hardware computer processors in communication with the one or more computer readable storage devices and configured to execute the plurality of computer executable instructions in order cause the biomedical system to:
      utilize a first motion tracking technique to determine motion of the first landmark;
      utilize a second motion tracking technique to determine motion of the second landmark;
      apply a first weighting factor to the determined motion of the first landmark, wherein the first weighting factor is based on a historical accuracy of the first motion tracking technique;
      apply a second weighting factor to the determined motion of the second landmark, wherein the second weighting factor is based on a historical accuracy of the second motion tracking technique;
      determine motion of the object based on analyzing the determined motion of the first landmark and the second landmark;
      generate motion tracking data of the object; and
      control at least one parameter of the biomedical imaging scanner to adjust scanner parameters based on the motion tracking data, the scanner parameters configured for controlling the biomedical imaging scanner to account for motion of the object during the scanning of the object.

2. The biomedical system of claim 1, wherein the at least one detector is positioned within a bore of the biomedical imaging scanner.

3. The biomedical system of claim 2, wherein the at least one detector only comprises components configured to not interfere with the biomedical imaging scanner.

4. The biomedical system of claim 1, wherein at least one of the first landmark and the second landmark comprises a facial feature of the subject.

5. The biomedical system of claim 4, wherein the facial feature comprises at least one tooth of the upper jawbone.

6. The biomedical system of claim 1, wherein at least one of the first landmark and the second landmark comprises an organ of the subject.

7. The biomedical system of claim 1, wherein at least one of the first landmark and the second landmark comprises an image projected onto the subject.

8. The biomedical system of claim 1, wherein the biomedical system is configured to utilize an atlas-segmentation technique for identifying the at least one landmark of the object.

9. A computer implemented-method for tracking motion of an object during biomedical imaging by a scanner and for compensating for motion of the object, the computer implemented-method comprising:
   accessing, by a computer system, an image of the object;
   identifying, by the computer system, in the image a first landmark of the object, the first landmark being a feature naturally existing in the object, the identifying of the first landmark performed by utilizing a first motion tracking technique to determine motion of the first landmark;
   identifying, by the computer system, in the image a second landmark of the object, the identifying of the second landmark performed by utilizing a second motion tracking technique to determine the motion of the second landmark;
   accessing, by the computer system, a plurality of images of the object;
   tracking, by the computer system, movement of the first landmark and the second landmark in the plurality of images of the object, wherein the movement is an average of the motion of the first landmark and the motion of the second landmark, wherein the movement is determined by applying a first weighting factor to the determined motion of the first landmark to generate a first weighted motion, and applying a second weighting factor to the determined motion of the second landmark to generate a second weighted motion, and averaging the first and second weighted motions, wherein the first weighting factor is based on a historical accuracy of the first motion tracking technique and the second weighting factor is based on a historical accuracy of the second motion tracking technique;
   translating, by the computer system, the movement in a first reference plane to a second reference plane of the scanner;
   generating, by the computer system, data parameters based on the movement in the second reference plane, the data parameters configured to adjust the scanning parameters of the scanner to account for motion of the object; and
   transmitting, by the computer system, the data parameters to a scanner controller, the scanner controller configured to control the scanning parameters of the scanner.

10. The computer-implemented method of claim 9, wherein the image is from a video.

11. The computer-implemented method of claim 9, wherein the accessing of the image of the object is from at least one detector that is positioned within a bore of the scanner.

12. The computer-implemented method of claim 11, wherein the at least one detector only comprises components configured to not interfere with the scanner.

13. The computer-implemented method of claim 9, wherein the first landmark comprises a facial feature.

14. The computer-implemented method of claim 13, wherein the facial feature comprises at least one tooth of the upper jawbone.

15. The computer-implemented method of claim 9, wherein the first landmark comprises an organ.

16. The computer-implemented method of claim 9, wherein the identifying the first landmark comprises utilizing an atlas-segmentation technique for identifying the first landmark of the object.

* * * * *

UNITED STATES PATENT AND TRADEMARK OFFICE
CERTIFICATE OF CORRECTION

PATENT NO. : 9,782,141 B2
APPLICATION NO. : 14/762583
DATED : October 10, 2017
INVENTOR(S) : Jeffrey N. Yu et al.

Page 1 of 3

It is certified that error appears in the above-identified patent and that said Letters Patent is hereby corrected as shown below:

On the Title Page

In Column 1 (page 7, item (56)) at Line 36, Under Other Publications, change ""Hybrind" to --"Hybrid--.

In Column 1 (page 7, item (56)) at Line 50, Under Other Publications, change "Breain"," to --Brain",--.

In Column 1 (page 7, item (56)) at Line 58, Under Other Publications, change "magnetric" to --magnetic--.

In Column 2 (page 7, item (56)) at Line 14, Under Other Publications, change "Continous" to --Continuous--.

In Column 2 (page 8, item (56)) at Line 24, Under Other Publications, change "Technion-lsrael" to --Technion-Israel--.

In the Drawings

In Figure 34, sheet 34 of 34, for "Computing System," change reference numeral "2400" to --3400--, as shown on the attached page.

In Figure 34, sheet 34 of 34, for "Central Processing Unit (CPU)," change reference numeral "2102" to --3402--, as shown on the attached page.

In Figure 34, sheet 34 of 34, for "Memory," change reference numeral "2404" to --3404--, as shown on the attached page.

In Figure 34, sheet 34 of 34, for "Detector Processing Interface," change reference numeral "2406" to --3406--, as shown on the attached page.

Signed and Sealed this
Third Day of April, 2018

Andrei Iancu
*Director of the United States Patent and Trademark Office*

In Figure 34, sheet 34 of 34, for "Mass Storage Device," change reference numeral "2408" to --3408--, as shown on the attached page.

In Figure 34, sheet 34 of 34, for "Multimedia Devices," change reference numeral "2410" to --3410--, as shown on the attached page.

In Figure 34, sheet 34 of 34, for "I/O Devices and Interfaces," change reference numeral "2412" to --3412--, as shown on the attached page.

In Figure 34, sheet 34 of 34, for "Communication Link," change reference numeral "2414" to --3414--, as shown on the attached page.

In Figure 34, sheet 34 of 34, for "Network," change reference numeral "2416" to --3416--, as shown on the attached page.

In Figure 34, sheet 34 of 34, for "Computing Systems," change reference numeral "2417" to --3417--, as shown on the attached page.

In Figure 34, sheet 34 of 34, for "Data Source," change reference numeral "2419" to --3419--, as shown on the attached page.

In the Specification

In Column 36 at Line 20, Change "an/or" to --and/or--.

In the Claims

In Column 38 at Line 13, In Claim 9, change "computer implemented-method" to --computer implemented method--.